United States Patent [19]

Jung

[11] Patent Number: 4,463,173

[45] Date of Patent: Jul. 31, 1984

[54] CEPHALOSPORIN DERIVATIVES

[75] Inventor: Frederic H. Jung, Reims, France

[73] Assignee: ICI Pharma, Enghien-les-Bains, France

[21] Appl. No.: 219,879

[22] Filed: Dec. 24, 1980

[30] Foreign Application Priority Data

Dec. 24, 1979 [FR] France ................................ 79 31616

[51] Int. Cl.³ .......................................... C07D 50/116
[52] U.S. Cl. ......................................... 544/27; 544/16; 544/22; 544/24; 544/25; 544/26; 544/28; 544/30
[58] Field of Search .................... 424/246; 544/22, 27, 544/28, 16, 24, 25, 26, 30

[56] References Cited

U.S. PATENT DOCUMENTS 4,255,424 3/1981 Hannah ................................ 544/333
4,282,219 8/1981 Hannah ................................ 544/22
4,358,447 11/1982 Hannah ................................ 544/22

FOREIGN PATENT DOCUMENTS 18595 12/1980 European Pat. Off. .

Primary Examiner—Paul M. Coughlan, Jr.
Attorney, Agent, or Firm—Cushman, Darby & Cushman

[57] ABSTRACT

A compound of the formula I:

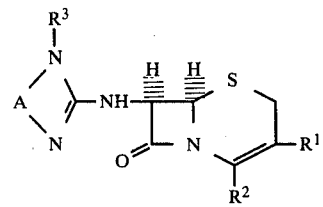

in which $R^1$ is any C-3 substituent from antibacterially-active cephalosporins; $R^2$ is any C-4 substituent from antibacterially-active cephalosporins; $R^3$ is H, hydroxy, amino, 1-6C alkyl, 1-6C alkanoyl, 1-6C alkoxy, 1-6C alkanoylamino or 1-6C alkylamino, phenyl(1-6C)-alkyl or phenyl, each optionally substituted by methoxy;

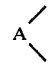

is of the formula II or III:

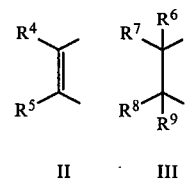

II    III in which $R^4$, $R^5$, $R^6$, $R^7$, $R^8$ and $R^9$ may have a variety of values, e.g. hydrogen, carboxy, cyano or alkyl; and the salts thereof.

Manufacturing processes, pharmaceutical compositions and a method of treating a bacterial infection are also disclosed.

4 Claims, No Drawings

CEPHALOSPORIN DERIVATIVES

This invention relates to cephalosporin derivatives which have antibacterial properties.

The vast majority of therapeutically useful antibiotics based on the pencillin and cephalosporin ring systems have an acylamino radical at the 6β and 7β positions respectively. A number of other substituents at these positions have been investigated but in the main the resulting compounds have at best possessed only weak antibacterial activity. An exception to this generalisation is the amidino substituent. Penicillin derivatives carrying a substituted amidino radical in the 6β position (see for example UK Pat. Nos. 1,315,566 and 1,406,732) have been found to have useful antibacterial activity and two such compounds, mecillinam and pivmecillinam, are commercially available. However cephalosporin derivatives carrying a corresponding amidino radical in the 7β position (German Offenlegungschrift No. 2,430,375) have been found to have a surprisingly low level of antibacterial activity. (F J Lund, "6β-Amidino Penicilanic Acids-Synthesis and Antibacterial Properties", in "Recent Advances in the Chemistry of β-Lactam Antibiotics" edited by J Elks, The Chemical Society Special Publication No.28, London 1977, pages 42–43 and J Altman et al., *J.Med.Chem.*, 1975, 18, 627–630).

It has now been discovered that if a guanidine radical, in which two of the nitrogen atoms are joined by means of a two carbon bridge to form a 2-imidazoline or imidazole ring, is introduced into the 7β position of the cephalosporin nucleus, these are produced compounds having marked antibacterial properties.

According to the invention there is provided a cephalosporin derivative of the formula:

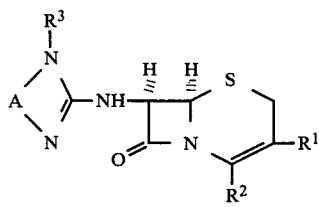

in which $R^1$ is any one of the C-3 substituents from antibacterially-active cephalosporins known in the art; $R^2$ is any one of the C-4 substituents from antibacterially-active cephalosporins known in the art. $R^3$ is a hydrogen atom, a hydroxy or amino radical, an alkyl, alkanoyl, alkoxy, alkanoylamino or alkylamino radical, each of 1 to 6 carbon atoms, a phenylalkyl radical in which the alkyl part is of 1 to 6 carbon atoms or a phenyl radical, in the latter two of which the phenyl ring is optionally substituted by a methoxy radical;

A

is a radical of the formula:

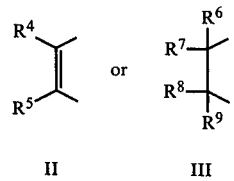

in which $R^4$ and $R^5$, which may be the same or different are hydrogen or halogen atoms, cyano, hydroxy, carboxy or pyridyl radicals, alkyl, aminoalkyl or hydroxyalkyl radicals of 1 to 6 carbon atoms, alkoxycarbonyl radicals of 2 to 6 carbon atoms, alkylaminoalkyl radicals of 2 to 10 carbon atoms, dialkylaminoalkyl radicals of 3 to 15 carbon atoms, or phenyl radicals optionally substituted by 1 or 2 radicals selected from halogen atoms, nitro, amino, hydroxy, carboxy and cyano radicals, alkyl radicals of 1 to 6 carbon atoms and alkoxycarbonyl radicals of 2 to 6 carbon atoms;

or $R^4$ and $R^5$ are joined to form, together with the carbon atoms to which they are attached, a mono-, bi- or tri-cyclic carbocyclic ring system which may be non-aromatic, partially aromatic or fully aromatic, the aromatic part of such a ring system being optionally substituted by 1, 2 or 3 radicals selected from halogen atoms, hydroxy, amino, cyano, carboxy, carbamoyl, nitro and ureido radicals, alkyl, alkoxy, haloalkyl, alkylamino, hydroxyalkyl, aminoalkyl, alkanoylamino and azidoalkyl radicals each of 1 to 6 carbon atoms, dialkylamino and acetylaminoethyl radicals of 2 to 8 carbon atoms, alkylaminoalkyl radicals of 2 to 10 carbon atoms, dialkylaminoalkyl radicals of 3 to 15 carbon atoms, cyanoalkyl, carboxyalkyl, carbamoylalkyl and ureidoalkyl radicals each of 2 to 6 carbon atoms, and radicals of the formula:

$$OCONH_2 \quad\quad IV$$

$$(CH_2)_n-N=CH-N\underset{\phantom{x}}{\bigcirc}(CH_2)_m \quad V$$

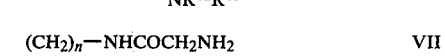

$$(CH_2)_n-NHCOCH_2NH_2 \quad VII$$
$$(CH_2)_n-NHCOCH(Ph)NH_2 \quad VIII$$
$$\text{and } (CH_2)_n-NHCN \quad IX$$

in which n is 0 to 6, m is 4 to 8 and $R^{10}$, $R^{11}$, $R^{12}$ and $R^{13}$, which may be the same or different, are hydrogen atoms or alkyl radicals of 1 to 6 carbon atoms; and $R^6$, $R^7$, $R^8$ and $R^9$, which may be the same or different, are hydrogen atoms, carboxy, cyano carbamoyl, methoxycarbonyl, aminoethyl or pyridyl radicals, alkanoyl or hydroxyalkyl radicals of 1 to 6 carbon atoms, alkyl radicals of 1 to 10 carbon atoms, phenoxyalkyl radicals in which the alkyl part is of 1 to 6 carbon atoms and the phenyl ring is optionally substituted by a diphenylmethyl radical, or phenyl radicals which are optionally substituted by 1, 2 or 3 radicals selected from halogen atoms and cyano, amino, carboxy, carbamoyl, hydroxy, phenyl, phenoxy and diphenylmethyl radicals, alkylamino, alkanoylamino, alkanesulphonylamino, aminoalkyl and hydroxyalkyl radicals each of 1 to 6 carbon atoms, dialkylamino radicals of 2 to 10 carbon atoms, alkoxycarbonyl and alkylcarbamoyl radicals of 2 to 6 carbon atoms and dialkylcarbamoyl radicals of 3 to 10 carbon atoms;

or $R^7$ and $R^8$, when in the cis relationship, are joined to form, together with the carbon atoms to which they are attached, a 3 to 6 membered carbocyclic ring, the ring being optionally substituted by 1 or 2 radicals selected from phenyl radicals and haloalkyl radicals of 1 to 6 carbon atoms and the 4 to 6 membered rings optionally containing a double bond in a position other than at the ring fusion;

provided that when one of $R^6$, $R^7$, $R^8$ and $R^9$ is a carboxy radical the remaining members of $R^6$, $R^7$, $R^8$ and $R^9$ are hydrogen atoms;

and where the compound of the formula I contains a free basic or acidic group, the pharmaceutically-acceptable acid- or base-addition salts respectively thereof.

It is to be understood that in the above formula I and throughout this specification, the illustrated stereochemistry of the ceph-3-em nucleus of the formula:

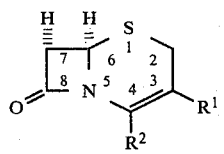   X is the absolute configuration. It is also to be understood that, although the double bond or bonds in formula I, II, V and VI have been inserted in particular positions, other tautomeric forms are, in certain instances, possible, and these other forms are included within the scope of the invention. Note, however, that the $\Delta^3$ double bond between $R^1$ and $R^2$ is fixed in position. It is also to be understood that when the compound of the formula I contains both an acidic and basic centre, the compound may exist in the form of a zwitterion.

It will be observed that, when

is a radical of the formula III, the compound of the formula I may contain 1 or 2 carbon atoms, each of which carries non-identical atoms or radicals $R^6$ and $R^7$, and $R^8$ and $R^9$. When one such carbon atom is present, the compound of the formula I will exist in 2 diastereoisomeric forms. When two such carbon atoms are present, the compound of the formula I will exist in 4 diastereoisomeric forms. It is to be understood that the useful properties, as hereinafter defined, of these diastereoisomers may differ and it is therefore to be understood that when

is a radical of the formula III, this invention encompasses the diastereoisomeric mixture represented by the formula I and any individual diastereoisomer which possesses the useful properties, it being a matter of common general knowledge how to obtain such individual diastereoisomers and determine the biological properties of each. Similar remarks apply when the compound of the formula I contains an asymmetric centre in another part of the molecule.

The cephalosporin derivative of the formula I may be manufactured by methods known in themselves for the manufacture of chemically analogous compounds. The following processes, $R^1$, $R^2$, $R^3$ and A having the meaning stated above, unless indicated otherwise, are therefore provided as further features of the invention.

The process of the invention is characterised by:

(a) for those compounds in which $R^2$ is a carboxy radical or a heterocyclic radical carrying an acidic proton, and there is optionally a carboxy radical in another part of the molecule, deprotection of the corresponding compound which carries a protecting group, or groups, in place of the acidic hydrogen atom, or atoms. When $R^2$ is a carboxy radical a particularly useful protecting group is the diphenylmethyl or p-methoxybenzyl radical. Such a protecting group may be removed by treatment with a strong organic acid, for example trifluoroacetic acid. A further particularly useful protecting group is the t-butyl radical. This protecting group may be removed by treatment with a strong organic acid such as trifluoroacetic or formic acid. The process may be conducted in the presence of excess organic acid as diluent or solvent or in the presence of an additional diluent or solvent such as anisole or toluene. The process is preferably conducted at or below ambient temperature and preferably over a period of from 5 minutes to 5 hours. Other useful protecting groups are the trimethylsilyl radical (removed by water), the benzyl and substituted benzyl radicals, for example the p-nitrobenzyl or p-methoxybenzyl ester, (removed by hydrogenolysis) and the 2,2,2-trichloroethyl ester (removed by zinc/acetic acid).

(b) reaction of a compound of the formula:

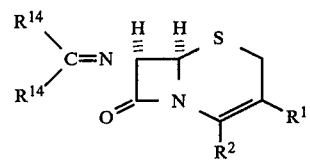   XI in which $R^{14}$ is a chlorine or bromine atom with a compound of the formula:

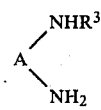   XII or, where A is of the formula II, a formal tautomer thereof.

$R^{14}$ is preferably a bromine atom. The reaction may be carried out in a diluent or solvent, a preferred solvent being tetrahydrofuran to which may, if necessary, be added a little methanol to achieve solution. It may be necessary to use an excess of the compound of the formula XII in order to achieve optional yields of the product. The reaction may be conducted over the temperature range $-78°$ to ambient temperature depending on the nature of the starting materials, and indeed in some cases the reaction may be accelerated or completed by heating, for example by heating to 50° or to the boiling point of the diluent or solvent. The reaction is preferably conducted under an inert atmosphere, for example a nitrogen or argon atmosphere.

(c) reaction of a compound of the formula

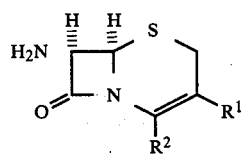   XIII with a compound of the formula:

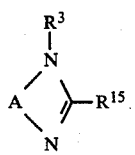   XIV in which $R^{15}$ is a displaceable radical. $R^{15}$ is for example a halogen atom, preferably a fluorine or chlorine atom. The reaction is preferably conducted in the presence of at least one equivalent of an acid in order that the compound of the formula XIV is in the protonated form. The reaction may be conducted in the presence of a diluent or solvent, for example acetonitrile, dimethylformamide or tetrahydrofuran or mixtures of these and it may be accelerated or completed by the application of heat, for example by heating to 70° or to the boiling point of the diluent or solvent. The compound of the formula XIV may conveniently be prepared in situ by prior reaction of the corresponding N-triphenylmethyl derivative with toluene-p-sulphonic acid. The compound of the formula XIII is then added to the reaction mixture.

(d) for those compounds in which $R^3$ is other than a hydrogen atom, reaction of a compound of the formula XIII with a compound of the formula:

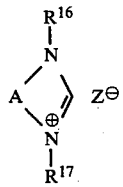   XV in which $R^{16}$ has the value given above for $R^3$ other than a hydrogen atom, $R^{17}$ is a displaceable radical and $Z^{\ominus}$ is an anion. $R^{17}$ is for example an alkoxy or alkylthio radical of 1 to 6 carbon atoms, for example a methoxy or methylthio radical. $Z^{\ominus}$ is for example a halide anion, for example a chloride, bromide or iodide, or a methanesulphonate or toluene-p-sulphonate. The reaction may be conducted in a diluent or solvent such as methanol, water or an aqueous buffer. It is preferably conducted at ambient temperature.

(e) for those compounds in which $R^1$ is a radical of the formula $CH_2Y$, reaction of a compound of the formula I in which $R^1$ is a radical of the formula $CH_2—R^{15}$ in which $R^{15}$ is a displaceable radical with a compound of the formula Y—H. $R^{15}$ is for example a halogen atom or an acetoxy radical. The reaction may be conducted in a diluent or solvent such as acetonitrile, in the presence of boron trifluoride. The reaction may be accelerated or completed by the application of heat, for example by heating to 50°.

(f) for those compounds in which $R^3$ is a hydrogen atom, replacement by hydrogen of the radical $R^{16}$ in a compound of the formula:

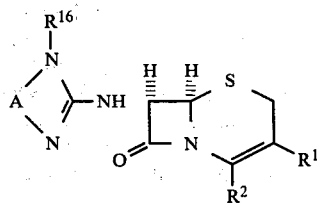   XVI in which $R^{16}$ is a hydroxy, methoxy or methylthio radical. The process may be carried out using titanium trichloride. The reaction may be conducted in a diluent or solvent such as methanol, tetrahydrofuran or methylene chloride and may be accelerated or completed by the application of heat, for example by heating to 40°–50°.

(g) for those compound in which $R^3$ is an alkyl, alkanoyl or optionally substituted phenylalkyl radical, alkylation or acylation of the corresponding compound in which $R^3$ is a hydrogen atom;

(h) cyclisation of a compound of the formula:

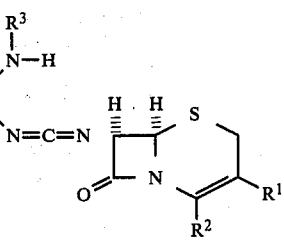   XVII or (i) cyclisation of a compound of the formula:

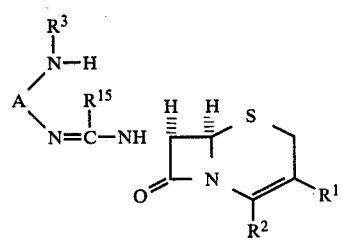   XVIII or a tautomer thereof, in which $R^{15}$ is a displaceable radical, for example a chlorine or bromine atom.

When the process of the invention manufactures the compound of the formula I in the form of the free acid or free base, or the zwitterion, and a salt is required, the compound of the formula I in the free acid or zwitterionic form is reacted with a base which affords a pharmaceutically-acceptable cation, or the compound of the formula I in the free base or zwitteronic form is reacted with an acid which affords a pharmaceutically acceptable anion. When the process of the invention manufactures the compound of the formula I in the form of an acid addition salt and the zwitteronic form is required, the compound of the formula I in the form of the acid addition salt is reacted with a low molecular weight epoxide such as epoxypropane.

The compound of the formula XI and, when $R^2$ is a carboxy radical, the esters (for example the diphenylmethyl, t-butyl, trimethylsilyl, benzyl, substituted benzyl and 2,2,2-trichloroethyl esters) thereof is a valuable intermediate for preparing many of the compounds of this invention. This compound is therefore provided as a further feature of the invention. It may be prepared by formylation of the compound of the formula XIII or an ester thereof, followed by reaction of the resulting formylamino compound with phosgene to give the corresponding isonitrile. This compound is then halogenated to give the compound of the formula XI. When $R^2$ is a carboxy radical additional protection and deprotection stages may be required. The preparation of the starting material of the formula XI is illustrated in Examples 1, 3, 5, 10 and 14.

Many of the compounds of the formula XII for use in process (b) are known compounds. Those which are new may be prepared, from known compounds, by standard chemical processes for preparing 1,2-diamines, for example as illustrated in Examples 10, 11, 26, 27, 34 and 36.

Many of the compounds of the formula XIII for use in process (c) are known compounds. Those which are new may be prepared, from known 7-aminocephalosporin derivatives, by standard chemical transformations known in the art of cephalosporin chemistry, for example as illustrated in Examples 5, 11, 12 and 29.

Many of the compounds of the formula XIV for use in process (c) are known compounds. Those which are new may be prepared by standard chemical transformations known in the art of imidazole and 2-imidazoline chemistry, for example as illustrated in Examples 30 and 35.

The starting materials for use in processes (e) and (f) may be prepared using one of the processes (a) to (d) inclusive of the invention.

The starting material for use in process (a) may be prepared using one of the processes (b) to (f) inclusive of the invention in which the acidic radical is in the protected form, for example as illustrated in Examples 1, 2, 3, 4, 5, 6, 7, 8, 9, 10, 11, 12, 13, 14, 15, 16, 17, 19, 20, 21, 22, 23, 25, 26, 27, 28, 32, 34, 36 and 38.

The starting material of the formula XVII for use in process (h) may be prepared by reaction of a compound of the formula:

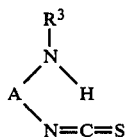

XIX optionally in a suitably protected form, with a compound of the formula XIII followed by reaction of the resulting thiourea with phosgene followed by triethylamine.

The starting material of the formula XVIII in which $R^{15}$ is a chlorine or bromine atom may be prepared by reaction of a compound of the formula XII, in which the nitrogen atom to which $R^3$ is attached also carries a protecting group, with a compound of the formula XI followed by removal of the protecting group from the product.

A particular value for $R^3$ is a hydrogen atom or a hydroxy, amino, methyl, ethyl, isopropyl, acetyl, methoxy, ethoxy, acetylamino, methylamino, ethylamino, isopropylamino, benzyl, 4-methoxybenzyl, phenyl or 4-methoxyphenyl radical.

A particular value for $R^4$ or $R^5$ is a hydrogen, fluorine, chlorine or bromine atom or a cyano, hydroxy, carboxy, 2-pyridyl, 3-pyridyl, 4-pyridyl, methyl, ethyl, n-propyl, i-propyl, n-butyl, aminomethyl, 1-aminoethyl, 2-aminoethyl, 1-aminopropyl, 2-aminopropyl, 3-aminopropyl, hydroxymethyl, 1-hydroxyethyl, 2-hydroxyethyl, 3-hydroxypropyl, methoxycarbonyl, ethoxycarbonyl, methylaminomethyl, 1-methylaminoethyl, 2-methylaminoethyl, ethylaminomethyl, 1-ethylaminoethyl, 2-ethylaminoethyl, dimethylaminomethyl, 1-dimethylaminoethyl, 2-dimethylaminoethyl, 3-dimethylaminopropyl, diethylaminomethyl, 1-diethylaminoethyl, 2-diethylaminoethyl, 3-diethylaminopropyl, phenyl, 2-, 3- or 4-fluorophenyl, 2-, 3- or 4-chlorophenyl, 2-, 3- or 4-bromophenyl, 2-, 3- or 4-nitrophenyl, 2-, 3- or 4-aminophenyl, 2-, 3- or 4-hydroxyphenyl, 2-, 3- or 4-carboxyphenyl, 2-, 3- or 4-cyanophenyl, 2-, 3- or 4-methylphenyl, 2-, 3- or 4-methoxycarbonylphenyl, 2,4-difluorophenyl, 3,4-difluorophenyl, 2,4-dichlorophenyl, 3,4-dichlorophenyl, 2,4-dibromophenyl, 3,4-dibromophenyl, 2,4-dinitrophenyl, 3,4-dinitrophenyl, 2,4-diaminophenyl, 3,4-diaminophenyl, 2,4-dihydroxyphenyl, 3,4-dihydroxyphenyl, 2,4-dicarboxyphenyl, 3,4-dicarboxyphenyl, 2,4-dicyanophenyl, 3,4-dicyanophenyl, 2,4-dimethylphenyl, 3,4-dimethylphenyl, 2,4-dimethoxycarbonylphenyl, 3,4-dimethoxycarbonylphenyl, 2-chloro-4-nitrophenyl, 2-nitro-4-chlorophenyl, 2-chloro-4-aminophenyl, 2-amino-4-chlorophenyl, 2-chloro-4-hydroxyphenyl, 2-hydroxy-4-chlorophenyl, 2-chloro-4-carboxyphenyl, 2-carboxy-4-chlorophenyl, 2-chloro-4-cyanophenyl, 2-cyano-4-chlorophenyl, 2-chloro-4-methylphenyl, 2-methyl-4-chlorophenyl, 2-chloro-4-methoxycarbonylphenyl, 2-methoxycarbonyl-4-chlorophenyl, 2-nitro-4-aminophenyl, 2-amino-4-nitrophenyl, 2-nitro-4-hydroxyphenyl, 2-hydroxy-4-nitrophenyl, 2-nitro-4-carboxyphenyl, 2-carboxy-4-nitrophenyl, 2-nitro-4-cyanophenyl, 2-cyano-4-nitrophenyl, 2-nitro-4-methylphenyl, 2-methyl-4-nitrophenyl, 2-nitro-4-methoxycarbonylphenyl, 2-methoxycarbonyl-4-nitrophenyl, 2-amino-4-hydroxyphenyl, 2-hydroxy-4-aminophenyl, 2-amino-4-carboxyphenyl, 2-carboxy-4-aminophenyl, 2-amino-4-cyanophenyl, 2-cyano-4-aminophenyl, 2-amino-4-methylphenyl, 2-methyl-4-aminophenyl, 2-amino-4-methoxycarbonylphenyl, 2-methoxycarbonyl-4-aminophenyl, 2-hydroxy-4-carboxyphenyl, 2-carboxy-4-hydroxyphenyl, 2-hydroxy-4-cyanophenyl, 2-cyano-4-hydroxyphenyl, 2-hydroxy-4-methylphenyl, 2-methyl-4-hydroxyphenyl, 2-hydroxy-4-methoxycarbonylphenyl, 2-methoxycarbonyl-4-hydroxyphenyl, 2-carboxy-4-cyanophenyl, 2-cyano-4-carboxyphenyl, 2-carboxy-4-methylphenyl, 2-methyl-4-carboxyphenyl, 2-carboxy-4-methoxycarbonylphenyl, 2-methoxycarbonyl-4-carboxyphenyl, 2-cyano-4-methylphenyl, 2-methyl-4-cyanophenyl, 2-methyl-4-methoxycarbonylphenyl or 2-methoxycarbonyl-4-methyl phenyl radical or $R^4$ and $R^5$ are joined to form, together with the nitrogen atoms to which they are attached, a cyclobutene, cyclopentene, cyclohexane, cyclohexene, cyclohexa-1,3-diene, cyclohexa-1,4-diene or benzene ring or a napthhalene or dihydroacenaphthalene ring system.

A particular value for the optional substituent on the aromatic part of the ring system formed by $R^4$ and $R^5$ being joined is 1, 2 or 3 radicals selected from fluorine, chlorine and bromine atoms and hydroxy, amino, cyano, carboxy, carbamoyl, nitro, ureido, methyl, ethyl, n-propyl, isopropyl, methoxy, ethoxy, isopropoxy, fluoromethyl, chloromethyl, trifluoromethyl, trichloromethyl, methylamino, ethylamino, hydroxymethyl, 1-hydroxyethyl, 2-hydroxyethyl, 3-hydroxypropyl, aminomethyl, 1-aminoethyl, 2-aminoethyl, 3-aminopropyl, acetylamino, propionylamino, azidomethyl, 2-azidoethyl, dimethylamino, diethylamino, and acetylaminomethyl methylaminomethyl, ethylaminomethyl, 1-methylaminoethyl, 2-methylaminoethyl, 1-ethylaminoethyl, 2-ethylaminoethyl, dimethylaminomethyl, diethylaminomethyl, 1-dimethylaminoethyl, 2-dimethylaminoethyl, 1-diethylaminoethyl, 2-diethylaminoethyl, cyanomethyl, 1-cyanoethyl, 2-cyanoethyl, carboxymethyl, 1-carboxyethyl, 2-carboxyethyl, carbamoylmethyl, 1-carbamoylethyl, 2-carbamoylethyl, ureidomethyl, 1-ureidoethyl, 2-ureidoethyl, a radical of the formula IV, a radical of the formula V in which n is 0 or 1 and m is 5, 6 or 7, a radical of the formula VI in which n is 0 or 1 and $R^{10}$, $R^{11}$, $R^{12}$ and $R^{13}$ are all hydrogen atoms or one or more of $R^{10}$, $R^{11}$, $R^{12}$ and $R^{13}$ are methyl radicals, a radical of the formula VII in which n is 0 or 1, a radical of the formula VIII in which n is 0 or 1 and a radical of the formula IX in which n is 0 or 1.

A particular value for $R^6$, $R^7$, $R^8$ or $R^9$ is a hydrogen atom or a cyano, carbamoyl, methoxycarbonyl, aminoethyl 2-pyridyl, 3-pyridyl, 4-pyridyl, acetyl, propionyl, hydroxymethyl, 1-hydroxyethyl, 2-hydroxyethyl, 3-hydroxypropyl, methyl, ethyl, n-propyl, i-propyl, n-butyl, n-hexyl, phenoxymethyl, 1-phenoxyethyl, 2-phenoxyethyl, (diphenylmethyl)phenoxymethyl, phenyl, 2-, 3- or 4-fluorophenyl, 2-, 3- or 4-chlorophenyl, 2-, 3- or 4-bromophenyl, 2-, 3- or 4-cyanophenyl, 2-, 3- or 4-aminophenyl, 2-, 3- or 4-carboxyphenyl, 2-, 3- or 4-carbamoylphenyl, 2-, 3- or 4-hydroxyphenyl, 3,4-dihydroxyphenyl, 2-, 3- or 4-phenylphenyl, 2-, 3- or 4-phenoxyphenyl, 2-, 3- or 4-diphenylmethylphenyl, 2-, 3- or 4-methylaminophenyl, 2-, 3- or 4-acetylaminophenyl, 2-, 3- or 4-methanesulphonylaminophenyl, 2-, 3- or 4-aminomethylphenyl, 2-, 3- or 4-(2-aminoethyl)phenyl, 2-, 3- or 4-hydroxymethylphenyl, 2-, 3- or 4-dimethylaminophenyl, 2-, 3- or 4-diethylaminophenyl, 2-, 3- or 4-methoxycarbonylphenyl, 2-, 3- or 4-ethoxycarbonylphenyl, 2-, 3- or 4-methylcarbamoylphenyl, 2-, 3- or 4-ethylcarbamoylphenyl, 2-, 3- or 4-dimethylcarbamoylphenyl, or 2-, 3- or 4-diethylcarbamoylphenyl radicals or $R^7$ and $R^8$, when in the cis relationship, are joined to form, together with the carbon atoms to which they are attached, a cyclopropane, cyclobutane, cyclobutene, cyclopentane, cyclopentene, cyclohexane, cyclohex-3-ene, cyclohex-4-ene, 3-phenylcyclopropane, 3,3-diphenylcyclopropane, 3-trifluoromethylcyclopropane, 3,3-di(trifluoromethyl)cyclopropane, 3-phenyl-3-trifluoromethylcyclopropane, 3-phenylcyclobutane, 3,3-diphenylcyclobutane, 3,4-diphenylcyclobutane, 3-trifluoromethylcyclobutane, 3,3-di(trifluoromethyl)cyclobutane, 3,4-di(trifluoromethyl)cyclobutane, 3-phenylcyclobut-3-ene, 3,4-diphenylcyclobut-3-ene, 3-trifluorocyclobut-3-ene, 3,4-di(trifluoro)cyclobut-3-ene, 3-phenylcyclohexane, 3,3-diphenylcyclohexane, 3,4-diphenylcyclohexane, 3-trifluorocyclohexane or 3,4-ditrifluorocyclohexane ring, or $R^6$ is a carboxy radical and $R^7$, $R^8$ and $R^9$ are hydrogen atoms.

The characterising feature of the present invention is the nature of the 7β-substituent on the cephalosporin nucleus. $R^1$ may thus be a hydrogen or halogen atom (e.g. fluorine, chlorine or bromine), a hydroxy or amino radical or a saturated or unsaturated, substituted or unsubstituted organic group containing 1 to 20 carbon atoms. Illustrative examples of $R^1$ when it is an organic group of 1 to 20 carbon atoms are as follows:

(a) alkyl radicals of 1 to 6 carbon atoms (e.g. methyl, ethyl, n-propyl, i-propyl, n-butyl), benzyl optionally substituted by fluorine or methoxy, haloalkyl radicals of 1 to 6 carbon atoms (e.g. $CH_2F$, $CH_2Cl$, $CH_2Br$, $CHF_2$, $CF_3$), formyl, carboxy, alkoxy radicals of 1 to 6 carbon atoms (e.g. methoxy), methylthio radicals of 1 to 6 carbon atoms, alkylamino radicals of 1 to 6 carbon atoms (e.g. methylamino, ethylamino), phenylamino, benzylamino, cycloalkylamino radicals of 3 to 6 carbon atoms (e.g. cyclohexylamino), cyano, alkoxycarbonyl radicals of 2 to 6 carbon atoms (e.g. methoxycarbonyl), alkanoyl radicals of 2 to 6 carbon atoms (e.g. acetyl), alkoxycarbonylalkyl radicals of 3 to 10 carbon atoms (e.g. methoxycarbonylmethyl), alkoxycarbonylamino radicals of 2 to 6 carbon atoms (e.g. methoxycarbonylamino), alkylthiocarbonylamino radicals of 2 to 6 carbon atoms (e.g. methylthiocarbonylamino), piperidino, pyrrolidino, morpholino, alkanoylamino radicals of 2 to 6 carbon atoms (e.g. acetylamino), ureido, alkylureido radicals of 2 to 6 carbon atoms (e.g. 3-methylureido), dialkylureido radicals of 3 to 8 carbon atoms (e.g. 3,3-dimethylureido), alkanesulphinyl radicals of 1 to 6 carbon atoms (e.g. methanesulphinyl), alkanesulphonyl radicals of 1 to 6 carbon atoms (e.g. methanesulphonyl), heterocyclyl or heterocyclylthio radicals in which the heterocycle is a 1,3,4-thiadiazol-2-yl or 1,3,4-oxadiazol-2-yl, each optionally substituted in the 5-position, a 1H-tetrazol-5-yl optionally substituted in the 1-position, or a 1H-1,2,3-triazol-4-yl radical optionally substituted in the 1 or 5 position, the optional substituents in each of these heterocycles being an alkyl radical of 1 to 6 carbon atoms (e.g. methyl, ethyl, i-propyl), sulphoalkyl radical of 1 to 6 carbon atoms (e.g. 2-sulphoethyl), a carboxyalkyl radical of 2 to 6 carbon atoms (e.g. 2-carboxyethyl), a haloalkyl radical of 1 to 6 carbon atoms (e.g. 2,2,2-trifluoroethyl), or an alkylthioalkyl radical of 3 to 6 carbon atoms (e.g. 2-methylthioethyl) or a pyridazin-3-yl, oxazol-3-yl or thiazol-3-yl radical each optionally substituted by 1 or 2 radicals selected from alkyl radicals of 1 to 6 carbon atoms (e.g. methyl), haloalkyl radicals of 1 to 6 carbon atoms (e.g. trifluoromethyl) and alkoxycarbonyl radicals of 2 to 6 carbon atoms (e.g. methoxycarbonyl);

(b) radicals of the formula:

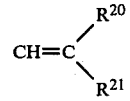

XX in which $R^{20}$ and $R^{21}$, which may be the same or different, are hydrogen atoms, alkyl radicals of 1 to 6 carbon atoms (e.g. methyl, ethyl, isopropyl, n-butyl), cycloaliphatic radicals of 5 to 7 carbon atoms (e.g. cyclopentyl, cyclohexyl), aryl radicals of 6 to 12 carbon atoms (e.g. phenyl, nitrophenyl), arylalkyl radicals of 7 to 10 carbon atoms (e.g. benzyl, 2-phenethyl), formyl, cyano, carboxy, alkoxycarbonyl of 2 to 6 carbon atoms (e.g. methoxycarbonyl, ethoxycarbonyl), sulpho, alkanesulphinyl radicals of 1 to 6 carbon atoms (e.g. methanesulphinyl), alkanesulphonyl radicals of 1 to 6 carbon atoms (e.g. methanesulphonyl), alkoxy radicals of 1 to 6 carbon atoms (e.g. methoxy), alkylthio radicals of 1 to 6 carbon atoms (e.g. methylthio), carbamoyl, nitro, hydroxyalkyl radicals of 1 to 6 carbon atoms (e.g. hydroxymethyl), methylcarbamoyloxymethyl, benzylcarbamoyloxymethyl, alkoxymethyl radicals of 2 to 6 carbon atoms (e.g. methoxymethyl), alkylthiomethyl radicals of 2 to 6 carbon atoms (e.g. methylthiomethyl), 2-haloethoxymethyl, cyclopentyloxymethyl, benzyloxymethyl, alkanoyloxymethyl radicals of 3 to 8 carbon atoms (e.g. acetoxymethyl) and radicals of the formula CH$_2$SHet$^1$ in which Het$^1$ is a 1,3,4-thiadiazol-2-yl or 1,3,4-oxadiazol-2-yl, both optionally substituted in the 5-position by a methyl radical, a 1H-triazol-5-yl radical optionally substituted in the 1-position by a methyl radical or a 1H-1,2,3-triazol-4-yl radical;

(c) a radical of the formula:

XXI in which R$^{22}$ is a cyano, carboxy or alkoxycarbonyl radical of 2 to 6 carbon atoms (e.g. methoxycarbonyl);

(d) a radical of the formula:

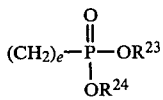

XXII in which R$^{23}$ and R$^{24}$, which may be the same or different, are hydrogen atoms or alkyl radicals of 1 to 6 carbon atoms (e.g. methyl) and e is 1 to 4;

(e) radicals of the formula CH$_2$Y in which Y is an atom or group which is the residue of a nucleophile or a derivative of a residue of a nucleophile. Y may thus, for example, be derived from nucleophilic substances characterised by possessing a nucleophilic nitrogen, carbon, sulphur or oxygen atom described in patents and scientific literature pertaining to cephalosporin chemistry. Examples of such nucleophiles include:

(I) NITROGEN NUCLEOPHILES

Examples of nitrogen nucleophiles include:
(i) trialkylamines of 3 to 15 carbon atoms (e.g. triethylamine)
(ii) heterocyclic amines having more than one heteroatom, at least heteroatom being nitrogen, (e.g. pyrimidines, purines, pyridazines, pyrazines, pyrazoles, imidazoles, triazoles, thiazoles)
(iii) pyridines which are optionally substituted by 1 to 5, preferably 1 to 3, substituents selected from halogen atoms (e.g. F, Cl, Br), alkyl radicals of 1 to 6 carbon atoms (e.g. methyl, ethyl, n-propyl, isopropyl, n-butyl), aryl radicals of 6 to 10 carbon atoms (e.g. phenyl), arylalkyl radicals of 7 to 11 carbon atoms (e.g. benzyl, 2-phenethyl), alkoxyalkyl radicals of 2 to 10 carbon atoms (e.g. methoxymethyl, ethoxymethyl), alkanoyloxymethyl radicals of 3 to 10 carbon atoms (e.g. acetoxymethyl), formyl radicals, carbamoyl radicals, alkanoyloxy radicals of 2 to 6 carbon atoms (e.g. acetoxymethyl), alkoxycarbonyl radicals of 2 to 6 carbon atoms (e.g. methoxycarbonyl, ethoxycarbonyl), alkoxy radicals of 1 to 6 carbon atoms (e.g. methoxy, ethoxy, n-propoxy, isopropoxy), aryloxy radicals of 6 to 10 carbon atoms (e.g. phenoxy), aralkoxy radicals of 7 to 11 carbon atoms (e.g. benzyloxy), alkylthio radicals of 1 to 6 carbon atoms (e.g. methylthio, ethylthio), arylthio radicals of 6 to 10 carbon atoms (e.g. phenylthio), aralkylthio radicals of 7 to 11 carbon atoms (e.g. phenylthio), cyano, hydroxy, alkylcarbamoyl radicals of 2 to 6 carbon atoms (e.g. methylcarbamoyl, ethylcarbamoyl), dialkylcarbamoyl radicals of 3 to 10 carbon atoms, (e.g. dimethylcarbamoyl, diethylcarbamoyl), (hydroxyalkyl)carbamoyl radicals of 2 to 6 carbon atoms (e.g. (hydroxymethyl)carbamoyl, (2-hydroxyethyl)carbamoyl) and carbamoylalkyl radicals of 2 to 6 carbon atoms (e.g. carbamoylmethyl, 2-carbamoylethyl);

(iv) azide radicals;
(v) amino, alkanoylamino radicals of 1 to 6 carbon atoms (e.g. acetylamino) and aroylamino radicals of 7 to 11 carbon atoms (e.g. benzoylamino);

(II) CARBON NUCLEOPHILES

Examples of carbon nucelophiles include:
cyanide, pyrroles and substituted pyrroles, (e.g. indoles, furan, thiophene and pyridine each optionally substituted by methoxycarbonyl) and compounds giving stabilised carbanions (e.g. acetoacetic and malonic esters and cyclohexane-1,3-diones or enamines, ynamines or enols). Such a carbon nucleophile may give rise to R$^1$ having the formula:

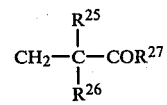

XXIII in which R$^{25}$ and R$^{26}$, which may be the same or different, are selected from hydrogen atoms and cyano, alkyl radicals of 1 to 6 carbon atoms (e.g. methyl, ethyl), alkoxycarbonyl radicals of 2 to 6 carbon atoms (e.g. methoxycarbonyl, ethoxycarbonyl), mono- or di-arylalkoxycarbonyl radicals of 8 to 20 carbon atoms, (e.g. benzyloxycarbonyl), alkanoyl radicals of 2 to 6 carbon atoms (e.g. acetyl), aralkyl radicals of 7 to 11 carbon atoms (e.g. benzyl), cyclopentyl and cyclohexyl radicals and phenyl radicals optionally substituted by 1 or 2 radicals selected from halogen atoms and alkyl, alkoxy and alkylamino radicals of 1 to 6 carbon atoms (e.g. methyl, ethyl, methoxy, ethoxy, methylamino, ethylamino), nitro and amino radicals, and R$^{27}$ is selected from hydrogen, alkyl radicals of 1 to 6 carbon atoms (e.g. methyl, ethyl), aralkyl radicals of 7 to 11 carbon atoms (e.g. benzyl), cyclopentyl and cyclohexyl radicals, and phenyl radicals optionally substituted by 1 or 2 radicals selected from halogen atoms, alkyl, alkoxy and alkylamino radicals of 1 to 6 carbon atoms (e.g. methyl, ethyl, methoxy, ethoxy, methylamino, ethylamino).

(III) SULPHUR NUCLEOPHILES

Examples of sulphur nucleophiles include:
thiourea optionally substituted by an alkyl radical of 1 to 6 carbon atoms (e.g. methyl, ethyl), an aryl radical of 6 to 10 carbon atoms (e.g. phenyl), an alicyclic radical of 5 to 7 carbon atoms (cyclopentyl, cyclohexyl) or a heterocyclic radical (e.g. pyridine, pyrimidine, thiazole, thiadiazole), dithiocarbamates, thioamides substituted by an alkyl radical of 1 to 6 carbon atoms (e.g. thioacetamide) or by an aryl radical of 6 to 10 carbon atoms (e.g. thiobenzamide), thiosemicarbazides, thiosulphates, alkylthiols of 1 to 6 carbon atoms (e.g. ethanethiol, n-propanethiol, n-butanethiol), arylthiols of 6 to 10 carbon atoms optionally substituted by a carboxy radical (e.g. thiophenol, 2-carboxythiophenol) arylthioacids or heterocyclicthioacids of up to 10 carbon atoms (e.g. thiobenzoic or thiopicolinic acid) and dithioacids, particularly of the formula:

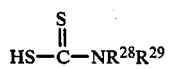

$$\text{HS}-\overset{\overset{\text{S}}{\|}}{\text{C}}-\text{NR}^{28}\text{R}^{29} \qquad \text{XXIV}$$

in which $R^{28}$ and $R^{29}$, which may be the same or different, are hydrogen atoms, alkyl radicals of 1 to 6 carbon atoms (e.g. methyl, ethyl, n-propyl, i-propyl), hydroxyalkyl radicals of 2 to 6 carbon atoms (e.g. 2-hydroxyethyl), alkylaminoalkyl radicals of 3 to 8 carbon atoms (e.g. 2-methylaminoethyl), dialkylaminoalkyl radicals of 4 to 10 carbon atoms (e.g. 2-dimethylaminoethyl) or phenyl radicals or $R^{28}$ and $R^{29}$ are joined to form a pyrrolidine, piperidine or morpholine ring or a piperazine ring which is optionally substituted on the nitrogen atom by one or two (in quaternised form) radicals selected from alkyl of 1 to 6 carbon atoms (e.g. methyl, ethyl, n-propyl, n-hexyl) and alkenyl radicals of 3 to 6 carbon atoms (e.g. allyl).

A preferred class of sulphur nucleophile includes compounds of the formula $R^{30}S(O)_mH$ in which m is 0, 1 or 2 and $R^{30}$ is an alkyl radical of 1 to 6 carbon atoms, (e.g. methyl, ethyl, n-propyl, isopropyl, n-butyl), an alicyclic radical of 5 to 7 carbon atoms (e.g. cyclopentyl, cyclohexyl), an aryl radical of 6 to 10 carbon atoms optionally substituted by a carboxy radical (e.g. phenyl, 2-carboxyphenyl, naphthyl), an arylalkyl radical of 7 to 11 carbon atoms (e.g. benzyl, 2-phenethyl) or a 5- or 6-membered heterocyclic ring (partially or fully unsaturated) containing 1 to 4 nitrogen atoms which ring may further include (where possible) oxygen and/or sulphur atoms, in which the nitrogen atom or atoms may be in the oxide form, which heterocyclic ring may be fused with another heterocyclic ring within the same definition or may be fused with a benzene ring, the above aryl, arylalkyl, heterocyclic or fused benzene ring being optionally substituted (where possible) by 1 or 2 substituents selected from alkyl radicals of 1 to 6 carbon atoms (e.g methyl, ethyl, n-propyl, i-propyl, n-butyl), haloalkyl radicals of 1 to 6 carbon atoms (e.g. trifluoromethyl, 2,2,2-trifluoroethyl), aryl radicals of 6 to 10 carbon atoms (e.g. phenyl, naphthyl), alkenyl radicals of 2 to 6 carbon atoms (e.g. vinyl, allyl), alkoxy radicals of 1 to 6 carbon atoms (e.g. methoxy, ethoxy, n-propoxy, i-propoxy, 2-butoxy), halogen atoms (e.g. chlorine, bromine), oxo, hydroxy, mercapto, amino, carboxy, cyano, isothiocyanato, carbamoyl, sulphamoyl, alkoxycarbonyl radicals of 2 to 6 carbon atoms (e.g. methoxycarbonyl), alkenyloxycarbonyl radicals of 3 to 6 carbon atoms (e.g. allyloxycarbonyl), aralkylcarbonyl radicals 8 to 12 carbon atoms (e.g. benzyloxycarbonyl), aryloxycarbonyl radicals of 7 to 11 carbon atoms (e.g. phenoxycarbonyl), hydroxyalkyl radicals of 2 to 6 carbon atoms (e.g. 2-hydroxyethyl radicals), dihydroxyalkyl radicals of 3 to 6 carbon atoms (e.g. 2,3-dihydroxypropyl), sulphoamino radicals and alkenesulphonylamino radicals of 1 to 6 carbon atoms (e.g. methanesulphonylamino) and radicals of the formula B—$R^{31}$ in which B is a straight or branched chain of 2 to 8 carbon atoms which may be interrupted by a sulphur or oxygen atom or by an NH or N-alkyl radical of 1 to 6 carbon atoms (e.g. N-methyl) and $R^{31}$ is a radical selected from hydroxy, mercapto, cyano, alkylamino radicals of 1 to 6 carbon atoms (e.g. methylamino, ethylamino), dialkylamino radicals of 2 to 6 carbon atoms (e.g. dimethylamino, diethylamino), alkanoylamino radicals of 2 to 6 carbon atoms (e.g. acetylamino), carboxy, sulpho, carbamoyl, sulphamoyl, amidino, guanidino, alkoxycarbonyl radicals of 2 to 6 carbon atoms (e.g. methoxycarbonyl, ethoxycarbonyl), alkylcarbamoyl radicals of 2 to 6 carbon atoms (e.g. methylcarbamoyl, ethylcarbamoyl), dialkylcarbamoyl radicals of 2 to 6 carbon atoms (e.g. dimethylcarbamoyl, diethylcarbamoyl) alkylsulphamoyl radicals of 1 to 6 carbon atoms (e.g. methylsulphamoyl, ethylsulphamoyl), dialkylsulphamoyl radicals of 2 to 6 carbon atoms (e.g. dimethylsulphamoyl, diethylsulphamoyl radicals), sulphoamino, ureido, alkoxy radicals of 1 to 6 carbon atoms (e.g. methoxy, ethyl, n-propoxy), alkylthio radicals of 1 to 6 carbon atoms (e.g. methylthio, ethylthio), alkanesulphonyl radicals of 1 to 6 carbon atoms (e.g. methanesulphonyl), alkanoyl radicals of 2 to 6 carbon atoms (e.g. acetyl, n-propionyl) and alkanoyloxy radicals of 2 to 6 carbon atoms (e.g. acetoxy, n-propionyloxy), and radicals of the formula —S—$R^{32}$ in which $R^{32}$ is an alkyl radical of 1 to 6 carbon atoms (e.g. methyl, ethyl, n-propyl, i-propyl, n-butyl) or a group of the formula B—$R^{31}$ in which B and $R^{31}$ have the meanings given above and radicals of the formula $NR^{33}R^{34}$ in which $R^{33}$ and $R^{34}$, which may be the same or different, are selected from alkyl radicals of 1 to 6 carbon atoms (e.g. methyl, ethyl, n-propyl, isopropyl), groups of the formula B—$R^{31}$ in which B and $R^{31}$ have the definitions given above, alkoxycarbonyl radicals of 1 to 6 carbon atoms (e.g. methoxycarbonyl), alkanoyl radicals of 2 to 6 carbon atoms (e.g. acetyl), carbamoyl, alkylcarbamoyl radicals of 2 to 6 carbon atoms (methylcarbamoyl) and dialkylcarbamoyl radicals of 3 to 10 carbon atoms (e.g. dimethylcarbamoyl).

A particular value for $R^{30}$ when it is a heterocyclic ring or fused heterocyclic ring system is a pyridyl, N-oxopyridyl, pyrimidyl, pyridazinyl, N-oxo-pyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazinyl, 1,2,3-triazinyl, 1,2,4-triazolyl, 1H-tetrazolyl, 2H-tetrazolyl, tetrazolopyridazinyl, tetrazolopyrimidyl, tetrazolopyrazinyl, tetrazolotriazinyl, triazolopyridazinyl, triazolopyridinyl, triazolopyrimidinyl, triazolopyrazinyl, imidazopyridazinyl, pyrrolopyridazinyl, tetrazolopyridyl, furopyridazinyl, thiazolopyridazinyl, thiadiazolopyridazinyl, thienopyridazinyl or thienopyrimidinyl ring.

A particularly preferred class of sulphur nucleophiles is that of the formula $R^{30}$—$S(O)_mH$ in which m is zero.

(IV) OXYGEN NUCLEOPHILES

Examples of oxygen nucleophiles include:

(i) those of the formula $R^{35}$—OH in which $R^{35}$ is a hydrogen atom, an alkyl radical of 1 to 6 carbon atoms (e.g. methyl, ethyl, n-propyl, isopropyl, n-butyl), an alkenyl radical of 3 to 6 carbon atoms (e.g. allyl), an alkynyl radical of 3 to 6 carbon atoms (e.g. propargyl), a cycloalkyl radical of 5 to 7 carbon atoms (e.g. cyclopentyl, cyclohexyl), a cycloalkylalkyl radical of 6 to 12 carbon atoms (e.g. cyclopentylmethyl, 2-cyclohexylethyl), an aryl radical of 6 to 10 carbon atoms (e.g. phenyl, naphthyl), an arylalkyl radical of 7 to 11 carbon atoms (e.g. benzyl) or a furfuryl radical, any of which may be substituted by 1 or 2 radicals selected from halogen atoms (e.g. fluorine, chlorine, bromine, iodine), alkyl radicals of 1 to 6 carbon atoms (e.g. methyl, ethyl), nitro, hydroxy, carboxy, alkanoyloxy radicals of 2 to 6 carbon atoms (e.g. acetoxy), alkoxcarbonyl radicals of 2 to 6 carbon atoms (e.g. methoxycarbonyl), alkanoyl radicals of 2 to 6 carbon atoms (e.g. acetyl), alkanesulphonyl radicals of 1 to 6 carbon atoms (e.g. methanesulphonyl), alkoxysulphonyl radicals of 1 to 6 carbon atoms (e.g. methoxysulphonyl), amino, alkylamino radicals of 1 to 6 carbon atoms (e.g. methylamino), alkanoylamino radicals of 2 to 6 carbon atoms (e.g. acetylamino), or $R^{35}$ is a carbamoyl radical;

(iii) those of the formula $R^{36}$—Q—COOH in which Q is a direct bond, an oxygen or sulphur atom or an NH radical and $R^{36}$ is:

(a) a hydrogen atom, an alkyl radical of 1 to 6 carbon atoms (e.g. a methyl, ethyl, n-propyl, isopropyl, n-butyl, t-butyl or sec-butyl) which may be interrupted by an oxygen or sulphur atom or by an NH group or substituted by a cyano, carboxy, methoxycarbonyl, ethoxycarbonyl, hydroxy, carboxycarbonyl, halogen (e.g. chlorine, bromine, iodine) or amino radical;

(b) an alkenyl radical of 2 to 6 carbon atoms (e.g. vinyl, allyl) which may be interrupted by an oxygen or sulphur atom or an NH group;

(c) a phenyl, hydroxyphenyl, chlorophenyl, fluorophenyl, tolyl, nitrophenyl, aminophenyl, methoxyphenyl, methylthiophenyl, thienyl, pyridyl, cyclohexyl, cyclopentyl, sydnonyl, naphthyl or ethoxynaphthyl radical; or (d) $R^{37}$—$(CH_2)_q$ where $R^{37}$ has the value for $R^{36}$ listed in (a) above and q is 1 to 4.

A particular value for $R^2$ is a carboxy radical, a radical of the formula:

| | |
|---|---|
| $COOCHR^{38}OCOR^{39}$ | XXV |
| $COOCHR^{38}SCOR^{39}$ | XXVI |
| $COOCHR^{38}COR^{39}$ | XXVII |
| $COOCHR^{38}OR^{39}$ | XXVIII |
| $COOCOOR^{39}$ | XXIX |
| $COOCHR^{38}OCOOR^{39}$ | XXX |

   XXXI

| | |
|---|---|
| $COOCHR^{38}OCH_2CH_2OCH_3$ | XXXII |
| $COOCH_2OCO(CH_2)_t$—$CHR^{40}$—$NH_2$ | XXXIII |

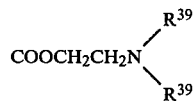   XXXIV

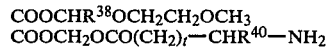   XXXV

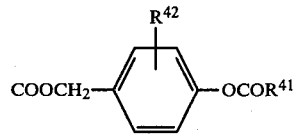   XXXVI in which $R^{38}$ is a hydrogen atom or an alkyl radical of 1 to 6 carbon atoms (e.g. methyl); $R^{39}$ is an alkyl radical of 1 to 6 carbon atoms (e.g. methyl, ethyl, n-propyl, i-propyl, n-butyl, t-butyl), $R^{40}$ is a hydrogen atom, an alkyl radical of 1 to 6 carbon atoms (e.g. methyl, ethyl, n-propyl, i-propyl, i-butyl, s-butyl), an arylalkyl radical of 7 to 11 carbon atoms (e.g. benzyl) or an alkoxycarbonyl radical of 2 to 6 carbon atoms (e.g. methoxycarbonyl), t is 0 or 1, $R^{41}$ is an alkyl radical of 1 to 6 carbon atoms (e.g. methyl, ethyl), an aryl radical of 6 to 10 carbon atoms (e.g. phenyl) or an aralkyl radical of 7 to 11 carbon atoms (e.g. benzyl), $R^{42}$ is a hydrogen atom or one, two or three radicals selected from halogen atoms (e.g. Cl, Br) and nitro, cyano, alkyl, alkoxy, alkylthio, alkylsulphinyl and alkanesulphonyl radicals each of 1 to 6 carbon atoms (e.g. methyl, methoxy, methylthio, methylsulphinyl, methylsulphonyl), alkoxycarbonyl, alkoxythiocarbonyl and acylamino radicals each of 2 to 6 carbon atoms (e.g. methoxycarbonyl, methylthiocarbonyl, acetylamino), aryl, aryloxy, arylthio, arylsulphinyl and arylsulphonyl radicals each of 6 to 10 carbon atoms (e.g. phenyl, phenoxy, phenylthio, phenylsulphinyl, phenylsulphonyl) and aryloxycarbonyl, arylthiocarbonyl and aryloxythiocarbonyl radicals each of 7 to 11 carbon atoms (e.g. phenoxycarbonyl, phenylthiocarbonyl, phenoxythiocarbonyl), $R^{43}$ is a hydrogen atom or one of the values for $R^{41}$ given above and $R^{44}$ is a hydrogen atom or one, two or three radicals selected from halogen atoms (e.g. Cl, Br), and alkyl and alkoxy radicals each of 1 to 6 carbon atoms (e.g. methyl, methoxy), or $R^2$ is a tetrazol-5-yl radical.

The following are 14 preferred features of the cephalosporin derivative of the formula I. When any one of these features is taken, either singly or in combination, with the other general features of the cephalosporin derivative of the formula I listed above, there are obtained preferred sub-groups of compounds within the above general definition.

1. $R^2$ is a carboxy radical or the acetoxymethyl or pivaloyloxymethyl ester thereof.

2.

is a radical of the formula II in which $R^4$ and $R^5$ are joined to form an optionally-substituted aromatic ring system.

3.

is a radical of the formula II in which $R^4$ and $R^5$ are hydrogen atoms or cyano, hydroxy, carboxy, pyridyl, alkyl, aminoalkyl, hydroxyalkyl, alkoxycarbonyl, alkylaminoalkyl, dialkylaminoalkyl or optionally substituted phenyl radicals or $R^4$ and $R^5$ are joined to form a nonaromatic ring system.

4.

is a radical of the formula III.

5. $R^1$ is a radical of the formula $CH_2Y$ in which Y is derived from an oxygen nucleophile.

6. $R^1$ is a radical of the formula $CH_2Y$ in which Y is derived from a sulphur nucleophile.

7.

$$A\genfrac{}{}{0pt}{}{\diagup}{\diagdown}$$

is a radical of the formula II in which $R^4$ and $R^5$ are joined to form a benzene ring which is optionally substituted in the 5-position (benzimidazole numbering) by a hydroxy radical or aminoalkyl radical of 1 to 6 carbon atoms or by a radical of the formula V, VI, VII, VIII or IX;

8.

$$A\genfrac{}{}{0pt}{}{\diagup}{\diagdown}$$

is a radical of the formula II in which $R^4$ is a hydrogen atom, an alkyl radical of 1 to 6 carbon atoms, a hydroxyalkyl radical of 1 to 6 carbon atoms or an aminoalkyl radical of 1 to 6 carbon atoms and $R^5$ is a hydrogen atom or $R^4$ and $R^5$ are both alkyl radicals of 1 to 6 carbon atoms.

9.

$$A\genfrac{}{}{0pt}{}{\diagup}{\diagdown}$$

is a radical of the formula III in which $R^6$ and $R^9$ are hydrogen atoms.

10.

$$A\genfrac{}{}{0pt}{}{\diagup}{\diagdown}$$

is a radical of the formula III in which $R^6$ and $R^9$ are hydrogen atoms and $R^7$ and $R^8$ are joined to form a cyclopropane ring.

11.

$$A\genfrac{}{}{0pt}{}{\diagup}{\diagdown}$$

is a radical of the formula III in which $R^6$, $R^8$ and $R^9$ are hydrogen atoms and $R^7$ is a phenyl radical optionally substituted by an amino or cyano radical, an alkylamino radical of 1 to 6 carbon atoms or a dialkylamino radical of 2 to 10 carbon atoms.

12. $R^1$ is a 1H-tetrazol-5-ylthiomethyl, 1,3,4-thiadiazol-2-ylthiomethyl, 1,2,3-thiadiazol-5-yl or a 1H-1,2,3-triazol-5-yl thiomethyl radical in which the heterocyclic ring carries a single optional substituent.

13. $R^1$ is a hydrogen or chlorine atom, or a methoxy, acetoxymethyl, carbamoyloxymethyl, pyridiniummethyl, (4-carbamoyl)pyridiniummethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 4-methyl-5-carboxymethylthiazol-2-ylthiomethyl, 1H-1,2,3-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-hydroxy-2-methyl-5-oxo-2H-1,2,4-triazin-3-yl)thiomethyl (6-hydroxy-4-methyl-5-oxo-2H-1,2,4-triazin-3-yl)thiomethyl, (6-carboxymethyl, 7-hydroxypyrrolo[1,2-b]pyridazin-2-yl)thiomethyl or 1,2,3-thiadiazol-5-ylthiomethyl radical.

14. $R^3$ is a hydrogen atom.

Particular compounds of the invention are described in the Examples. The following is a group of preferred compounds:

3-acetoxymethyl-7-(5-hydroxybenzimidazolyl-2-yl)aminoceph-3-em-4-carboxylic acid;
3-acetoxymethyl-7-(5-aminomethylbenzimidazol-2-yl)aminoceph-3-em-4-carboxylic acid;
7-(5-hydroxybenzimidazol-2-yl)amino-3-(1-methyl-1H-tetrazol-5-yl)thiomethylceph-3-em-4-carboxylic acid;
3-[1-(2-dimethylamino)ethyl-1H-tetrazol-5-yl]thiomethyl-7-imidazol-2-ylaminoceph-3-em-4-carboxylic acid;
3-(1-methyl-1H-tetrazol-5-yl)thiomethyl-7-imidazol-2-ylaminoceph-3-em-4-carboxylic acid;
3-(5-methyl-1,3,4-thiadiazol-2-yl)thiomethyl-7-(imidazol-2-yl)aminoceph-3-em-4-carboxylic acid;
3-(1H-1,2,3-triazol-4-yl)thiomethyl-7-(imidazol-2-yl)aminoceph-3-em-4-carboxylic acid;
3-(1-carboxymethyl-1H-tetrazol-5-yl)thiomethyl-7-(imidazol-2-yl)aminoceph-3-em-4-carboxylic acid;
7-(imidazol-2-yl)amino-3-(1,3,4-thiadiazol-2-yl)thiomethylceph-3-em-4-carboxylic acid;
7-imidazol-2-yl)amino-3-(1-methyl-1H-tetrazol-5-yl)thiomethylceph-3-em-4-carboxylic acid;
7-(imidazol-2-yl)amino-3-(1-sulphomethyl-1H-tetrazol-5-yl)thiomethylceph-3-em-4-carboxylic acid;
7-(imidazol-2-yl)amino-3-(1-isopropyl-1H-tetrazol-5-yl)thiomethylceph-3-em-4-carboxylic acid;
7-(imidazol-2-yl)amino-3-[1-(2,2,2-trifluoro)ethyl-1H-tetrazol-5-yl]thiomethylceph-3-em-4-carboxylic acid;
7-(imidazol-2-yl)amino-3-[1-(2-methylthio)ethyl-1H-tetrazol-5-yl]thiomethylceph-3-em-4-carboxylic acid;
7-(imidazol-2-yl)amino-3-(5-trifluoromethyl-1H-1,2,4-triazol-3-yl)thiomethylceph-3-em-4-carboxylic acid;
7-(4-methylimidazol-2-yl)amino-3-(5-methyl-1,3,4-thiadiazol-2-yl)thiomethylceph-3-em-4-carboxylic acid;
7-(4-methylimidazol-2-yl)amino-3-(1H-1,2,3-triazol-4-yl)thiomethylceph-3-em-4-carboxylic acid;
7-(4,5-dimethylimidazol-2-yl)amino-3-(5-methyl-1,3,4-thiadiazol-2-yl)thiomethylceph-3-em-4-carboxylic acid;
3-acetoxymethyl-7-(4-hydroxymethylimidazol-2-yl)aminoceph-3-em-4-carboxylic acid;
7-(2-imidazolin-2-yl)amino-3-methylceph-3-em-4-carboxylic acid;
7-(4-phenyl-2-imidazolin-2-yl)amino-3-methylceph-3-em-4-carboxylic acid;
7-[4-(4-cyano)phenyl-2-imidazolin-2-yl]amino-3-methylceph-3-em-4-carboxylic acid;

7-[4-(4-dimethylamino)phenyl-2-imidazolin-2-yl]amino-3-methylceph-3-em-4-carboxylic acid;
7-(2,4-diazabicyclo[3,1,0]hex-2-en-3-yl)amino-3-methylceph-3-em-4-carboxylic acid;
7-(2,4-diazabicyclo[3,1,0]hex-2-en-3-yl)amino-3-(5-methyl-1,3,4-thiadiazol-2-yl)thiomethylceph-3-em-4-carboxylic acid; and
7-(2,4-diazabicyclo[3,1,0]hex-2-en-3-yl)amino-3-(1-methyl-1H-tetrazol-5-yl)thiomethylceph-3-em-4-carboxylic acid;
and the pharmaceutically-acceptable acid-addition salts and base-addition salts thereof.

A suitable acid-addition salt of the cephalosporin derivative of the invention is, for example, a salt formed with hydrochloric, hydrobromic, phosphoric, sulphuric, citric or maleic acid. A suitable base-addition salt of the cephalosporin derivative of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N$^1$-dibenzylethylenediamine, and other amines which have been used to form salts with cephalosporins).

As noted above the cephalosporin derivatives of the invention have antibacterial properties. Thus they are useful antibacterial agents, many of them having a broad spectrum of activity in vitro, against standard laboratory microorganisms, both Gram-negative and Gram-positive, which are used to screen for activity against pathogenic bacteria. The antibacterial spectrum and potency of a particular compound may be determined in a standard test system. The results set out in the following Table are illustrative of the biological activity displayed by the three chemical sub-types (imidazoles, benzimidazoles and 2-imidazolines) contained in this patent application on such an in vitro test system. The antibacterial activity is described in terms of the minimum inhibitory concentration (MIC) determined by agar-dilution technique with an inoculum size of $\sim 10^5$ CFU.

The antibacterial properties of the compounds of the invention may also be demonstrated in conventional mouse protection tests.

The following compounds were administered subcutaneously to mice in two single doses over 1 day, each dose being at least ten times the minimum effective dose which protected 50% of the mice against bacterial infection (PD$_{50}$):

7-(imidazol-2-yl)amino-3-(1H-1-methyltetrazol-5-yl)thiomethylceph-3-em-4-carboxylic acid (dose 100 mg./kg.);

3-acetoxymethyl-7-imidazol-2-yl)aminoceph-3-em-4-carboxylic acid (dose 100 mg./kg.);

3-acetoxymethyl-7-(4-hydroxybenzimidazol-2-yl)aminoceph-3-em-4-carboxylic acid (dose 200 mg./kg.);

3-acetoxymethyl-7-[4-(4-dimethylamino)-phenylimidazol-2-yl]aminoceph-3-em-4-carboxylic acid (dose 100 mg./kg.);

no overt toxic symptons or side effects were noted. Similarly the compound 7-(imidazol-2-yl)amino-3-(2-methyl-1,3,4-thiadiazol-5-yl)thiomethylceph-3-em-4-carboxylic acid was administered both orally and subcutaneously to mice at a single dose of 2 g./kg. Again no overt toxic symptoms or side effects were noted.

According to a further feature of the invention there is provided a pharmaceutical composition which comprises a cephalosporin derivative of the invention in association with a non-toxic pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one

TABLE

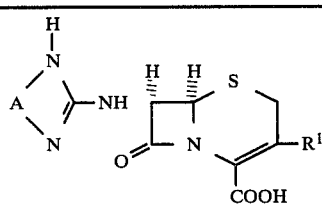

MIC µg/ml.

| Organism | Code No. | A⟨ H / H ⟩ R$^1$ = CH$_2$OCOCH$_3$ | A⟨ ⟩ R$^1$ = (phenyl) CH$_2$OCOCH$_3$ | A⟨ ⟩ R$^1$ = CH$_2$—CH$_2$— CH$_3$ |
|---|---|---|---|---|
| *Strep. pyogenes* | A1 | 16 | 2 | 256 |
| *Staph. aureus* | A6 | 32 | 2 | >256 |
| *E. coli* | A8 | 0.12 | 2 | 8 |
| *K. aerogenes* | A10 | 0.5 | 4 | 8 |
| *Ent. cloacae* | A13 | 4 | >64 | 8 |
| *Serratia marescens* | A16 | 1 | 64 | 32 |
| *Proteus mirabilis* | A18 | 32 | 4 | 256 |
| *Ps. aeruginosa* | A21 | >256 | >64 | >256 | or more known drugs selected from other clinically useful antibacterial agents (for example other β-lactams or aminoglycosides), inhibitors of β-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in δ relative to tetramethylsilane (δ=0) as internal standard, (s=singlet, d=doublet, t=triplet, m=multiplet, br=broad). The temperatures are in degrees Centigrade and the boiling point of the petroleum ether unless otherwise stated is 47°–61° C. The following contractions are used:

| | |
|---|---|
| TFA | = trifluoroacetic acid |
| THF | = tetrahydrofuran |
| HOAC | = acetic acid |
| EtOAc | = ethyl acetate |
| MeOH | = methanol |
| DMF | = dimethylformamide |
| DMSO | = dimethylsulphoxide |
| ether | = diethyl ether |
| HPLC | = high pressure liquid chromatography |

In the examples the cephalosporin derivative of the invention is isolated in the form of a salt, either an internal salt (a zwitterion) or a salt with an acid such as HBr or CF$_3$COOH. The actual salt which is isolated is dependent on a number of factors including the basicity of the product, the reaction, work-up and purification conditions used and the nature of the starting material (salt or free base). Thus, for example, in Examples 1 to 5, because of the pK of the benzimidazole ring, the acid salt isolated is usually the trifluoroacetate but may be a mixture of zwitterion and trifluoroacetate. In Example 6 because of the pK of the imidazoline ring the product may be isolated in the form of zwitterion, the trifluoroacetate, the same salt as that of the starting material (the hydrobromide) or a mixture of any two or three of these.

EXAMPLE 1

A solution of diphenylmethyl 3-acetoxymethyl-7-(benzimidazol-2-yl)aminoceph-3-em-4-carboxylate (0.28 g., 0.5 mmole) in TFA (0.8 ml.) was stirred for 20 minutes at ambient temperature. The TFA was evaporated on an oil pump and the residue was dissolved in CH$_2$Cl$_2$ and the solution washed with water. The organic phase was dried (MgSO$_4$) and concentrated, and to it was then added a mixture of equal parts of toluene and ether. The resulting precipitate was collected and dried to give 0.05 g. of 3-acetoxymethyl-7-(benzimidazol-2-yl) aminoceph-3-em-4-carboxylic acid trifluroacetate, m.p. 210°–230° (decomp.) having the following n.m.r. spectrum in d$_6$DMSO: 2.04(s,3H); 3.82(m,H$_2$O); 4.76(d,1H); 5.07(d,1H); 5.28(d,1H); 5.84(d,1H); 6.8–7.7(m,4H).

The diphenylmethyl 3-acetoxymethyl-7-(benzimidazol-2-yl)aminoceph-3-em-4-carboxylate used as starting material may be obtained as follows:

To a stirred suspension of 7-amino-3-acetoxymethyl-ceph-3-em-4-carboxylic acid toluene-p-sulphonate dihydrate (19.2 g., 40 mmole) in anhydrous THF (500 ml.) under nitrogen in a 1 liter flask was added triethylamine (dried over potassium, 27.76 ml., 200 mmole) then trimethylchlorosilane (20.18 ml., 17.36 g., 160 mmole) while maintaining the temperature at 20° with a cooling bath. After 30 minutes a further 10% of triethylamine and 10% of trimethylchlorosilane were added and the reaction mixture was allowed to stir for a further 2.5 hours. To the mixture was then added acetic formic mixed anhydride (7.04 g., 80 mmole) with cooling in an ice bath. A further 10% trimethylamine, 10% trimethylchlorosilane and 20% acetic formic mixed anhydride, and then yet a further 10% of all three reagents were added to achieve complete disappearance of starting material on t.l.c. Water was then added, the suspension was filtered on a sintered glass disc and the solid dried to give 3-acetoxymethyl-7-formylaminoceph-3-em-4-carboxylic acid.

The above compound was treated with a solution of diphenyldiazomethane in petroleum ether. The product was recrystallized from methanol/ether (3:7 v/v) to give diphenylmethyl 3-acetoxymethyl-7-formylaminoceph-3-em-4-carboxylate, m.p. 157°–158°.

To a 250 ml. 2-necked flask provided with a magnetic stirring bar and dropping funnel dried in the oven was added diphenylmethyl 3-acetoxymethyl-7-formylaminoceph-3-em-4-carboxylate (9.22 g., 20 mmole) followed by methylene chloride (120 ml.) dried over phosphorus pentoxide. The mixture was placed under nitrogen and cooled to −78° in a CO$_2$/acetone bath. Anhydrous pyridine (3.2 ml., 3.12 g., 40 mmole) and then a 20% w/v solution of phosgene in toluene (10.32 ml., 20 mmole) were then added. After the reaction, water (100 ml.) was added and the organic phase was separated, dried over magnesium sulphate and evaporated to dryness. The crude product was chromatographed on silica gel (100 g.) using ether/CH$_2$Cl$_2$ 7:3 v/v as eluant to give 6.0 g. of diphenylmethyl-3-acetoxymethyl-7-isocyanoceph-3-em-4-carboxylate which had the following n.m.r. spectrum in CDCl$_3$: 1.97(s,3H); 3.45(m,2H); 4.75(d,1H); 5.07(d,1H); 4.72(d,1H); 5.05(d,1H); 6.88(s,1H); 7.28(m,10H).

To a solution of diphenylmethyl 3-acetoxymethyl-7-isocyanoceph-3-em-4-carboxylate (0.080 g., 0.178 mmole) in methylene chloride cooled to −78° in a CO$_2$/acetone bath was added a solution of bromine (0.0285 g., 0.178 mmole) in CDCl$_3$. There was thus obtained a solution of diphenylmethyl 3-acetoxymethyl-7-dibromomethyleneaminoceph-3-em-4-carboxylate which was used without further purification. The product had the following n.m.r spectrum in CDCl$_3$: 2.02(s,3H); 3.45(m,2H); 4.73(d,1H); 4.97(d,1H); 5.07(d,1H); 5.25(d,1H); 6.94(s,1H); 7.32(m,10H). This product could, if necessary, be purified by chromatography on silica using CH$_2$Cl$_2$ as eluant.

Alternatively the bromination may be carried out in toluene at −78°, fewer side products thus being produced.

The corresponding dichloro compound was prepared by chlorinating a solution of the isocyanide with a solution of chlorine in carbon tetrachloride at −78°. The product was purified by chromatography on silica gel using CH$_2$Cl$_2$ at −20° as eluant. The product had the following n.m.r. spectrum in CDCl$_3$: 1.98(s,3H); 3.45(m,2H); 4.70(d,1H); 4.92(d,1H); 5.02(d,1H); 5.37(d,1H); 6.92(s,1H); 7.3(m,10H).

To a solution of diphenylmethyl 3-acetoxymethyl-7-dibromomethyleneaminoceph-3-em-4-carboxylate (0.608 g., 1 mmole) in THF stirred under nitrogen at ambient temperature was added orthophenylenediamine (0.216 g., 2 mmole) in THF and the reaction was allowed to continue stirring for 4 hours. The solution was then evaporated to dryness and the residue was dissolved in CH$_2$Cl$_2$ containing a little methanol. This solution was chromatographed on silica gel (50 g.) at −40° using CH$_2$Cl$_2$/MeOH 85:15 v/v as eluant to give diphenylmethyl 3-acetoxymethyl-7-(benzimidazol-2-yl)aminoceph-3-em-4-carboxylate (0.39 g.). The product had the following n.m.r. spectrum in CDCl$_3$: 1.92(s,3H); 3.25(m,2H); 4.57(d,1H); 4.97(d,1H); 5.15(d,1H); 5.90(d,1H); 6.85(s,1H); 3.25(m,10H).

EXAMPLE 2

The process described in Example 1 was repeated using the appropriate starting material and the following compounds were thus prepared:

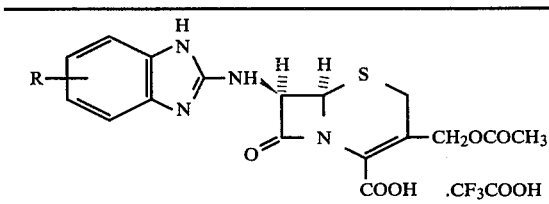

| R (Benzimidazole numbering) | Footnotes |
|---|---|
| 5-methyl | 1,2,3,4 |
| 4-methyl | 5,3,6,7 |
| 5,6-dimethyl | 5,8,3,9 |
| 4-amino | 1,3,10 |
| 4-acetylamino | 1,3,11 |
| 5-nitro | 5,12,3,13 |
| 4-carboxy | 5,3,14 |

Footnotes
1. Reaction carried out in TFA/anisole for 30 minutes.
2. Product purified by chromatography on silica using CH$_2$Cl$_2$/MeOH/HOAc 96:2:2 v/v/v as eluant.
3. Product isolated by dissolving in minimum quantity of CH$_2$Cl$_2$/MeOH and

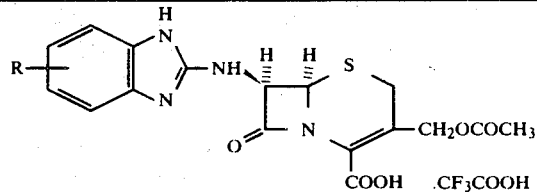

| R (Benzimidazole numbering) | Footnotes |
|---|---| precipitating with ether.
4. The n.m.r. in d$_6$ DMSO/CD$_3$OD:- 2.02(s,3H); 2,43(s,3H); 3.40–4.0(m,2H); 4.0–6.0 (br,4H); 6.70–7.70(m,3H).
5. Reaction carried out in TFA/toluene
6. m.p. 240° (decomp) after recrystallisation from CH$_2$Cl$_2$/MeOH/ether.
7. The n.m.r. in d$_6$ DMSO:- 2.05(s,3H); 2.47(s,3H); 3.48,3.72(2d,2H); 4.75,5.05(2d,2H); 5.32,5.96(2d,2H); 7.05(m,3H).
8. Product purified by chromatography on silica (washed with 2NHCl and reactivated at 120° in vacuo) using CH$_2$Cl$_2$/MeOH/HOAc acid 94:3:3 v/v/v at −25° as eluant. The fractions were acidified with CF$_3$COOH.
9. The n.m.r. in d$_6$ DMSO/CD$_3$OD:- 2.04(s,3H); 2.35(s,6H); 3.43,3.73(2d,2H); 4.85,5.15 (2d,2H); 5.30(d,1H); 5.72(d,1H); 7.23(s,2H).
10. The n.m.r. in d$_6$ DMSO 2.12(s,3H); 3.7(br,2H); 4.77,5.13(2d,2H); 5.37 (d,1H); 5.9(br,1H); 6.60(d,1H); 6.73(d,1H); 7.05(t,1H); 6.90–7.80(br,exchangeable); 10.15 (br,1H, exchangeable).
11. The n.m.r. in d$_6$ DMSO:- 2.02(s,3H); 2.10(s,3H); 3.7(br,2H); 4.7,5.05 (2d,2H); 5.25(d,1H); 5.90(br,1H); 6.90–7.35 (m,3H); 8.35–8.80(m,1H); 9.97(br,1H).
12. Product purified by chromatography on silica using CH$_2$Cl$_2$/MeOH/HOAc acid 97:1.5: 1.5 v/v/v at low temperature.
13. The n.m.r. in d$_6$ DMSO:-2.05(s,3H); 3.57(d,2H); 4.73,5.05(2d,2H); 5.27(d,1H); 5.9(m,1H); 7.6(m,3H).
14. The n.m.r. in d$_6$ DMSO:- 2.05(s,3H); 3.39,3.74(2d,2H); 4.72,5.07(2d,2H); 5.29(d,1H); 5.95(m,1H) 7.36(m,3H).

The starting materials for use in the above process may be prepared by repeating the last part of Example 1 using the appropriate diamine in place of orthophenylene diamine, heating where necessary to complete the reaction. The following compounds were thus obtained:

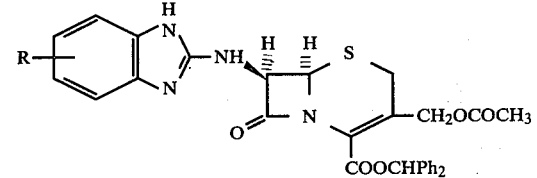

| R (benzimidazole numbering) | Footnotes |
|---|---|
| 5-methyl | 1 |
| 4-methyl | 2,3 |
| 5,6-dimethyl | 4 |
| 4-amino | 5,6,4,3 |
| 5-nitro | 7 |
| 4-carboxy | 8,9 |

Footnotes
1. Product purified by chromatography on silica using CH$_2$Cl$_2$/MeOH/HOAc 98:1:1 v/v/v as eluant.
2. Product purified by chromatography on silica using CH$_2$Cl$_2$/MeOH 99:1 v/v at low -continued

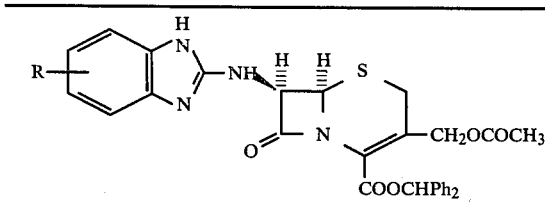

| R (benzimidazole numbering) | Footnotes | temperature as eluant.
3. Product isolated by dissolving in the minimum quantity of CH₂Cl₂/MeOH 8:2 v/v and precipitating with excess ether.
4. Product purified by chromatography on silica using CH₂Cl₂/MeOH/HOAc 94:3:3 v/v/v as eluant.
5. Reaction carried out in toluene at 50°.
6. 40% w/w Excess triamine added to complete the reaction.
7. Product purified by chromatography on silica three times using the following eluants-
(1) CH₂Cl₂/MeOH/HOAc 94:3:3 v/v/v.
(2) CH₂Cl₂/ETOAc/MeOH 76:20:4 v/v/v.
(3) CH₂Cl₂/ETOAc/MeOH 88:10:2 v/v/v.
8. 10% w/w Excess of diamine added three times to complete the reaction.
9. Product purified by chromatography on silica using CH₂Cl₂/MeOH/HOAc 90:5:5 v/v/v at −40°.

The diphenylmethyl 3-acetoxymethyl-7-(4-acetylaminobenzimidazol-2-yl)aminoceph-3-em-4-carboxylate used as starting material may be obtained by reaction of the corresponding 4-aminobenzimidazole derivative in dry methylene chloride with excess acetyl chloride and purifying the product by chromatography on silica using CH₂Cl₂/MeOH/HOAc 97:1:2 v/v/v as eluant.

EXAMPLE 3

The process described in Example 1 was repeated using the appropriate starting materials, and the following compounds were thus prepared:

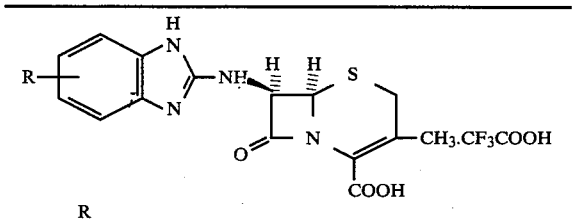

| R (benzimidazole numbering) | Footnotes |
|---|---|
| hydrogen | 1 |
| 5,6-dimethyl | 2,3 |
| 5-methoxy | 4,2,5 |
| 5,6-dichloro | 6,7,8 |
| 4-amino | 4,9,10 |
| 4-acetylamino | 4,9,11 |

Footnotes
1. m.p. 185–187 (decomp.). The n.m.r. spectrum in D₂O/CD₃OD/TFA:- 2.3(s,3H); 3.24,3.60(2d,2H); 7.4(m,4H). The other protons were hidden under solvent resonances. The corresponding sodium salt was obtained by treating a suspension of the trifluoroacetate salt in water with a stoichiometric amount of NaHCO₃. When the reaction mixture was homogeneous, it was extracted twice with CH₂Cl₂ and the aqueous phase was freeze-dried to give the hygroscopic sodium salt. The n.m.r. in D₂O:- 2.10(s,3H); 3.35,3.77(2d,2H) 5.35(d,1H); 5.80(d,1H); 7.20–7.65(m,4H).

-continued

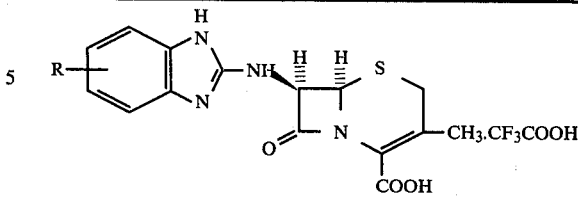

| R (benzimidazole numbering) | Footnotes |

2. Product isolated by dissolving in minimum quantity of CH₂Cl₂ and precipitating with excess ether.
3. The n.m.r. in d₆ DMSO:- 2.04(s,3H); 3.9(m,2H,exchangeable H₂O); 5.75,5.16(2d,2H); 7.03(s,2H). m.p. 198–208°.
4. Reaction carried out in TFA/anisole.
5. m.p. 180–185°. The n.m.r. in CDCl₃/CD₃OD:- 2.04(s,3H); 3.40,3.04(2d,2H); 3.80(s,3H); 3.14(d,1H); 5.44(d,1H); 6.6–7.0(m,2H); 7.27(d,1H).
6. Reaction mixture worked up using ETOAc.
7. Product isolated by dissolving in minimum quantity of CH₂Cl₂/ETOAc and precipitating with excess ether.
8. The n.m.r. in CD₃OD:- 2.18(s,3H); 3.43,3.56(2d,2H); 5.20,5.65(2d,2H); 7.42(s,2H).
9. Product isolated by dissolving in minimum quantity of CH₂Cl₂/MeOH and precipitating with excess ether.
10. The n.m.r. in d₆ DMSO:- 2.08(s,3H); 3.42–3.66(2d,2H); 5.27(d,1H); 5.74(d,1H); 6.52(d,1H); 6.65(d,1H); 6.97(t,1H).
11. m.p. 200° (decomp.). The n.m.r. in d₆ DMSO:- 2.10(s,3H); 2.18(s,3H); 3.38,3.67(2d,2H); 5.23(d,1H); 5.80(d,1H); 7.13(m,3H); 9.15(br,1H, exchangeable); 10.2(s,1H, exchangeable).

The starting materials for use in the above process may be obtained as follows:

To a suspension of 7-amino-3-methylceph-3-em-4-carboxylic acid (7.76 g., 0.036 mole) in anhydrous THF at 0°, cooled in an ice-bath, was added trimethylchlorosilane (7.8 g., 9.07 ml., 2 equivalents) and triethylamine (7.3 g., 10 ml., 2 equivalents). After 10 minutes the ice-bath was removed and the mixture left at ambient temperature for 2 hours. To the mixture was added two equivalents of acetic formic mixed anhydride and the mixture was allowed to stand at ambient temperature for a further 1.5 hours. Water (5 ml.) was added, the precipitated triethylamine hydrochloride was filtered off and the filtrate evaporated on a rotatory evaporator. THF (50 ml.) was added to the residual oil and the solution was esterified with diphenyldiazomethane. The product was purified by chromatography on silica using CH₂Cl₂/ether 1:1 v/v as eluant to give diphenylmethyl 7-formylamino-3-methylceph-3-em-4-carboxylate.

The above formamide (1.02 g.) was dissolved in anhydrous CH₂Cl₂ (10 ml.) and pyridine (0.42 g., 2 equivalents) under nitrogen at −78°. To this solution was added phosgene (0.272 g. as a 20% w/v solution in toluene-1 equivalent) drop by drop. After twenty minutes the reaction mixture was worked up using water and CH₂Cl₂ and the product purified by chromatography on silica using CH₂Cl₂ as eluant. There was thus obtained diphenylmethyl 7-isocyano-3-methylceph-3-em-4-carboxylate.

To a solution of the above isocyanide (0.10 g., 0.256 mmole) in CH₂Cl₂ (10 ml.) under nitrogen at −78° was added dropwise bromine (0.041 g., 13 μl) in CH₂Cl₂ (2 ml.). The end of the reaction was determined by the persistence of the colour of bromine. The solution was evaporated to dryness and the residue purified by chromatography on silica using $CH_2Cl_2$ as eluant. There was thus obtained 0.1 g. of diphenylmethyl 7-dibromomethylene-3-methylceph-3-em-4-carboxylate which was stable at 0°. It had the following n.m.r. spectrum in $CDCl_3$: 2.1(s,3H); 3.07,3.4(2d,2H); 5.14, 4.92(2d,2H); 6.9(s,1H); 7.3(m,10H).

The corresponding dichloroisocyanide was prepared by an identical procedure using a solution of chlorine in $CCl_4$. It had the following n.m.r. spectrum in $CDCl_3$: 2.1(s,3H); 3.1,3.35(2d,2H); 4.92,5.32(2d,2H); 6.9(s,1H); 7.28(m,10H).

The above dibromoisocyanide was prepared from the isocyanide using toluene in place of $CH_2Cl_2$ as solvent. To the reaction mixture was then added the appropriate ortho diamine in $CH_2Cl_2$ at −78°. The reaction mixture was allowed to warm to ambient temperature and stirred from 4 to 24 hours. The product was isolated by washing the organic layer with water and chromatographing the residue obtained by evaporation of the dried organic layer. (Note that if THF was used in place of $CH_2Cl_2$ as the reaction solvent, a purer product containing no $\Delta^2$ isomer was obtained, and the reaction was completed in a shorter time). The following compounds were thus obtained:

[Structure: R-substituted benzimidazole linked via NH to cephem with COOCHPh₂]

| R (benzimidazole numbering) | Footnotes |
|---|---|
| H | 1,2 |
| 5,6-dimethyl | 3,2 |
| 5-methoxy | 1,4 |
| 5,6-dichloro | 1,5,6 |
| 4-amino | 1,7,8 |

Footnotes
1. Two equivalents of orthophenylenediamine used.
2. Product purified by chromatography on silica using $CH_2Cl_2$/MeOH 95:5 v/v as eluant.
3. 1.5 Equivalents of diamine, followed after five hours by a further 0.5 equivalents of diamine used.
4. Product purified by chromatography on silica using $CH_2Cl_2$/ETOAc/MeOH 58:40:2 v/v/v as eluant.
5. Reaction mixture heated at 50° for 18 hours.
6. Product purified by chromatography on silica using the following eluants.
(1) $CH_2Cl_2$ followed by $CH_2Cl_2$/MeOH 95:5 v/v.
(2) $CH_2Cl_2$/HOAc 90-85:10-15 v/v.
7. Reaction mixture heated at 50° for 4 hours.
8. Product purified by chromatography on silica using $CH_2Cl_2$/MeOH/HOAc acid 94:3:3 v/v/v at 0° as eluant.

The product crystallised from toluene containing a little ether and methanol. The diphenylmethyl 7-(4-acetylaminobenzimidazol-2-yl)-3-methylceph-3-em-4-carboxylate used as starting material may be obtained by reaction of the corresponding 4-aminobenzimidazole derivative with one equivalent of acetyl chloride in anhydrous $CH_2Cl_2$ under nitrogen and isolating the product by precipitating it from a solution in a mixture of the minimum quantity of $CH_2Cl_2$ and methanol with excess ether.

EXAMPLE 4

The process described in Example 1 was repeated using the appropriate starting materials and the following compounds were thus prepared. The reaction was conducted in trifluoroacetic acid/anisole and the product isolated by addition of ether to a concentrated methanol solution.

[Structure: RNH-cephem with $CH_3.CF_3COOH$ and COOH]

| R | m.p. °C. | Footnote |
|---|---|---|
| [benzimidazole, H] | 220–225 | 1 |
| [acenaphthylene-fused benzimidazole, H] | 350 (decomp.) | 2 |

Footnotes
1. The n.m.r. in $d_6$ DMSO:- 2.08(s,3H); 3.35(d,1H); 3.68(d,1H); 5.25(d,1H); 5.85(d,1H); 7.20–8.15(m,6H).
2. The n.m.r. in $d_6$ DMSO:- 2.03(s,3H); 3.32(s,4H); 3.30(d,1H); 3.60(d,1H); 5.22(d,1H); 5.80(d,1H); 4.30–6.70(m,exchangeable); 7.15(d,1H); 7.30(s,1H); 7.44(t,1H); 7.87(d,1H); 8.57(br,exchangeable).

The starting materials for use in the above process may be obtained by repeating the processes described in the last two parts of Example 3, carrying out the bromination in methylene chloride and using the appropriate diamine, carrying out the last part in tetrahydrofuran. The mixture was heated at 50° for 2–4 hours. The following compounds were thus obtained.

[Structure: RNH-cephem with COOCHPh₂]

| R | m.p. °C. | Footnotes |
|---|---|---|
| [benzimidazole, H] | 141–143 | 1 |

-continued

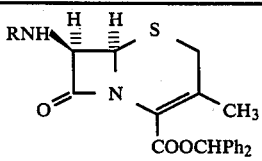

| R | m.p. °C. | Footnotes |
|---|---|---|
| (acenaphtho-imidazole structure) | 150–154 | 2 |

Footnotes
1. The product was purified by chromatography on silica using $CH_2Cl_2$/HOAc/MeOH 97:1.5:1.5 v/v/v as eluant. The product was isolated by addition of petroleum ether to a THF solution.
2. The product was purified by chromatography on silica gel using $CH_2Cl_2$/HOAc/MeOH 94:3:3 v/v/v as eluant. The product was isolated by addition of petroleum ether to a $CH_2Cl_2$/MeOH solution.

EXAMPLE 5

The process described in Example 4 was repeated using the appropriate starting materials and the following compounds were thus obtained:

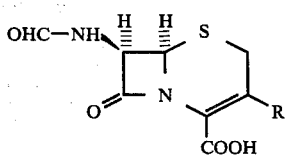

| R | m.p. °C. | Footnote |
|---|---|---|
| CH₃-N=N / CH₂S—triazole—N / N—N | 182–187 (decomp) | 1 |
| CH₂S—S / CH₃ thiadiazole / N—N | 174–176 | 2 |

Footnotes
1. The n.m.r. in $d_6$ DMSO: - 3.6(d,1H); 3.9(d,1H); 3.95(s,3H); 4.34(m,2H); 5.25(d,1H); 5.81(d,1H); 6.90–7.50(m,4H).
2. The n.m.r. in $d_6$ DMSO: - 2.69(s,3H); 3.59(d,1H); 3.84(d,1H); 4.23(d,1H); 4.59(d,1H); 5.25(d,1H); 5.82(d,1H); 7.1–7.5(br,4H).

The starting materials for use in the above process may be obtained as follows:

To a stirred suspension of 7-amino-3-acetoxymethyl-ceph-3-em-4-carboxylic acid (13.5 g., 0.05 mole) in water (100 ml.) and acetone (50 ml.) was added a solution of sodium bicarbonate (9.45 g., 0.113 mole) in water (50 ml.). When a homogeneous solution was obtained, 2-methyl-1,2,4-thiadiazole-5-thiol(10 g., 0.075 mole) was added and the mixture heated at 40°–50° under nitrogen while the pH was adjusted to 7.6 by the addition of a solution of 3N HCl. The pH was maintained at 7.6 and the course of the reaction was followed by removing 0.3 ml. aliquots, adjusting the pH to 3 with 1NHCl, filtering the precipitate, washing it with acetone and then ether and examining it by infra red for the disappearance of the carbonyl absorption. The reaction was complete after 10.5 hours and the whole reaction was worked in the same way as described above for the aliquots. There was thus obtained 7-amino-3-[(2-methyl-1,3,4-thiadiazol-5-yl)thiomethyl]ceph-3-em-4-carboxylic acid. In a similar manner, but using an equivalent amount of 1-methyl-1H-tetrazole-5-thiol in place of 2-methyl-1,2,4-thiadiazole-5-thiol, but making the initial adjustment of pH to 7.6 with sodium bicarbonate, and carrying out the reaction for 5 hours under reflux, there was obtained 7-amino-3-[(1-methyl-1H-tetrazol-5-yl)thiomethyl]ceph-3-em-4-carboxylic acid.

The processes described in the second, third, fourth, fifth and seventh parts of Example 1 were repeated in sequence using the appropriate starting materials, and the following compounds were thus obtained:

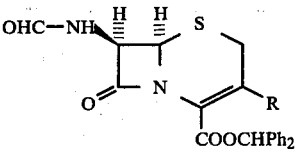

| R | Footnote |
|---|---|
| CH₃-N / CH₂S—tetrazole / N—N | 1 |
| CH₂S—S / CH₃ thiadiazole / N—N | 1 |

Footnote
1. The product was isolated by adding a little water to the reaction mixture, filtering, and evaporating the filtrate.

(OHC—NH-β-lactam-R with COOCHPh₂)

| R | Footnotes |
|---|---|
| CH₃-N / CH₂S—tetrazole / N—N | 1 |
| CH₂S—S / CH₃ thiadiazole / N—N | 2 |

Footnotes
1. The esterification was carried out in pentane. The ester crystallised in the course of the reaction.
2. The esterification was carried out in THF/pentane. The ester was purified by chromatography on silica using $CH_2Cl_2$/ether 90:10 then 70:30 v/v as eluant.

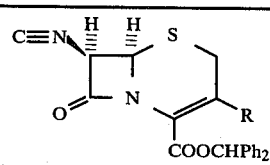

| R | Footnote |
|---|---|
| CH2S-[triazole]-CH3 (1,2,4-triazole with CH3) | 1 |
| CH2S-[thiazole]-CH3 (N—N thiadiazole) | 2 |

Footnotes
1. The reaction was carried out in anhydrous pyridine. The product was purified by chromatography on silica using cyclohexane/ethyl acetate 1:1 v/v as eluant by which means the unwanted $\Delta^2$ isomer was readily separated from the required $\Delta^3$ isomer, m.p. 138°.
2. The starting material, in the form of the dihydrate, was first dried by dissolving in dry dichloroethane and evaporating the solution to dryness. This process was repeated several times and the residue was finally dried in vacuo for 24 hours. The reaction product was purified by chromatography on silica using CH2Cl2/ether 9:1 v/v as eluant. The purified solid was washed with an ETOAc/ether mixture.

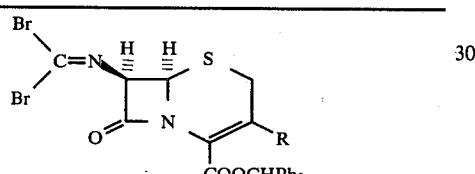

| R | Footnotes |
|---|---|
| CH2S-[triazole]-CH3 | 1,2 |
| CH2S-[thiadiazole]-CH3 | 1,3 |

Footnotes
1. Bromination carried out in toluene.
2. The n.m.r. in d6DMSO: - 3.85(m,2H); 4.35(m,2H); 5.3(d,1H); 5.65(d,1H); 6.95(s,1H); 7.4(m,10H).
3. The product was purified by chromatography at −20° on silica using CH2Cl2/ether 95:5 v/v as eluant. The product had m.p. 125-127° and had the following n.m.r.in d6 DMSO: - 2.65(s,3H); 3.55(br,2H); 4.15(d,1H); 4.65(d,1H); 4.95(d,1H); 5.25(d,1H); 7.95(s,1H); 7.2-7.5(m,10H).

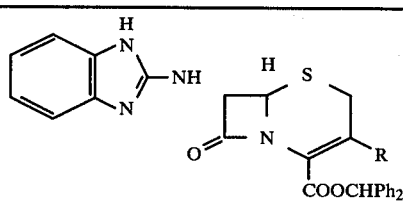

| R | Footnotes |
|---|---|
| CH2S-[triazole]-CH3 | 1,2 |

-continued

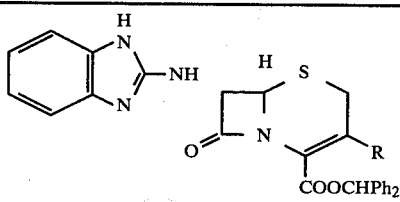

| R | Footnotes |
|---|---|
| CH2S-[thiadiazole]-CH3 | 1,3 |

Footnotes
1. The reaction was carried out at 50–55° C.
2. The product was purified by chromatography in silica at −20° using CH2Cl2/MeOH/HOAc 94:3:3 v/v/v as eluant. After precipitation m.p. = 130–132°.
3. After 2 hours no further reaction occurred. The product was purified by chromatography on silica using CH2Cl2/HOAc/MeOH 92:5:5 v/v/v as eluant. The product was precipitated from THF solution with petroleum ether, m.p. 118–120°.

EXAMPLE 6

The process described in Example 1 was repeated using the appropriate starting materials, and the following compounds were thus prepared:

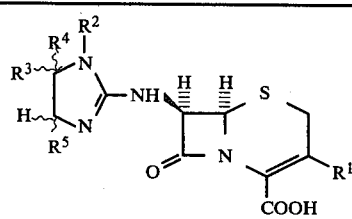

| R¹ | R² | R³ | R⁴ | R⁵ | Footnotes |
|---|---|---|---|---|---|
| CH3 | H | H | H | H | 1,2 |
| CH3 | H | CH3 | H | H | 3,4 |
| CH3 | H | CH3 | CH3 | H | 5 |
| CH3 | H | Ph | H | H | 3,6 |
| CH3 | COCH3 | H | H | H | 3,7 |
| CH3 | CH3 | H | H | H | 3,8 |
| CH2OCOCH3 | H | H | H | H | 3,9 |
| CH3 | H | H | cis-(CH2)4 | | 3,10 |
| CH2OCOCH3 | H | Ph | H | H | 3,11 |

Footnotes
1. The residue obtained from the reaction mixture was dissolved in CH2Cl2/MeOH 90:10 v/v. The precipitated solid was removed and the filtrate evaporated to dryness and dissolved in methanol. The zwitterion of the product crystallised out. It had the following n.m.r. in D2O:-
2.38(s,3H); 3.70(d,1H); 4.11(d,1H); 4.22(s,4H); 5.60(d,1H); 5.80(d,1H).
2. By carrying out the deprotection with TFA in toluene and recrystallising the residue from isopropanol, the hydrobromide, m.p. 200–202° (decomp.) was obtained. n.m.r. in d6 DMSO:- 2.08(s,3H); 3.38(d,1H); 3.65(d,1H); 3.65(s,1H); 5.12(d,1H); 5.52(m,1H); 8.35(m,1H); 9.35(m,1H).
3. Reaction carried out in TFA toluene.
4. Product isolated by addition of ether to solution in CH2Cl2/MeOH to give HBr, m.p. 160–164°. n.m.r. in CD3OD:-
1.35(d,3H); 2.13(s,3H); 3.28(d,1H); 3.59(d,1H); 4.2(br,3H); 5.12(d,1H); 5.3(d,1H).
5. Product chromatographed on silica at −25° using CH2Cl2/HOAc/MeOH 70:15:15 v/v/v as eluant. Product, mainly TFA salt, containing 1 mole of H2O, isolated by adding -continued

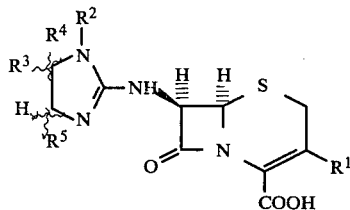

| $R^1$ | $R^2$ | $R^3$ | $R^4$ | $R^5$ | Footnotes |
|---|---|---|---|---|---| ether to MeOH solution. n.m.r. in $d_6$ DMSO:-
1.35(s,6H); 2.02(s,3H); 3.35(s,2H); 3.7(br,2H);
5.05(d,1H); 5.38(d,1H); 8.50-9.40(m,2H).
6. The starting material was not isolated.
The THF reaction medium for the starting material was replaced by toluene. The product was purified by rapid chromatography on silica at $-20°$ using $CH_2Cl_2$ HOAc/MeOH 75:15:15 v/v/v as eluant. Product isolated as the TFA salt containing 2 moles of $H_2O$ by adding ether to MeOH/THF solution. m.p. 175-177° (decomp).
n.m.r. in $d_6$ DMSO:- 2.07(s,3H); 3.30(m,2H);
3.50(m,1H); 4.15(m,1H); 5.15(d,1H); 5.21(t,1H);
5.51(d,1H); 7.40(s,5H); 9.0(br,1H exchangeable).
7. Product isolated by addition of ether to THF solution as mainly the TFA salt, m.p. 110-115°, n.m.r. in $d_6$ DMSO:- 2.03(s,3H); 2.26(s,3H); 3.30(d,1H); 3.62(d,1H); 3.73(m,2H); 4.13(m,2H);
5.16(d,1H); 5.51(d,1H); 7.22(m,1H).
8. Product isolated by addition of ether to $CH_2Cl_2$/MeOH solution as mainly the HBr salt. m.p. 153-156°, n.m.r. in $d_6$ DMSO:-
2.06(s,3H); 2.97(s,3H); 3.49(s,2H); 3.64(s,4H);
5.1(d,1H); 5.44(d,1H).
9. Product, the TFA salt, isolated by addition of ether to $CH_2Cl_2$/MeOH solution.
n.m.r in $CD_3OD/CF_3COOD$:- 2.10(s,3H); 3.44(d,1H);
3.81(d,1H); 3.81(s,4H); 4.86(d,1H); 5.19(d,1H);
5.20(d,1H); 5.51(d,1H).
10. Product isolated by dropwise addition of ether to a $CH_2Cl_2$/MeOH solution, mainly the HBr salt, m.p. 167-170°, n.m.r $d_6$ DMSO:- 1.52(br,8H);
2.08(s,3H); 3.38(d,1H); 3.65(d,1H); 3.92(s,2H);
5.12(d,1H); 5.45(d,1H).
11. The residue from the reaction was partitioned between $CH_2Cl_2$ and water and the aqueous layer evaporated to give the product as the TFA salt, n.m.r. in $d_6$ DMSO:- 2.0(s,3H);
4.75(d,1H); 5.0(d,1H); 5.1(d,1H); 5.55(m,1H);
5.2(m,1H). A number of resonances were obscured by a broad exchangeable resonance.

The starting materials for use in the above process may be prepared by repeating the process described in the last part of Example 1 using the appropriate starting materials. The reaction mixture was initially worked up by adding a slight excess of HBr, or preferably TFA in order completely to neutralise the excess diamine. The following compounds were thus prepared:

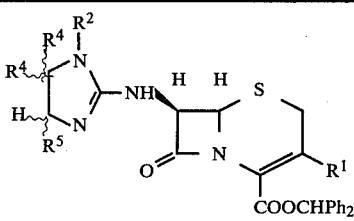

| $R^1$ | $R^2$ | $R^3$ | $R^4$ | $R^5$ | Footnotes |
|---|---|---|---|---|---|
| $CH_3$ | H | H | H | H | 1,2 |
| $CH_3$ | H | $CH_3$ | H | H | 3,4 |
| $CH_3$ | H | $CH_3$ | $CH_3$ | H | 3 |
| $CH_3$ | H | Ph | $CH_3$ | H | 5 |

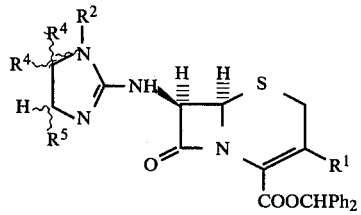

| $R^1$ | $R^2$ | $R^3$ | $R^4$ | $R^5$ | Footnotes |
|---|---|---|---|---|---|
| $CH_3$ | $COCH_3$ | H | H | H | 6 |
| $CH_3$ | $CH_3$ | H | H | H | 1,7 |
| $CH_2OCOCH_3$ | H | H | H | H | 3 |
| $CH_3$ | H | H | cis $(CH_2)_4$ | 1,8 |
| $CH_2OCOCH_3$ | H | Ph | H | H | 9 |

Footnotes
1. Product purified by chromatography on silica at $-20°$ using $CH_2Cl_2$/MeOH 95:5 v/v as eluant.
2. m.p. 156-158°.
3. Product purified by chromatography on silica at $-30°$ using $CH_2Cl_2$/MeOH 92:8 v/v as eluant.
4. Product isolated by adding ether to $CH_2Cl_2$ solution, m.p. 138-140°.
5. The starting material, obtained by bromination of the isocyanide, was not isolated. The $CH_2Cl_2$ solvent used for the bromination was replaced by THF.
6. The starting material in the form of the free base was obtained by acylation of the corresponding NH compound with acetic anhydride/triethylamine in THF.
7. m.p. 143-145° on recrystallisation from $CH_2Cl_2$.
8. m.p. 142-145° on recrystallisation from $CH_2Cl_2$.
9. 4 moles of TFA rather than HBr added to reaction mixture before work-up. Product purified by chromatography on silica at $-45°$ using $CH_2Cl_2$/MeOH 97:3 v/v as eluant. Product, m.p. 107-112°, isolated by precipitation with ether.

EXAMPLE 7

A solution of t-butyl 3-methyl-7-(1-methylbenzimidazol-2-yl)aminoceph-3-em-4-carboxylate in two volumes of TFA and one volume of anisole was allowed to stand at ambient temperature for 1.5 hours. The solvent was removed by evaporation and the product, 3-methyl-7-(1-methylbenzimidazol-2-yl)aminoceph-3-em-4-carboxylic acid, was purified by recrystallisation from isopropanol, m.p. 181°-182° (decomp.), having the following n.m.r. spectrum in $d_6$DMSO: 2.05(s,3H); 3.5(m,2H); 3.7(s,3H); 5.2(d,1H); 5.7(d,1H); 7.2-7.7(m,4H).

The t-butyl 3-methyl-7-(1-methylbenzimidazol-2-yl)aminoceph-3-em-4-carboxylate used as starting material may be obtained as follows:

A solution of t-butyl 7-amino-3-methylceph-3-em-4-carboxylate (0.5 mmole) in methanol (0.5 ml.) was treated with 1-methyl-3-methoxybenzimidazolium iodide (0.5 mmole) and the reaction mixture was stirred for 48 hours at room temperature. The product was purified by chromatography on silica gel using $CH_2Cl_2$/MeOH 97:3 v/v as eluant followed by recrystallisation from isopropanol to give 3-methyl-7-(1-methylbenzimidazol-2-yl)aminoceph-3-em-4-carboxylate, m.p. 113°-116° and having the following n.m.r. spectrum in $CDCl_3$: 1.5(s,9H); 2.1(s,3H); 3.17(d,1H); 3.5(d,1H); 3.55(s,3H); 5.1(d,1H); 6.05(d,1H); 6.9-7.6(m,4H).

The 3-methyl-7-(1-methylbenzimidazol-2-yl)aminoceph-3-em-4-carboxylic acid may also be prepared by direct reaction at ambient temperature between 7-amino-3-methylceph-3-em-4-carboxylic acid and 1-methyl-3-methoxybenzimidazolium iodide in aqueous buffer or in water containing 1 equivalent of $NaHCO_3$.

EXAMPLE 8

The process described in Example 7 was repeated using the corresponding 3-acetoxymethyl derivative and there was thus obtained 3-acetoxymethyl-7-(1-methylbenzimidazol-2-yl)aminoceph-3-em-4-carboxylic acid, m.p. 190° (decomp.) after precipitation from a $CH_2Cl_2$/MeOH solution with ether. The product had the following n.m.r. spectrum in $d_6$DMSO: 2.0(s,3H); 3.58(s,+m, 3H+2H); 4.67(d,1H); 4.95(d,1H); 5.2(d,1H); 5.76(d,1H); 6.95–7.42(m,4H).

The starting material may be prepared by repeating the second part of Example 7, but using t-butyl 3-acetoxymethyl-7-(1-methylbenzimidazol-2-yl)aminoceph-3-em-4-carboxylate in place of the corresponding 3-methyl derivative, 1-methyl-3-methoxybenzimidazolium methanesulphonate in place of the corresponding iodide and carrying out the reaction over 3 days. The product was purified by chromatography on silica gel using $CH_2Cl_2$/MeOH/HOAc 98:1:1 v/v/v as eluant to give t-butyl 3-acetoxymethyl-7-(1-methylbenzimidazol-2-yl)aminoceph-3-em-4-carboxylate, m.p. 98°–103° and having the following n.m.r. spectrum in $d_6$DMSO: 1.5(s, 9H); 2.0(s,3H); 3.38(d,1H); 3.6(d,1H); 3.53(s,3H); 4.56(d,1H); 4.8(d, 1H); 5.17(d, 1H); 5.8(m,1H); 6.75–7.26(m,4H).

EXAMPLE 9

The process described in Example 1 was repeated using the appropriate starting materials, and the following compounds were thus prepared:

TABLE I

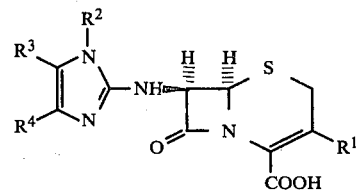

| R¹ | R² | R³ | R⁴ | Footnotes |
|---|---|---|---|---|
| CH₃ | H | OH | H | 1, 2, 3, 4 |
| CH₃ | H | CN | CN | 1, 5, 6, 7 |
| CH₃ | OH | CH₃ | H | 1, 8, 9, 10 |
| CH₂OCOCH₃ | H | OH | H | 11, 12, 13 |
| CH₃ | H | H | H | 14, 15, 16 |
| CH₃ | H | CH₃ | H | 17, 18, 19 |

Footnotes
1. Reaction carried out in TFA/anisole 50:50 v/v.
2. Reaction conducted at ambient temperature for 1.5 hours.
3. Product isolated by evaporation of reaction mixture and recrystallisation of residue from MeOH
4. Product had m.p. 217–218° and the following n.m.r. in $d_6$ DMSO:- 2.00 (s, 3H); 3.30 (d, 1H); 3.60 (d, 1H); 3.60 (d, 2H); 4.95 (d, 1H); 5.55 (d-d, 1H); 6.40 (t, 1H); 6.95–7.30 (m, 2H).
5. Reaction conducted at 0° for 15 minutes.
6. Product isolated by evaporation of reaction mixture and recrystallisation of residue from ether.
7. Product had following n.m.r. in $CD_3OD$:- 2.15 (s, 3H); 3.25–3.55 (m, 2H); 5.10 (d, 1H); 5.55 (d, 1H).
8. Reaction conducted at −25° for 15 minutes.
9. Product isolated by evaporation of reaction mixture chromatography of the residue on silica gel below −20° using $CH_2Cl_2$/MeOH/HOAc 88:8:4 v/v/v as eluant and precipitation of the product from $CH_2Cl_2$ solution with di-isopropyl ether.
10. Product had m.p. >220° (decomp.) and the following n.m.r. in $d_6$ DMSO:- 2.04 (s, 6H); 3.44 (s, 2H); 5.04 (d, 1H); 5.48 (d, 1H); 6.42 (s, 1H).
11. Reaction carried out in TFA/toluene at ambient temperature for 20 minutes.

TABLE I-continued

12. Product isolated by evaporation of the reaction mixture and recrystallisation of the residue from isopropanol.
13. Product had m.p. >220° (decomp.) and the following n.m.r. in $d_6$DMSO:-2.0 (s,3H); 4.65 (d, 1H); 5.0 (d, 1H); 5.05 (d, 1H); 5.65 (d-d, 1H); 6.35 (t, 1H); 7.05 (d, 1H); 6.95 (br s, 1H).
14. Reaction carried out in TFA only at 0° for 2 hours.
15. Product, as the TFA salt isolated by trituration of residue from reaction with ether.
16. Product had the following n.m.r. in $d_6$DMSO:- 2.075 (s, 3H); 3,48 (q, 2H); 5.13 (d,1H); 5.5 (q, 1H); 7.07 (s, 2H); 9.45 (d, 1H).
17. Reaction conducted in TFA/anisole 0.85:2.8 v/v first at 0° then for 0.5 hours at ambient temperature.
18. Product isolated by evaporation of the reaction mixture at 25° and precipitation from $CH_2Cl_2$/MeOH solution with ether/hexane 50:50 v/v.
19. The product had the following n.m.r. spectrum in $d_6$DMSO:- 2.08 (s, 3H); 2.10 (s, 3H); 3.44 (d-d, 2H); 6.10 (d, 1H); 6.48 (d, 1H); 6.55 (br s, 1H).

The starting materials and intermediates for use in the above process may be prepared by repeating the last part of Example 1 or the last part of Example 3, using the appropriate starting material in place of the ortho diamine. The following compounds were thus obtained:

TABLE II

| R¹ | R² | R³ | R⁴ | Footnotes |
|---|---|---|---|---|
| CH₃ | H | OH | H | 1 |
| CH₃ | H | CN | CN | 2 |
| CH₃ | OH | CH₃ | H | 3 |
| CH₂OCOCH₃ | H | OH | H | 4 |

Footnotes
1. The reaction was carried out by addition of a solution of 1 equivalent of the 7-dibromomethyleneamino derivative in THF to a solution of 2 equivalents of glycine amide in THF containing the minimum amount of MeOH to achieve solution, at −78°. The temperature was allowed to rise to ambient temperature and the product purified by chromatography on silica gel using EtOAc/ $CH_2Cl_2$ 20:80 v/v as eluant. The product was recrystallised from isopropanol/$CH_2Cl_2$ and had m.p. 192–194°.
2. The reaction was carried out as in footnote 1, using 2 equivalents of 1,2-diamino-1,2-dicyanoethylene. The product was recrystallised from anhydrous $CH_2Cl_2$ and had m.p. 180–185°.
3. The reaction was carried out by adding a solution of 1-amino-2-oximinopropane (528 mg.) in THF containing the minimum amount of MeOH to a solution of the 7-dibromomethyleneamino derivative (1.1 g.) in anhydrous THF (30 ml.) at −50°. The reaction temperature was allowed to rise to −25° over 2 hours, TFA (500 μl.) was then added, and the solvent removed by evaporation. The residue was purified by chromatography on silica gel at −20° using $CH_2Cl_2$/ MeOH 96:4 v/v as eluant and the product finally precipitated from $CH_2Cl_2$ solution by addition of di-isopropyl ether, TABLE II-continued R³—[imidazole ring with R²,R⁴]—NH—CH—CH—S—CH₂—C(=R¹)—...
structure with COOCHPh₂

| R¹ | R² | R³ | R⁴ | Footnotes | m.p. 140–145° (decomp.).
4. The product was purified by chromatography on silica gel below −20° using EtOAc/CH₂Cl₂ 20:80 v/v as eluant. The product was recrystallised from isopropanol, m.p. 176–179°.

The starting material of the formula given in Table II above in which $R^1$ is $CH_3$, $R^2$ is H, $R^3$ is $CH_3$ and $R^4$ is H may be prepared from the corresponding compound in which $R^2$ is OH by reaction in methanol with 1.7 equivalents of titanium trichloride at 40°–45° for 30 minutes followed by addition of diphenyldiazomethane to re-esterify any free acid.

The starting material of the formula given in Table II above in which $R^1$ is $CH_3$ and $R^2$, $R^3$ and $R^4$ are H may be prepared by reaction of 2-fluoroimidazole with t-butyl 7-amino-3-methylceph-3-em-4-carboxylate toluene-p-sulphonate in acetonitrile at 70° for 4 hours. The product was purified by preparative t.l.c. using CH₂Cl₂/MeOH 9:1 v/v as developing solvent.

EXAMPLE 10

The process described in Example 1 or Example 7 was repeated using the appropriate diphenylmethyl or t-butyl ester as starting material, and the following compounds were thus obtained:

TABLE I

[benzimidazole]—NH—CH—CH—S—CH₂—C(=CH₂OCOCH₃)—N—C(=O)—COOH structure

| R¹ | R² (benzimidazole numbering) | Footnotes |
|---|---|---|
| H | 5-OH | 1, 2, 3 |
| CH₂—C₆H₄—OCH₃ | H | 4, 2, 5 |
| H | 4-OH | 6, 7, 8 |
| H | 5-CH₂NH₂ | 9, 10, 11 |

Footnotes
1. The reaction was carried out in TFA/anisole 1.5:1 v/v at ambient temperature for 3.5 hours.
2. Product isolated by evaporation of reaction mixture to dryness followed by precipitation from CH₂Cl₂ solution with ether.
3. Product had m.p. 180° (decomp.) and the following n.m.r. spectrum in d₆ DMSO:- 2.05 (s, 3H); 3.42 (d, 1H); 3.68 (d, 1H); 4.70 (d, 1H); 5.05 (d, 1H); 5.18 (d, 1H); 5.78 (d, 1H); 6.4–7.1 (m, 4H).
4. Reaction carried out in TFA/anisole 1:1 v/v at ambient temperature for 30 minutes.
5. Product had m.p. 160° and the following n.m.r. in TABLE I-continued

[benzimidazole]—NH—CH—CH—S—CH₂—C(=CH₂OCOCH₃)—N—C(=O)—COOH structure

| R¹ | R² (benzimidazole numbering) | Footnotes |

CD₃OD containing 2 drops of d₆DMSO:-2.00 (s, 3H); 3.70 (s, 3H); 3.5 (d, 1H); 3.75 (d, 1H); 4.8 (m, 2H); 5.15 (d, 1H); 5.67 (d, 1H); 5.31 (s, 2H); 6.66–7.66 (m, 8H).
6. Reaction carried out in TFA/anisole 1:2 v/v at ambient temperature for 35 minutes.
7. Product isolated by evaporation of reaction mixture to dryness and adding to the residue CH₂Cl₂ containing a little MeOH whereupon the product crystallised.
8. Product had m.p. 190° (decomp.) and the following n.m.r. in CD₃OD/d₆ DMSO:- 2.05 (s, 3H); 3.52 (d, 1H); 3.80 (d, 1H); 4.87 (d, 1H); 5.16 (d, 1H); 5.28 (d, 1H); 5.74 (d, 1H); 6.6–7.3 (m, 3H).
9. Reaction carried out in TFA/anisole 5:1.6 v/v at ambient temperature for 20 minutes under nitrogen.
10. Product isolated by evaporation of reaction mixture to dryness followed by precipitation from MeOH solution with ether.
11. Product had the following n.m.r. in d₆DMSO:- 2.01 (s, 3H); 3.55 (m, 3H); 4.04 (m, 2H); 4.68 (s, 1H); 5.01 (s, 1H); 5.22 (s, 1H); 5.85 (s, 1H); 7–7.4 (m, 3H).

The starting materials for use in the above process may be prepared by repeating the last part of Example 1 using the appropriate diamine in place of orthophenylene diamine. The following compounds were thus obtained:

TABLE II

[benzimidazole]—NH—CH—CH—S—CH₂—C(=CH₂OCOCH₃)—N—C(=O)—COOR³ structure

| R¹ | R² | R³ | Footnotes |
|---|---|---|---|
| H | 5-OH | t-C₄H₉ | 1 |
| H | 4-OH | CHPh₂ | 2, 3 |
| H | 5-CH₂NHCOO-C₄H₉ᵗ | CHPh₂ | 4, 5 |

Footnotes
1. The product was purified by chromatography on silica using CH₂Cl₂/MeOH/HOAc 96:2:2 v/v/v as eluant. The product was recrystallised from CH₂Cl₂, m.p. 160° (decomp.).
2. Reaction carried out under argon at 45°.
3. Product purified by chromatography on silica gel at −40° using CH₂Cl₂/ether/MeOH 65:35:2 v/v/v as eluant, followed by chromatography on silica at −40° using EtOAc/CH₂Cl₂/MeOH 25:70:5 v/v/v as eluant. This product was used without further purification.
4. Reaction period 18 hours.
5. Product purified by chromatography on silica at −40 ° under 0.3 Bar pressure using CH₂Cl₂/MeOH/HOAc 98:1.3:0.67 v/v/v as eluant.

Referring to the formula at the head of Table II above, the starting material in which $R^2$ is hydrogen, $R^1$ is 4-methoxybenzyl and $R^3$ is t-butyl may be obtained by reaction of equimolar amounts of t-butyl 7-amino-3-acetoxymethylceph-3-em-4-carboxylate and 1-methoxy-3-(4-methoxybenzyl)imidazolium iodide in anhydrous methanol at ambient temperature for 36 hours. The reaction mixture was evaporated to dryness and the product purified by chromatography on silica using CH$_2$Cl$_2$/ether/MeOH 49.5:49.5:1 v/v/v as eluant.

The t-butyl 3-acetoxymethyl-7-dibromomethyleneaminoceph-3-em-4-carboxylate used as an intermediate may be prepared as follows:

To a solution of t-butyl 7-amino-3-acetoxymethyl-ceph-3-em-4-carboxylate (3.26 g.) in CH$_2$Cl$_2$ (50 ml.) at 0° was added acetic formic mixed anhydride (0.88 g.). The reaction mixture was stirred at 0° for 10 minutes then evaporated to dryness. The residue was dissolved in ether/CH$_2$Cl$_2$ 2:1 v/v, and the volume reduced without heating. On cooling the solution, the 7-formylamino compound, m.p. 110°–115°, crystallised. To a solution of this product (365 mg.) in CH$_2$Cl$_2$ (10 ml.) was added pyridine (790 mg.) then after cooling to −78° under nitrogen a 20% w/v solution of phosgene in toluene (555 μl). Ice (5 g.) was then added and the organic phase washed 4 times with water, dried and evaporated to dryness. The product, the 7-isocyanide, was purified by chromatography on silica gel using CH$_2$Cl$_2$/ether as eluant. To a solution of this isocyanide (169 mg.) in toluene at −78° was dropwise added bromine (26 μl.) in CH$_2$Cl$_2$. When the starting material had disappeared (t.l.c.) the reaction mixture was evaporated to dryness without heating to give t-butyl 3-acetoxymethyl-7-dibromomethyleneaminoceph-3-em-4-carboxylate which was used without further purification.

The 1,2-diamino-4-(t-butoxycarbonylaminomethyl)-benzene used as an intermediate may be prepared as follows:

One equivalent of diborane in THF was added to a solution of 1-amino-2-nitro-4-cyanobenzene (500 mg.) in anhydrous THF (20 ml.) under nitrogen at 10°. After 2 hours excess diborane was destroyed by addition of MeOH and the reaction mixture was evaporated to dryness. The residue was dissolved in methanol and methanolic HCl added. The solvent was evaporated, the residue was basified and the product extracted with ether (×3). The combined extracts were dried and evaporated to give impure 1-amino-2-nitro-4-aminomethyl-benzene. To a solution of this diamine (350 mg.) in dry dioxan (10 ml.) was added "Boc-On" (Aldrich Chemical Co.) (258 mg.). The reaction mixture was stirred at ambient temperature for 18 hours, concentrated, and the residue purified by chromatography on silica using CH$_2$Cl$_2$/ether as eluant. There was thus obtained 1-amino-2-nitro-4-(t-butoxycarbonylaminomethyl)benzene. This product was hydrogenated at ambient pressure in THF/ethanol solution using 10% w/w palladium-on-carbon catalyst to give 1,2-diamino-4-(t-butoxycarbonylaminomethyl)benzene which was used without further purification.

EXAMPLE 11

The process described in Example 1 or Example 7 was repeated using the appropriate diphenylmethyl or t-butyl ester as starting material, and the following compounds were thus obtained:

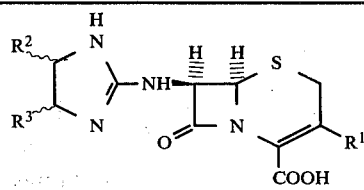

| R$^1$ | R$^2$ | R$^3$ | Footnotes |
|---|---|---|---|
| CH$_3$ | PhOCH$_2$ | H | 1, 2, 3 |
| CH$_3$ | Ph$_2$CH–⟨⟩–OCH$_2$ | H | 4, 5, 6 |
| CH$_3$ | CH$_3$ | H | 7, 2, 8 |
| CH$_2$OCOCH$_3$ | (CH$_3$)$_2$N–⟨⟩– | H | 9, 2, 10 |
| CH$_3$ | COOH | H | 11, 2, 12 |
| CH$_3$ | (CH$_3$)$_2$N–⟨⟩– | H | 13, 14, 15 |
| CH$_2$OCOCH$_3$ | H | H | 16, 2, 17 |
| CH$_3$ | H | H | 16, 2, 18 |
| CH$_2$S–[pyrimidine with CH$_3$, N, CH$_3$] | H | H | 19, 20, 21 |
| CH$_2$S–[thiadiazole with CH$_3$] | H | H | 16, 2, 22 |
| CH$_3$ | Cis-CH$_2$ | | 23, 24, 25 |
| CH$_2$OCOCH$_3$ | Cis-(CH$_2$)$_4$ | | 23, 2, 26 |

Footnotes
1. Reaction conducted in TFA/anisole.
2. Product purified by precipitation from a CH$_2$Cl$_2$/MeOH solution with ether.
3. The product had m.p. 137–145° (decomp.) and the following n.m.r. in d$_6$DMSO: - 2.02 (s, 3H); 3.2–4.5 (m, 9H); 5.1 (2d, 1H); 4.45 (m, 1H); 6.8–7.5 (m, 5H).
4. Reaction conducted in TFA only, using the same starting material as for the first compound in the Table. Under these conditions, the diphenylmethyl radical migrated, becoming attached to the benzene ring.
5. Product purified by chromatography on silica gel at −40° using CH$_2$Cl$_2$/MeOH/HOAc 78:20:2 v/v/v as eluant.
6. The product had m.p. 172–180° (decomp.) and the following n.m.r. in d$_6$DMSO: - 1.95 (s, 3H); 2.7–4.5 (m, 7H); 5.0 (m, 1H); 5.5 (m, 1H); 7.1 (m, 14H);
7. Reaction conducted in toluene/TFA 20:3 v/v for 30 minutes at ambient temperature.
8. Product had m.p. 160–164° and the following n.m.r. in CD$_3$COOD: - 1.35 (d, 3H); 2.13 (s, 3H); 3.28 (d, 1H); 3.59 (d, 1H); 4.2 (br, 3H); 5.12 (d, 2H); 5.3 (d, 1H);
9. Reaction conducted in TFA/anisole 10:1 v/v for 30 minutes at ambient temperature.
10. Product had the following n.m.r. in d$_6$DMSO: - 2.0 (s, 3H); 2.9 (s, 6H); 3.0–3.8 (br, exchangeable); 4.6–5.1 (br, 3H); 5.2 (s, 1H); 5.4–5.6 (q, 1H); 6.7 (d, 2H); 7.2 (d, 2H).
11. Reaction conducted in TFA/anisole 3:1 v/v at ambient temperature for 30 minutes.
12. Product, the TFA salt, had the following n.m.r. in d$_6$DMSO/TFA - 2.05 (s, 3H); 3.45 (q, 2H); 3.6–4.0 (m, 2H); 4.55 (m, 1H); 5.05 (d, 1H); 5.4 (dd, 1H); 9.55 (d, 1H).

-continued

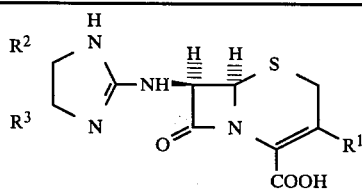

| R¹ | R² | R³ | Footnotes |

13. Reaction conducted in TFA/anisole 20:3 v/v at ambient temperature for 30 minutes.
14. Product isolated by evaporation of the reaction mixture and precipitation from MeOH solution with ether.
15. Product had m.p. >180° and the following n.m.r. in d₆DMSO: - 2.05 (s, 3H); 2.85 (s, 6H); 3.25–3.6 (m, 3H); 4.05 (t, 1H); 4.95 (s, 1H); 5.12 (d, 1H); 5.4–5.55 (q, 1H); 6.7 (d, 2H); 7.2 (d, 2H); 8.4–8.8 (m, 1H); 9.2 (m, 1H); 9.75 (d, 1H).
16. Reaction conducted in TFA/anisole 20:7 v/v at ambient temperature for 30 minutes.
17. Product had the following n.m.r. in d₆DMSO: - 2.0 (s, 3H); 3.5 (dd, 2H); 3.6 (s, 4H); 4.85 (dd, 2H); 5.1 (d, 1H); 5.55 (d, 1H); 9.9 (m, 1H).
18. Product had the following n.m.r. in d₆DMSO: - 2.07 (s, 3H); 3.5 (dd, 2H); 3.65 (s, 4H); 5.1 (d, 1H); 5.45 (d, 1H); 9.7 (m, 1H);
19. Reaction conducted in TFA/anisole 6:1.2 v/v at ambient temperature for 30 minutes.
20. Product isolated by precipitation from CH₂Cl₂/MeOH solution with EtOAc/ether.
21. Product had following n.m.r. in d₆DMSO: - 2.35 (s, 6H); 3.65 (m, 6H); 4.3 (dd, 2H); 5.1 (d, 1H); 5.45 (d, 1H); 6.95 (s, 1H).
22. Product had following n.m.r. in d₆DMSO: - 2.65 (s, 3H); 3.65 (s, 4H); 3.75 (dd, 2H); 4.4 (dd, 2H); 5.1 (d, 1H); 5.5 (dd, 1H); 9.5 (d, 1H).
23. Reaction conducted in TFA/toluene 3.6:2.3 v/v at ambient temperature for 40 minutes.
24. Product isolated by evaporation of reaction mixture and precipitation from CH₂Cl₂ solution with ether.
25. Product had m.p. 120-150° (decomp.) and the following n.m.r. in CD₃CO₂D: - 0.3 (m, 1H); 0.9 (m, 1H); 2.08 (s, 3H); 3.1–3.9 (m, 4H); 5.10 (d, 1H); 5.34 (d, 1H).
26. The infrared spectrum of the product (KBr disc) had the following absorptions: - 1775 cm⁻¹ (CO—NH); 1730 cm⁻¹ (COOH); 1650 cm⁻¹ (guanidinium).

The starting materials for use in the above process may be prepared by repeating the last part of Example 1 or the last part of Example 3 using the appropriate diamine. The following compounds were thus obtained:

TABLE II

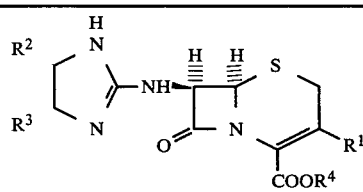

| R¹ | R² | R³ | R⁴ | Footnotes |
|---|---|---|---|---|
| CH₃ | PhOCH₂ | H | CHPh₂ | 1 |
| CH₃ | CH₃ | H | CHPh₂ | 2 |
| CH₂OCOCH₃ | (CH₃)₂N—⟨⟩— | H | CHPh₂ | 3 |
| CH₃ | Ph₂CHOOC | H | CHPh₂ | 4 |
| CH₃ | (CH₃)₂N—⟨⟩— | H | CHPh₂ | 5 |
| CH₃ | Cis-CH₂ | | t-C₄H₉ | 3,6 |

TABLE II-continued

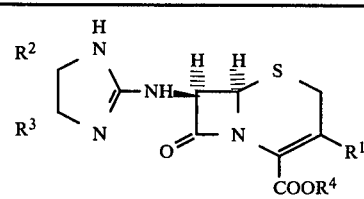

| R¹ | R² | R³ | R⁴ | Footnotes |
|---|---|---|---|---|
| CH₂OCOCH₃ | Cis-(CH₂)₄ | | CHPh₂ | 7 |

Footnotes

1. Product purified by chromatography on silica gel at −16° using CH₂Cl₂/MeOH 95:5 v/v as eluant. The product had m.p. 111–120° (decomp.).
2. Product purified by chromatography on silica gel at −30° using CH₂Cl₂/MeOH 90:8 v/v as eluant. Product then precipitated from CH₂Cl₂ solution with ether, m.p. 138–140°.
3. Product purified by chromatography on silica gel using CH₂Cl₂/MeOH 91:1 v/v as eluant.
4. Product purified by double chromatography on silica gel at −40° using CH₂Cl₂/MeOH 92:8 v/v as eluant.
5. Product purified by chromatography on silica gel at −45° using CH₂Cl₂/MeOH 9:1 v/v as eluant.
6. Product had m.p. 120–155° (decomp.)
7. Reaction mixture neutralised with TFA. Product purified by chromatography on silica gel at −20° using CH₂Cl₂/MeOH 95:5 v/v as eluant, and had the following n.m.r. in CDCl₃: - 1.7 (br, 8H); 2.0 (s, 3H); 3.45 (s, 2H); 3.8 (br, 2H); 4.9 (m, 3H); 5.3 (d, 1H); 6.85 (s, 1H); 7.2 (s, 10H).

Alternatively, the starting materials for use in the above process may be prepared as follows:

To a solution of t-butyl 3-acetoxymethyl-7-aminoceph-3-en-4-carboxylate (9.84 g.) in acetonitrile (350 ml.) was added 2-chloroimidazoline hydrochloride (4.23 g.) and the mixture was stirred under nitrogen for 6 hours at ambient temperature. The mixture was filtered, the precipitated solid washed with acetonitrile and the combined filtrates evaporated. The residue was purified by chromatography on silica gel (600 g.) at −40° using CH₂Cl₂/MeOH 9:1 v/v at eluate to give t-butyl 3-acetoxymethyl-7-(2-imidazolin-2-yl)aminoceph-3-em-4-carboxylate hydrochloride which was used without further purification.

In a similar manner, using the appropriate t-butyl 3-substituted-7-aminoceph-3-em-4-carboxylate, the following compounds were prepared:

TABLE III

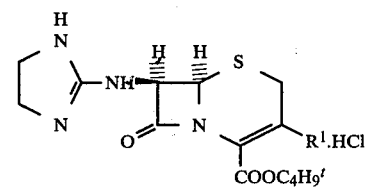

| R¹ | Footnotes |
|---|---|
| CH₃ | 1 |
| CH₂—S—⟨N=C(CH₃)—N=C(CH₃)—N⟩ | 2,3 |

TABLE III-continued

[Structure: cephem with H-N-(cyclic amidine)-NH- substituent at 7-position, S ring, CH2-R1, COOC4H9^t at 4-position]

| R¹ | Footnotes |
|---|---|
| CH₂—S—[thiadiazole with S, N—N, CH₃] | 1 |

Footnotes
1. Reaction carried out for 8 hours.
2. Reaction carried out at 40°.
3. Product purified by chromatography on silica gel at −40° using CH₂Cl₂/MeOH 96:4 v/v as eluant, followed by precipitation from CH₂Cl₂ solution with ether-/EtOAc 2:1 v/v.

The diphenylmethyl 2,3-diaminopropionate used as starting material may be obtained as follows:

A suspension of 2,3-diaminopropionic acid hydrobromide (3.7 g.) in distilled water (20 ml.) was stirred with toluene-p-sulphonic acid monohydrate (3.8 g.). After 30 minutes a clear solution was obtained. The water was removed by evaporation and the residue, after drying over P₂O₅, was suspended in DMF at 50°. A solution of diphenyldiazomethane in DMF was gradually added until a violet colour persisted. The DMF was evaporated at 60° and the residue precipitated from CH₂Cl₂ solution with ether. The precipitate was stirred in methanol with 2 equivalents of KOH. After 15 minutes the suspension was filtered through diatomaceous earth and the filtrate evaporated. The residue was dissolved in CH₂Cl₂, the solution filtered through a No. 4 sintered glass disc and the filtrate evaporated to dryness. The residue of the diphenylmethyl ester was triturated with petroleum ether to remove residual DMF.

The 1-(1,2-diaminoethyl)-4-dimethylaminobenzene used as starting material may be obtained as follows:

To a solution of sodium hydroxide (1.12 g.) in methanol (20 ml.) at 0° was added hydroxylamine hydrochloride (2.09 g.) dissolved in the minimum quantity of water. After a few minutes stirring the NaCl was filtered off and the filtrate added to a solution of 1-nitro-2-(4-dimethylaminophenyl)ethylene (5.0 g.) in methanol. After the reaction mixture had been stirred for 2 hours at ambient temperature a 20% excess of hydroxylamine solution was added, and stirring continued for a further 2 days. The suspension was filtered to give the product which was hydrogenated as a suspension in methanol under 4 Bars pressure in the presence of Raney nickel for 18 hours to give 1-(1,2-diaminoethyl)-4-dimethylaminobenzene as a brown oil.

The 2-chloroimidazoline hydrochloride may be obtained as follows:

A solution of barium chloride dihydrate (33.8 g.) in water (120 ml.) was added to a solution of 2-chloroimidazoline sulphate (28.0 g.) in water (85 ml.). The suspension was filtered through a No. 4 sintered glass disc and the filtrate evaporated at 55° to a fluid paste which was triturated several times with acetone to give a granular solid. This solid was dried over P₂O₅ to give the product, m.p. 170°–180°.

The t-butyl 7-amino-3-(4,6-dimethylpyrimid-2-yl)thiomethylceph-3-em-4-carboxylate used as an intermediate may be prepared as follows:

A solution of sodium bicarbonate (9.45 g.) in water (100 ml.) was added in portions to a stirred suspension of 3-acetoxymethyl-7-aminoceph-3-em-4-carboxylic acid (13.5 g.) in water (100 ml.) and acetone (50 ml.). The solid dissolved with effervescence. To this solution under nitrogen at 55° was added rapidly, drop by drop, a solution of 4,6-dimethyl-2-mercaptopyrimidine (10.5 g.) in water (100 ml.) and acetone (100 ml.), the pH being maintained between 7.4 and 7.8 by addition of 6 NHCl or 5% w/v aqueous NaHCO₃. After 23 hours at 55°, the reaction mixture was cooled to 0° and acidified to pH 4.0. The resulting precipitate was filtered, washed with water and acetone, and dried over P₂O₅ to give 7-amino-3-(4,6-dimethylpyrimid-2-yl)thiomethylceph-3-em-4-carboxylic acid. A mixture of this acid (3.52 g.) and O-t-butyl-1,3-diisopropylisourea (6.0 g.) in dry CH₂Cl₂ (60 ml.) was stirred under nitrogen for 20 hours. The reaction mixture was filtered, the filtrate evaporated and the residue purified by chromatography on silica gel (200 g.) at −40° using CH₂Cl₂/ether 6:4 v/v as eluant to give the t-butyl ester.

By repeating the reactions described immediately above, but using 2-methyl-5-mercapto-1,3,4-thiadiazole in place of 4,6-dimethyl-2-mercaptopyrimidine, there were obtained 7-amino-3-(2-methyl-1,3,4-thiadiazol-5-yl)thiomethylceph-3-em-4-carboxylic acid and the corresponding t-butyl ester.

EXAMPLE 12

The process used in example 1 or 7 was repeated using the appropriate diphenylmethyl or t-butyl ester as starting material, and the following compounds were obtained:

TABLE I

[Structure: cephem with H-N-(cyclic amidine)-NH- substituent at 7-position, S ring, CH2-R1, COOH at 4-position]

| R¹ | Footnotes |
|---|---|
| CH₂—S—[benzothiazole with S, N] fused ring | 1, 2, 3, 4 |
| CH₂—S—[benzoxazole with N, O] fused ring | 5, 6, 7, 8 |
| CH₂—S—[1-methyl-tetrazole N—N, N, N—CH₃] | 9, 10, 11, 12, 13 |
| CH₂—S—[benzothiazole S, N] fused ring | 14, 6, 15, 16 |

TABLE I-continued

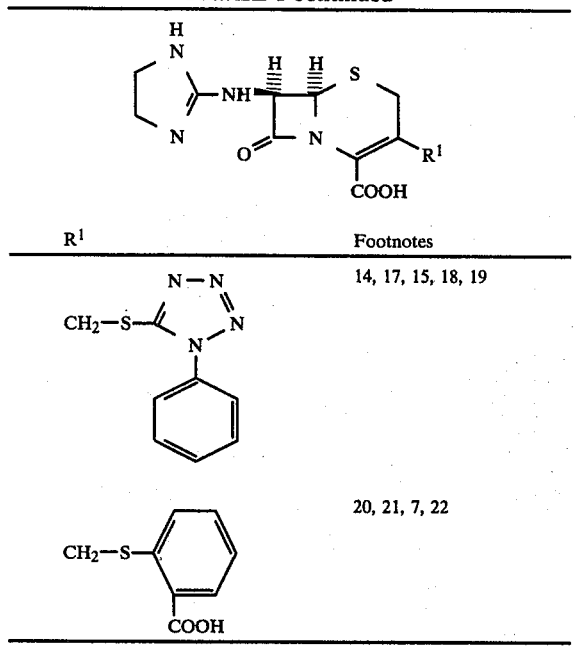

| $R^1$ | Footnotes |
|---|---|
| CH₂—S—[1-phenyl-tetrazol-5-yl] | 14, 17, 15, 18, 19 |
| CH₂—S—[2-carboxyphenyl] | 20, 21, 7, 22 |

Footnotes

1. Reaction conducted in TFA/anisole 2:1 v/v.
2. Reaction conducted for 90 minutes at ambient temperature.
3. product isolated by evaporation of the reaction mixture followed by addition of ether and filtration.
4. n.m.r. in CDCl₃ + CD₃OD: - 5.10 (d, 1H); 5.55 (d, 1H); 3.0–4.6 (m, 12H).
5. Reaction conducted in TFA/anisole 5:2 v/v.
6. Reaction conducted for 2 hours at ambient temperature.
7. Product isolated by evaporation followed by solution of the residue in the minimum amount of MeOH/CH₂Cl₂ and precipitation with ether.
8. n.m.r. in d₆DMSO + CD₃COOD: - 3.7 (s, 4H); 3.85 (dd, 2H); 4.55 (dd, 2H); 5.2 (d, 1H); 5.55 (d, 1H); 7.2–7.7 (m, 2H).
9. Reaction conducted in TFA/anisole 1:2 v/v.
10. Reaction conducted for 2.5 hours at ambient temperature.
11. Product isolated by evaporation followed by solution of residue in CH₂Cl₂ and precipitation by addition of this solution to ether. The precipitated product was dissolved in the minimum amount of CH₂Cl₂ and methanol. Crystallisation of the zwitterionic compound occurred.
12. Zwitterionic product had m.p. 200° and the following n.m.r. in CDCl₃/CD₃OD + TFA: - 3.75 (s, 2H); 3.8 (s, 4H); 4.0 (s, 3H); 4.36 (s, 2H); 5.06 (d, 1H); 5.46 (d, 1H).
13. The hydrochloride was obtained in addition of a solution of dry HCl in C₂H₅OH at a suspension of the zwitterion until solution; the solvent was evaporated and the residue dissolved in CH₂Cl₂—MeOH; this solution was poured into ether, and the resulting precipitate was filtered. The compound had following n.m.r. in CD₃OD: - 3.8 (s, 6H); 4.0 (s, 3H); 4.36 (s, 2H); 5.15 (d, 1H); 5.4 (d, 1H).
14. Reaction conducted in TFA/anisole 5:1 v/v.
15. Product isolated by evaporation, solution in MeOH and precipitation with ether.
16. Product had following n.m.r. in d₆DMSO: - 3.65 (s, 4H); 3.6–4.0 (m, 2H); 4.55 (dd, 2H); 5.1 (d, 1H); 5.5 (d, 1H); 7.3–8.0 (m, 4H).
17. Reaction conducted for 30 minutes at ambient temperature.
18. product had following n.m.r. in d₆DMSO + CD₃COOD: - 3.6–3.8 (m, 2H); 3.7 (s, 4H); 4.5 (dd, 2H); 5.15 (s, 1H); 5.55 (s, 1H); 7.7 (s, 5H).
19. Product was contaminated with a product having

TABLE I-continued

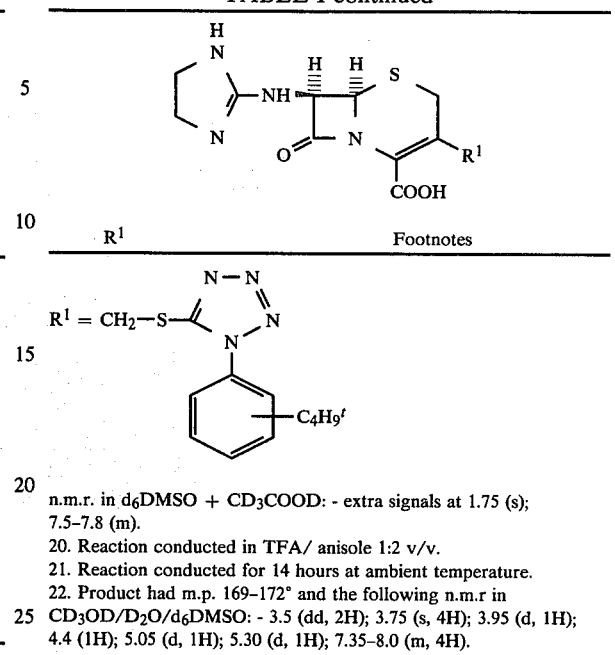

| $R^1$ | Footnotes |
|---|---|
| $R^1$ = CH₂—S—[1-(4-t-butylphenyl)tetrazol-5-yl] | n.m.r. in d₆DMSO + CD₃COOD: - extra signals at 1.75 (s); 7.5–7.8 (m). |

20. Reaction conducted in TFA/ anisole 1:2 v/v.
21. Reaction conducted for 14 hours at ambient temperature.
22. Product had m.p. 169–172° and the following n.m.r in CD₃OD/D₂O/d₆DMSO: - 3.5 (dd, 2H); 3.75 (s, 4H); 3.95 (d, 1H); 4.4 (1H); 5.05 (d, 1H); 5.30 (d, 1H); 7.35–8.0 (m, 4H).

The starting materials for use in the above process may be prepared by repeating a process similar to the process described for the synthesis of t-butyl 3-acetoxymethyl-7-(2-imidazolin-2-yl)aminoceph-3-em-4-carboxylate hydrochloride in the last part of Example 11 (i.e. reaction of 2-chloroimidazoline hydrochloride with t-butyl 3-acetoxymethyl-7-aminoceph-3-em-4-carboxylate). The following compounds were thus obtained:

TABLE II

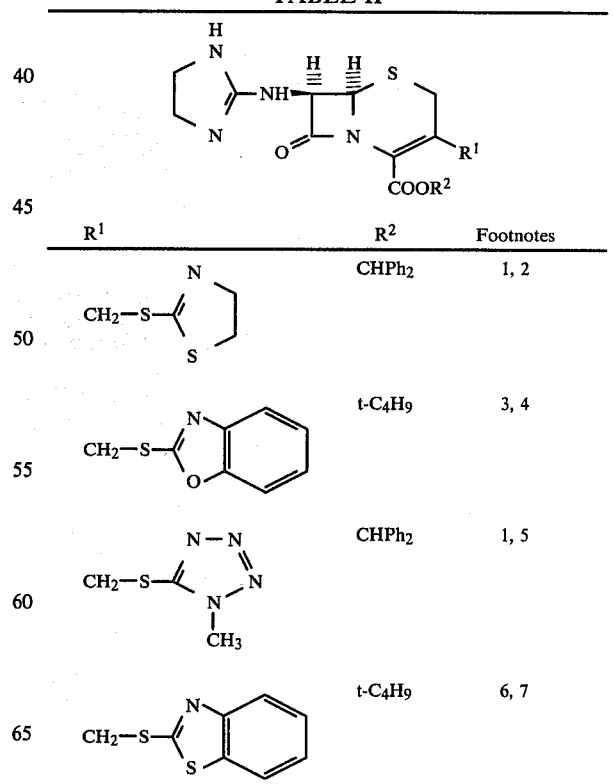

| $R^1$ | $R^2$ | Footnotes |
|---|---|---|
| CH₂—S—[4,5-dihydrothiazol-2-yl] | CHPh₂ | 1, 2 |
| CH₂—S—[benzoxazol-2-yl] | t-C₄H₉ | 3, 4 |
| CH₂—S—[1-methyl-tetrazol-5-yl] | CHPh₂ | 1, 5 |
| CH₂—S—[benzothiazol-2-yl] | t-C₄H₉ | 6, 7 |

TABLE II-continued

[Structure: cyclic amidine-NH-β-lactam-S with R¹ and COOR² substituents]

| R¹ | R² | Footnotes |
|---|---|---|
| CH₂—S—[1-phenyl-tetrazol-5-yl] | t-C₄H₉ | 8, 9 |
| CH₂—S—[2-(COOC₄H₉ᵗ)phenyl] | t-C₄H₉ | 1, 10 |

Footnotes

1. The reaction was carried out for 18 hours in acetonitrile at room temperature. The product was purified by chromatography on silica gel using $CH_2Cl_2$ containing increasing amounts of MeOH as eluant.
2. Product had the following n.m.r. in DMSO + $CH_3COOH$: - 3.55–4.1 (m, 2H); 3.7 (s, 2H); 3.65 (m, 2H); 4.0 (d, 1H); 4.4 (d, 1H); 5.35 (d, 1H); 5.75 (d, 1H); 7.0 (s, 1H); 7.2–7.6 (m, 10H).
3. Reaction carried out 6 hours at 50° in acetonitrile; product purified by chromatography on silica gel at −45°, eluting with $MeOH/CH_2Cl_2$ 3:97 v/v.
4. Product had the following n.m.r. in $CD_3OD$: - 1.5 (s, 9H); 3.75 (s, 4H); 3.8 (dd, 2H); 4.4 (dd, 2H); 5.1 (d, 1H); 5.4 (d, 1H); 7.2–7.6 (m, 4H).
5. Product had m.p. 135–137° and the following n.m.r. in $CDCl_3/CD_3OD$: - 3.75 (s, 2H); 3.8 (s, 4H); 3.9 (s, 3H); 4.3 (m, 2H); 5.25 (d, 1H); 5.65 (d, 1H); 6.9 (s, 1H); 7.2–7.5 (m, 10H).
6. Reaction carried out 6 hours at 40° in acetonitrile; product purified by chromatography on silica gel, eluant $CH_2Cl_2/MeOH$ 95:5 v/v.
7. Product had the following n.m.r. in $CD_3OD$: - 1.55 (s, 9H); 3.75 (dd, 2H); 3.8 (s, 4H); 4.55 (dd, 2H); 5.15 (d, 1H); 5.45 (d, 1H); 7.3–7.9 (m, 4H).
8. Reaction carried out 5 hours at 40°; product purified by chromatography at −40° on silica gel, eluant $MeOH/CH_2Cl_2$ 8:92, v/v.
9. Product had following n.m.r. in $CD_3OD$: - 1.5 (s, 9H); 3.75 (dd, 2H); 3.8 (s, 4H); 4.45 (dd, 2H); 5.1 (d, 1H); 5.45 (d, 1H); 7.6 (s, 5H).
10. Product had following n.m.r. in $d_6DMSO$: - 1.5 (s, 9H); 1.6 (s, 9H); 3.7 (s, 4H); 3.5–4.0 (dd, 2H); 4.0 (d, 1H); 4.2 (d, 1H); 5.35 (d, 1H).

Some of the appropriate t-butyl or diphenylmethyl 3-substituted-7-aminoceph-3-em-4-carboxylates used in the synthesis of the compounds described in Table II are listed in Table III.

TABLE III

[Structure: 7-amino-β-lactam-S with R¹ and COOR² substituents]

| R¹ | R² | Footnotes |
|---|---|---|
| CH₂—S—[2-thiazolin-2-yl] | CHPh₂ | 1 |
| CH₂—S—[benzoxazol-2-yl] | t-C₄H₉ | 2 |
| CH₂—S—[benzthiazol-2-yl] | t-C₄H₉ | 3 |
| CH₂—S—[1-phenyl-tetrazol-5-yl] | t-C₄H₉ | 4 |
| CH₂—S—[2-(COOC₄H₉ᵗ)phenyl] | t-C₄H₉ | 5 |

Footnotes

1. Product obtained by action of diphenyldiazomethane on 7-amino-3-(2-thiazolin-2-yl)thiomethylceph-3-em-4-carboxylic acid in solution in acetonitrile; compound had following n.m.r. in $CDCl_3$: - 3.35–4.1 (m, 4H); 3.6 (m, 2H); 3.95 (d, 1H); 4.4 (d, 1H); 4.81 (d, 1H); 4.95 (d, 1H); 7.05 (s, 1H); 7.2–7.7 (large s, 10H).
2. To a stirred suspension of 3-acetoxymethyl-7-aminoceph-3-em-4-carboxylic acid (19 g.) in a mixture of water (120 ml.) and acetone (120 ml.) was added gradually a slurry of 14 g. of $NaHCO_3$ in 80 ml. of water. The resulting solution was heated under $N_2$ atmosphere at 50°. Benzoxazole-2-thiol (15.9 g.) was added slowly, then the pH was adjusted to 7.5 and heating was continued 15 hours at 55° at that pH. After cooling the mixture was filtered. The filtrate was cooled with ice and adjusted to pH 4.4. The resulting precipitate was washed with water and acetone and dried over $P_2O_5$ to give 12.6 g. of 7-amino-3-(benzoxazol-2-yl)thiomethylceph-3-em-4-carboxylic acid. To a suspension of 5.45 g. of this compound in 90 ml. of THF was added 9 g. of freshly distilled O—t-butyl-N,N'—bisisopropylisourea. After 24 hours at ambient temperature the mixture was filtered and the filtrate concentrated and the residue purified by chromatography. IR (KBr) 3340 (w), 2980 (w), 1775 (s), 1710 (s), 1620.
3. Product obtained by action of O—t-butyl-N,N'—diisopropylisourea on 7-amino-3-(benzthiazol-2-yl)thiomethylceph-3-em-4-carboxylic acid in THF (see last part of footnote 2 for a similar process). Product had following n.m.r. in $CDCl_3$: - 1.55 (s, 9H); 1.8 (s, 2H); 3.65 (s, 2H); 4.45 (dd, 2H); 4.7 (d, 1H); 4.9 (d, 1H); 7.25 –7.95 (m, 4H).
4. To a 13.6 g. suspension of 3-acetoxymethyl-7-aminoceph-3-em-4-carboxylic acid in water (100 ml.) and acetone (50 ml.) was added a slurry of 10 g. of $NaHCO_3$ in 100 ml. of water. The solution was heated at

TABLE III-continued

[Structure: H₂N-substituted β-lactam with S, N, COOR², R¹ groups]

| R¹ | R² | Footnotes |
|---|---|---|

55° and 13.35 g. of 1-phenyl-1H—tetrazole-5-thiol was added portionwise. The pH was kept at 7.5 for 15 hours. After cooling the pH was adjusted to 2 and the precipitate was filtered, washed with water and acetone and dried under vaccum over $P_2O_5$ to give 9.36 g. of amino acid. To 4.22 g. of this acid was added 6.48 g. of O—t-butyl-N,N'—bisisopropylisourea. After 15 minutes 65 ml. of $CH_2Cl_2$ was added and the mixture was stirred for 18 hours. The reaction mixture was filtered, the filtrate was concentrated and the residue was dissolved in EtOAc, then washed with a 5% w/v aqueous $NaHCO_3$ then with water. After drying with $MgSO_4$ the solution was concentrated and the residue purified by chromatography. The product had the following n.m.r. in $CDCl_3$: - 1.5 (s, 9H); 3.65 (s, 2H); 4.4 (dd, 2H); 4.7 (d, 1H); 4.9 (d, 1H): 7.5 (s, 5H).
5. The compound was obtained according to a process similar to the process described in Footnote 2. The crude product was treated with a solution of dry HCl in MeOH and the crystalline product (m.p. 140–144°) was obtained as the hydrochloride without chromatography. It had the following n.m.r. in $CD_3OD$: - 1.5 (s, 9H); 1.6 (s, 9H); 3.7 (m, 2H): 3.95 (d, 1H): 4.4 (d, 1H); 5.0 (d, 1H); 5.2 (d, 1H); 7.3–7.9 (m, 4H).

EXAMPLE 13

The process described in Example 7 was repeated using the appropriate diphenylmethyl ester as starting material and the following compound was obtained:

[Structure showing OH-N imidazoline-NH-β-lactam with S, N, CH₂OCOCH₃, COOH]

Footnotes
1. The reaction was carried out for 5 munutes at ambient temperature in TFA/anisole 40:60 v/v.
2. The product was isolated by evaporation of the reaction mixture followed by solution in $CH_2Cl_2$/MeOH and precipitation with hexane.
3. Product had m.p. 230°(decomp.) and the following n.m.r. in d₆DMSO/CF₃COOD:- 2.0 (s, 3H); 3.6 (m, 6H); 4.7 (d, 1H); 5.0 (d, 1H); 5.1 (d, 1H); 5.5 (d, 1H).

The starting material used in the above process may be obtained by the following process:

To a stirred suspension of 2.06 g. of N-hydroxy-1,2-diaminoethane dihydrobromide (2.06 g.) in methanol (5 ml.) was added 2 equivalents of KOH in methanol. The reaction mixture was added to a stirred solution of 1.76 g. of diphenylmethyl 3-acetoxymethyl-7-dibromomethyleneaminoceph-3-em-4-carboxylate (1.76 g.) in dry THF (80 ml.) cooled at −30°. After 2 hours, TFA (0.7 ml.) was added. The mixture was concentrated to dryness, then $CH_2Cl_2$ was added. The mixture was filtered, the filtrate was concentrated and dried and the residue purified by chromatography on silica gel, eluting with $CH_2Cl_2$ containing 0, 1 and 2% v/v of MeOH. The product had the following n.m.r. in d₆DMSO+CD₃CO₂D: 2.0 (s, 3H); 3.6 (m, 6H); 4.7 (d, 1H); 4.9 (d, 1H); 5.2 (d, 1H); 5.6 (d, 1H); 6.9 (s, 1H); 7.2–7.5 (m, 10H).

EXAMPLE 14

The process described in Example 1 was repeated using the appropriate starting materials, and the following compounds were thus obtained:

TABLE I

[Structure showing R-substituted dihydroimidazoline-NH-β-lactam with S, N, CH₃, COOH]

| R | Footnotes |
|---|---|
| phenyl | 1, 2, 3, 4, |
| biphenyl-4-yl | 1, 5, 6 |
| 4-cyanophenyl (NC-C₆H₄-) | 7, 8, 9 |
| 4-chlorophenyl (Cl-C₆H₄-) | 10, 11, 12, |
| 2-chlorophenyl | 1, 11, 13, |
| 3-hydroxyphenyl (HO-C₆H₄-) | 7, 14, 15, |
| 3,4-dihydroxyphenyl | 7, 14, 16 |

Footnotes
1. Reaction conducted in TFA/toluene.
2. Product purified by precipitation from $CH_2Cl_2$ solution with ether. The precipitated salt was dissolved in MeOH and treated with epoxypropane to give the zwitterionic form which crystallised. The zwitterionic form was converted to a hydrochloride salt by treatment with a solution of HCl in MeOH and precipitation with ether.
3. The product, the hydrochloride salt, had m.p. 171° (decomp.) and had the following n.m.r. in d₆DMSO/CD₃CO₂D:- 2.1 (s, 3H); 3.54 (q, 2H); 3.2–3.8 (m, 3H); 4.1 (t, 1H); 5.15 (d, 1H); 5.2 (t, 1H); 5.6 (d, 1H); 7.4 (s, 5H).
4. This compound has the (6R, 7S, 11R) configuration.
5. Product purified by precipitation from $CH_2Cl_2$ solution with ether. This operation was repeated once.
6. The product, the hydrobromide/trifluoroacetate

TABLE I-continued

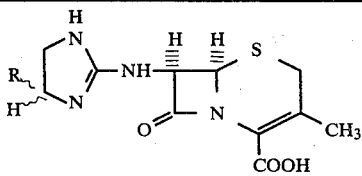

| R | Footnotes |
|---|---| salt, had m.p. 172-175° (decomp.) and the following
n.m.r. in d₆DMSO/CD₃CO₂D:- 2.05 (s, 3H); 3.55 (q, 2H);
3.1-3.8 (m, 1H); 4.2 (m, 1H); 5.1 (d, 1H); 5.2 (m, 1H);
5.9 (d, 1H); 7.38-7.8 (m, 9H).
7. Reaction conducted in TFA/anisole.
8. The TFA/anisole was evaporated and the
compound isolated by pouring a solution of the compound
in CH₂Cl₂/MeOH (1:1 v/v) into ether and filtering the
precipitated powder.
9. The product, mainly the trifluoroacetate salt,
had m.p. 178-185° (decomp.) and had the following
n.m.r. in d₆DMSO/CD₃OD:- 2.15 (s, 3H); 3.3-3.8 (m, 3H);
4.0-4.4 (m, 1H); 5.0-5.7 (m, 3H); 7.8-8.0 (m, 4H).
10. Reaction conducted in TFA/toluene at room
temperature for 2 hours.
11. Product isolated by precipitation from MeOH
solution with ether.
12. The product, the hydrobromide/trifluoracetate
salt, had m.p. 172-176° (decomp.) and the following
n.m.r. in d₆DMSO/CD₃CO₂D:- 2.05 (s, 3H); 3.4 (m, 3H);
3.5 (q, 2H); 4.12 (m, 1H); 5.1 (d, 1H); 5.15 (m, 1H);
5.5 (d, 1H); 7.45 (m, 4H).
13. The product, the hydrobromide/trifluoroacetate
salt, had m.p. 178-185° (decomp.) and the following
n.m.r. in d₆DMSO/CD₃CO₂D:- 2.05 (s, 3H); 3.47 (q, 2H);
3.2-3.7 (m, 1H); 4.2 (t, 1H); 5.08 and 5.1 (2d, 1H);
5.25-5.6 (m, 2H); 5.4 (m, 4H).
14. Product isolated by evaporating the TFA/
anisole solution in vacuo. The residue was purified by
precipitation from a CH₂Cl₂/MeOH solution with ether.
15. The product, the trifluoroacetate salt, had
the following n.m.r.in d₆DMSO:- 1.9 (s) and 2.05 (s)
(total = 3H); 3.2-3.6 (m, 3H); 4.1 (t, 1H); 5.0 (m, 1H);
5.1 (d, 1H); 5.45 (d, 1H); 6.7-7.4 (m, 4H).
16. The product, the trifluoroacetate salt, had
the following n.m.r.in d₆DMSO/CD₃COOD:- 2.3 (s, 3H);
3.4-3.85 (m, 3H); 4.2 (t, 1H); 5.05-5.20 (m, 1H); 5.30
(d, 1H); 5.7 (d, 1H); 6.7-7.1 (m, 3H).

The starting materials for use in the above process may be prepared by repeating the last part of Example 1 or the last part of Example 3 using the appropriate arylethylenediamine. The following compounds were thus obtained:

TABLE II

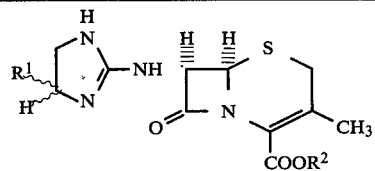

| R¹ | R² | Footnotes |
|---|---|---|
| (phenyl) | t-C₄H₉ | 1, 2, 3, 4, 5, 18 |
| (biphenyl) | t-C₄H₉ | 2, 3, 6, 7, 18 |
| 4-NC-C₆H₄ | CHPh₂ | 8, 9, 10 |
| 4-Cl-C₆H₄ | t-C₄H₉ | 11, 3, 6, 12, 18 |
| 2-Cl-C₆H₄ | t-C₄H₉ | 2, 3, 6, 13, 18 |
| 4-HO-C₆H₄ | t-C₄H₉ | 11, 14, 15, 18 |
| 2,4-(HO)₂-C₆H₃ | t-C₄H₉ | 11, 16, 17, 18 |

Footnotes
1. Product prepared using (R)-phenylethylene-
diamine obtained from the dihydrochloride salt
($[\alpha]_D^{20}$ + 28°, H₂O, c=4.1) by treatment with sodium
methoxide in methanol.
2. Reaction was carried out in THF at room
temperature.
3. The reaction mixture was neutralised with HBr/
MeOH.
4. Product purified by precipitation from MeOH
solution with ether.
5. The product had m.p. 145-150°, $[\alpha]_D^{20}$ + 102°
(ethanol) and had the following n.m.r. in d₆ DMSO:-
1.5 (s, 9H); 2.0 (s,3H); 3.5 (q,2H); 3.2-3.8 (m, 3H);
4.1 (t, 1H); 5.1 (d, 1H); 5.15 (t, 1H); 5.45 (d, 1H);
7.3 (s,5H).
6. The product was purified by precipitation from
CH₂Cl₂ solution with ether.
7. The product had m.p. 165-170° and the following
n.m.r. in d₆ DMSO/CD₃CO₂D:- 1.5 (s,9H); 2.02(s,3H); 3.55
(q,2H); 3.1-3.7 (m,1H); 4.2 (t,1H); 5.2 (d,1H); 5.1-
5.4 (m,1H); 5.65 (d,1H); 7.2-7.9 (m,9H).
8. Reaction was carried out in THF at -78°.
9. Product pruified by chromatography on silica
gel at -40° using CH₂Cl₂/MeOH 9:1 v/v as eluant.
10. Product had m.p. 123-132° and the following
n.m.r. in CD₃OD:- 2.19 (s,3H); 3.3-3.6 (m,3H); 4.1-4.6
(m,1H); 5.1-5.6(m,3H); 6.9 (s,1H); 7.2-8.0 (m,14H).
11. Reaction carried out in THF at 0°.
12. Product had m.p. 140-155° and the following
n.m.r. in d₆ DMSO:- 1.5 (s,9H); 2.05 (s, 3H); 3.55
(q, 2H); 3.2-3.6 (m,1H); 4.15 (t,1H); 5.15 (d,1H);
5.2 (m,1H); 5.6 (d, 1H); 7.2-7.6 (m, 4H).
13. Product had m.p. 152-157° and the following
n.m.r. in d₆ DMSO/CD₃CO₂D:- 1.5 (s,9H); 2.05 (s,3H);
3.52 (q,2H); 3.2-3.7 (m, 1H); 4.05 (t, 1H); 5.2 (d,1H);
5.45 (m,1H); 5.6 (d,1H); 7.5 (m,4H).
14. Product was purified by chromatography on

TABLE II-continued

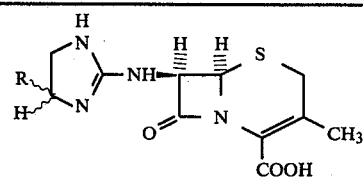

| $R^1$ | $R^2$ | Footnotes |
|---|---|---|

Footnotes silica gel at $-20°$ using MeOH/CH$_2$Cl$_2$ 2:98 v/v as eluant.
15. The product had the following n.m.r. in CD$_3$OD:- 1.55 (s,9H); 2.05 (s) and 2.15 (s) (3H); 3.0-3.9 (m,3H), 4.15 (t,1H); 5.0-5.2 (m,1H); 5.15 (d,1H); 5.4 (d,1H); 6.7-7.4 (m,4H).
16. Product purified by chromatography in silica gel at $-20°$ using CH$_2$Cl$_2$/MeOH 97:3 v/v then 95:5 v/v as eluant.
17. The product had the following n.m.r. in d$_6$ DMSO/CD$_3$COOD:- 1.55 (s,9H); 2.1 (s,3H); 3.6 (m,1H); 3.7 (q,2H); 4.2 (t,1H); 5.05-5.25 (m,1H); 5.34 (d,1H); 5.73 (d,1H); 6.8-7.05 (m,3H).
18. The dibromoisonitrile required as starting material may be preparedas follows:-
A solution of t-butyl 7-amino-3-methyylceph-3-em-4-carboxylate (47.7 g.) in CH$_2$Cl$_2$ solution (500 ml.) was treated dropwise, with stirring and under a nitrogen blanket, with formic-acetic anhydride (13 ml.). The solution was then concentrated under vacuum to give a solid foam. Purification was effected by filtering a CH$_2$Cl$_2$ solution of the product through 20 times its own weight of magnesium silicate. Evaporation of the filtrate gave 44 g. of t-butyl 7-formamidoceph-3-em-4-carboxylate as a white solid foam, n.m.r. (CDCl$_3$):- 1.52(s,9H); 2.10 (s,3H); 3.15-3.56(q, 2H); 4.94 (d,1H); 5.80 (dd, 1H); 7.2 (d, 1H, exchangeable); 8.25 (s,1H).

To a solution of t-butyl 7-formamidoceph-3-em-4-carboxylate (5 g.) in a mixture of toluene (100 ml.) and CH$_2$Cl$_2$ (10 ml.) cooled to $-78°$ was added pyridine (2.72 ml.), followed by the dropwise addition of a 1.9M solution of phosgene in toluene (8.84 ml). The mixture was stirred for 30 minutes at $-78°$ and then pyridine (2.72 ml.) and 1.9M phosgene in toluene (8.84 ml.) were again added. Thirty minutes later additional pyridine (1.35 ml.) and 1.9M phosgene in toluene (4.4 ml.) were added. The precipitate was removed by filtration and washed with toluene. The combined filtrates were evaporated to dryness at room temperature under vacuum. The residue was filtered through 20 times its own weight of magnesium silicate using CH$_2$Cl$_2$ as solvent. Evaporation of the filtrate gave a crystalline solid. Recrystallisation from ether/light petroleum gave 3.1 g. (66%) of t-butyl 3-methyl-7-isocyanoceph-3-em-4-carboxylate, m.p. 144°-151°. The n.m.r. spectrum in CDCl$_3$ had the following resonances: 1.50 (s,9H); 2.15 (s,3H); 3.20-3.55 (q,2H); 7.88 (d,1H); 5.15 (d,1H).

To a solution of t-butyl 3-methyl-7-isocyanoceph-3-em-4-carboxylate (1.4 g.) in a mixture of dry toluene (30 ml.) and dry CH$_2$Cl$_2$ (3 ml.) cooled to $-78°$ under a nitrogen atmosphere was added dropwise with stirring a solution of bromine (0.256 ml.) in dry CH$_2$Cl$_2$ (3 ml.). The addition lasted 10 minutes and the solution was then stirred for a further 20 minutes at $-78°$ and then concentrated to an oil in vacuo. The oil was triturated with light petroleum to give a crystalline mass which was then filtered to give t-butyl 3-methyl-7-dibromomethyleneaminoceph-3-em-4-carboxylate, m.p. 101°-103° (77%). The product had the following n.m.r. (CDCl$_3$): 1.54 (s,9H); 2.1 (s,3H); 3.26 (q,2H); 4.92 (d,1H); 5.15 (d,1H).

EXAMPLE 15

The process described in Example 1 was repeated using the appropriate starting materials and the following compounds were obtained:

TABLE I

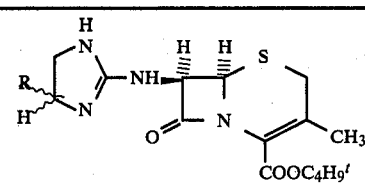

| R | Footnotes |
|---|---|
| CH$_3$(CH$_2$)$_5$ | 1, 2, 3 |
| HOCH$_2$ | 4, 5, 6 |
| H$_2$NC(=O) | 1, 7, 8 |

Footnotes
1. Reaction conducted in TFA/toluene at room temperature.
2. Product purified by precipitation from CH$_2$Cl$_2$ solution with ether.
3. The product, the hydrated hydrobromide/ trifluoroacetate salt, had m.p. 110° (decomp.) and the following n.m.r. in CD$_3$CO$_2$D:- 0.88 (m, 3H); 1.34 (m, 10H); 2.12 (s, 3H); 3.2-3.8 (q, 2H); 5.22 (d, 1H); 5.55 )d, 1H).
4. Reaction conducted in TFA/anisole at 0° for 5 minutes, then at room temperature for 6 hours.
5. Product purified by trituration with ether.
6. Product, the trifluoroacetate salt, had m.p. 145-147° and the following n.m.r. in CDCl$_3$/CD$_3$OD:- 2.25 (s, 3H); 3.4-3.55 (m, 2H); 3.55-4.0 (m, 5H); 5.15 (d, 1H); 5.4 (d, 1H).
7. Product purified by precipitation from MeOH solution withn ether.
8. The product, the hydrobromide trifluoroacetate salt, had m.p. 180° (decomp.) and the following n.m.r. in D$_2$O:- 2.0 (s, 3H); 3.15-3.65 (q, 2H); 3.75 (dd, 1H); 4.05 (dd, 1H); 5.15 (d, 1H); 5.35 (d, 1H).

The starting materials for use in the above processes may be prepared by repeating the last part of Example 1 or the last part of Example 3 using the appropriate diamines as starting materials. The following compounds were thus obtained:

TABLE II

| R | Footnotes |
|---|---|
| CH$_3$(CH$_2$)$_5$ | 1 |
| HOCH$_2$ | 2 |
| H$_2$NC(=O) | 3 |

Footnotes
1. Reaction carried out in THF under a nitrogen atmosphere at 0° for 1 hour. The product was purified by medium pressure chromatography on silica gel at $-20°$ using CH$_2$Cl$_2$/MeOH/HOAc 97:3:1 v/v/v as eluant. The product was obtained as a yellow foam after evaporation of solvents and had the following n.m.r. in CD$_3$OD:- 0.9 (m, 3H); 1.1-1.8 (m, 19H); 2.12 (s, 3H); 3.2-4.2 (m, 5H); 5.12 (d, 1H); 5.36 (d, 1H).
2. Reaction was carried out in THF at room temperature for 6 hours. The product was purified

TABLE II-continued

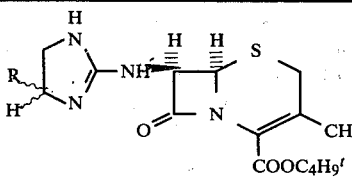

| R | Footnotes |
| --- | --- | by low temperature chromatography on silica gel using CH$_2$Cl$_2$/MeOH/HOAc 94:6:6 v/v/v as eluant, and then by precipitation from CH$_2$Cl$_2$ solution with light petroleum. The product had m.p. 121–124° and had the following n.m.r. in d$_6$DMSO:- 1.5 (s, 9H); 2.05 (s, 3H); 3.0–4.2 (m, 7H); 5.15 (d, 1H); 5.45 (d, 1H).
3. Reaction was carried out in THF under a nitrogen atmosphere at room temperature. The product was purified by low temperature medium pressure chromatography on silica gel using CH$_2$Cl$_2$/MeOH/HOAc 45:3:2 v/v/v as eluant and then by precipitation from MeOH solution with ether. The product had m.p. 190° (decomp.) and had the following n.m.r. in CDCl$_3$/CD$_3$CO$_2$D:- 1.52 (s, 9H); 2.08 (s, 3H); 3.3–3.8 (q, 2H); 5.15 (d, 1H); 5.45 (d, 1H).

EXAMPLE 16

The process described in Example 1 was repeated using the appropriate t-butyl ester as starting material and the following compounds were obtained:

TABLE I

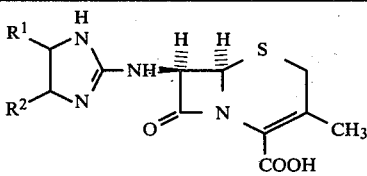

| R$^1$ | R$^2$ | Footnotes |
| --- | --- | --- |
| | cis (CH$_2$)$_2$ | 1, 2, 3 |
| | cis CH$_2$CH=CH | 1, 2, 4 |
| cis CO$_2$CH$_3$ | cis CO$_2$CH$_3$ | 1, 2, 5 |
| cis C$_6$H$_5$ | cis C$_6$H$_5$ | 1, 6 |

Footnotes
1. Reaction conducted in TFA/toluene.
2. Product purified by precipitation from MeOH solution with ether.
3. Product, the mixed hydrobromide/trifluoroacetate salt, had m.p. 160° (decomp.) and the following n.m.r. in d$_6$DMSO:- 2.1 (s, 3H); 2.0–2.4 (m, 4H); 3.25–3.72 (q, 2H); 4.2–4.6 (m, 2H); 5.15 (d, 1H); 5.3 (d, 1H).
4. The product, the mixed hydrobromide/trifluoroacetate salt, had m.p. 170° (decomp.) and the following n.m.r. in d$_6$DMSO:- 2.1 (s, 3H); 2.6 (m, 2H); 3.15–3.85 (q, 2H); 4.5–5.1 (m, 2H); 5.15 (d, 1H); 5.35 (d, 1H); 5.8 (brd, 1H); 6.05 (brd, 1H).
5. The product, the mixed hydrobromide/trifluoroacetate salt, had m.p. 155° (decomp.) and the following n.m.r. in CD$_3$CO$_2$D:- 2.27 (s, 3H); 3.5 (br, 2H); 3.8 (s, 6H); 5.15 (s, 2H); 5.27 (d, 1H); 5.62 (d, 1H).
6. The product was purified by precipitation from CH$_2$Cl$_2$ solution with ether. The product, the hemihydrate of the mixed hydrobromide/trifluoroacetate salt, had m.p. 196–199° and the followinf n.m.r. in CD$_3$CO$_2$D:- 2.11 (s, 3H); 3.41–3.7 (q, 2H); 5.19 (d, 1H); 5.56 (d, 1H); 7.05 (m, 10H).

The starting materials for the above process may be prepared by repeating the last part of Example 1 or the last part of Example 3 using the appropriate diamines. The following compounds were thus obtained:

TABLE II

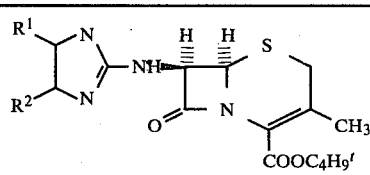

| R$^1$ | R$^2$ | Footnotes |
| --- | --- | --- |
| | cis (CH$_2$)$_2$ | 1, 2, 3 |
| | cis CH$_2$CH=CH | 1, 4 |
| cis CO$_2$CH$_3$ | cis CO$_2$CH$_3$ | 1, 5 |
| cis C$_6$H$_5$ | cis C$_6$H$_5$ | 1, 6 |

Footnotes
1. Reaction was carried out in THF under a nitrogen atmosphere for 3 hours at ambient temperature.
2. Product was purified by medium pressure chromatography on silica gel using CH$_2$Cl$_2$/MeOH/HOAc 92:4:4 v/v/v as eluant.
3. The product had m.p. 145° (decomp.) and the following n.m.r. in CD$_3$OD:- 1.52 (s, 9H); 2.1 (s, 3H); 2.15–2.8 (m, 4H); 3.12–3.8 (q, 2H); 4.5 (m, 2H); 5.12 (d, 1H); 5.35 (d, 1H).
4. The product was purified by medium pressure chromatography on silica gel using CH$_2$Cl$_2$/MeOH 95:5 v/v as eluant and further purified by precipitation from CH$_2$Cl$_2$ solution with ether. The product had m.p. 136° and the following n.m.r. in d$_6$DMSO/D$_2$O:- 1.55 (s, 9H); 2.1 (s, 3H); 2.6 (m, 2H); 3.25–3.85 (q, 2H); 4.5–5.1 (m, 2H); 5.18 (d, 1H); 5.4 (d, 1H); 5.8 (br, 1H); 6.1 (br, 1H).
5. The product was purified by low temperature medium pressure chromatography on silica gel eluted with CH$_2$Cl$_2$/MeOH 96:4 v/v. The oil obtained after evaporation of the solvents was purified by precipitation from CH$_2$Cl$_2$ with ether. The product, m.p. 125° (decomp.), had the following n.m.r. in d$_6$DMSO:- 1.5 (s, 9H); 2.02 (s, 3H); 3.2–3.8 (q, 2H); 3.7 (s, 6H); 4.9 (s, 2H); 5.12 (d, 1H); 5.54 (d, 1H).
6. The product was purified by low temperature medium pressure chromatography on silica gel eluted with EtOAc/MeOH 95:5 v/v and then by precipitation from CH$_2$Cl$_2$ solution with ether. The product had m.p. 190° (decomp.) and the following n.m.r. in CDCl$_3$/CD$_3$OD:- 1.56 (2, 9H); 2.07 (s, 3H); 3.2–3.35 (q, 2H); 5.09 (d, 1H); 5.45 (d, 1H); 5.55 (s, 2H); 7.06 (m, 10H).

EXAMPLE 17

The process described in Example 1 was repeated using the appropriate diphenylmethyl ester as starting material and the following compounds were obtained:

TABLE I

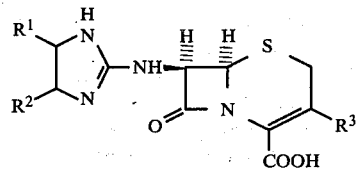

| R$^1$ | R$^2$ | R$^3$ | Footnotes |
| --- | --- | --- | --- |
| H | H | 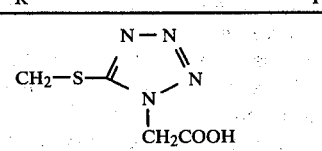 | 1, 2 |
| cis CH$_2$ | | 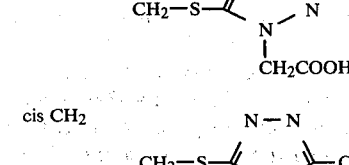 | 1, 3 |

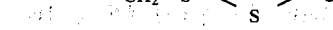

TABLE I-continued

[Structure: R¹,R² substituted imidazoline-NH-β-lactam-cephem with COOH and R³]

| R¹ | R² | R³ | Footnotes |
|---|---|---|---|
| cis CH₂ | | CH₂—[N—N / N(CH₃)—N tetrazole] | 1, 4 |

Footnotes
1. Reaction was conducted in TFA/anisole.
2. Product was purified by precipitation from MeOH/CH₂Cl₂ solution with ether. The product thus obtained was a mixture of the trifluoroacetate salt and the zwitterionic form. It had the following n.m.r. spectrum in CD₃OD/D₂O/DCl:- 3.80 (m, 6H); 4.3 (d, 1H); 4.5 (d, 1H); 5.2 (d, 1H); 5.3 (s, 2H); 5.5 (d, 1H).
3. Product was purified by precipitation from MeOH solution with ether, and had m.p. 150° (decomp.). The product, the mixed hydrobromide/trifluoroacetate salt, had the following n.m.r. spectrum in d₆DMSO/CD₃CO₂D/TFA:- 0.25 (m, 1H); 0.80 (m, 1H); 2.65 (s, 3H); 3.2–3.8 (m, 4H); 4.25 and 4.5 (q, 2H); 5.1 (d, 1H); 5.4 (d, 1H).
4. The product was purified by precipitation from MeOH solution, containing a little TFA, with ether. The product, the mixed hydrobromide trifluoroacetate salt, had m.p. 165° (decomp.) and the following n.m.r. in d₆DMSO/CD₃CO₂D:- 0.25 (m, 1H); 0.8 (m, 1H); 3.6 (m 4H); 3.9 (s, 3H); 4.25 (br, 2H); 5.05 (d, 1H); 5.4 (d, 1H).

The starting materials for the above process are described in the following Table II:

TABLE II

[Structure: R¹,R² substituted imidazoline-NH-β-lactam-cephem with COOCHPh₂ and R³]

| R¹ | R² | R³ | Footnotes |
|---|---|---|---|
| H | H | CH₂—S—[tetrazole-N(CH₂COOCHPh₂)] | 1 |
| cis CH₂ | | CH₂—S—[thiadiazole-CH₃] | 2 |
| cis CH₂ | | CH₂—S—[tetrazole-N(CH₃)] | 3 |

Footnotes
1. This compound was prepared by reacting 2-chloroimidazoline hydrochloride and diphenylmethyl 7-amino-3-(1-diphenylmethoxycarbonylmethyl-1H—tetrazol-5-yl)thiomethylceph-3-em-4-carboxylate in a process similar to that described in the second part of Example 12. The reaction was carried out in acetonitrile at

TABLE II-continued

[Structure: R¹,R² substituted imidazoline-NH-β-lactam-cephem with COOCHPh₂ and R³]

| R¹ | R² | R³ | Footnotes |
|---|---|---|---|

40° for 4.5 hours. Purification was effected by chromatography on silica gel eluting first with CH₂Cl₂/ether 1:1 v/v to remove the bulk of unreacted starting material. CH₂Cl₂/acetone/isopropanol 6:2:2 v/v/v was then used to elute first a small amount of starting material in salt form and then the desired product. The product had m.p. 130–132° and the following n.m.r. in CDCl₃:- 4.2 (br, 6H); 5.2 (d, 1H); 5.7 (d, 1H); 6.88 (s, 1H); 6.9 (s, 1H); 7.3 (m, 10H). The bisdiphenylmethyl ester used as starting material was prepared as follows:- To a suspension of 7-amino-3-(1-carboxymethyl-1H—tetrazol-5-yl)ceph-3-em-4-carboxylic acid (7 g.) in acetonitrile/MeOH 1:1 v/v; (200 ml.) at 50° was slowly added a solution of diphenyldiazomethane in hexane until a permanent violet colour was obtained. The hot reaction mixture was filtered. The residue was washed with hot acetonitrile and the combined filtrates were concentrated in vacuo. The crystalline product thus obtained had m.p. 162–164° and the following n.m.r. in d₆DMSO:- 3.55 (s, 2H); 4.05 (d, 1H); 4.35 (d, 1H); 4.8 (d, 1H); 4.9 (d, 1H); 5.5 (s, 2H); 6.85 (s, 2H); 7.3 (s, 10H).
2. This compound was prepared by repeating the process described in the last part of Example 1 using the appropriate starting materials. The reaction was carried out in THF at room temperature. The product was purified by low temperature chromatography on silica gel using mixture of CH₂Cl₂ and MeOH as eluant. The product obtained was dissolved in CH₂Cl₂ and precipitated with ether. The product had m.p. 125° (decomp.) and the following n.m.r. in d₆DMSO:- 0.25 (m, 1H); 0.85 (m, 1H); 2.62 (s, 3H); 3.4–3.9 (m, 2H); 4.35 (q, 2H); 5.19 (d, 1H); 5.5 (m, 1H); 6.85 (s, 1H); 7.3 (m, 10H); 9.4 (m, 3H).
3. This compound was prepared by repeating the processes described in the last part of Example 1 using the appropriate starting materials. The reaction was carried out in THF. The product was purified as in Footnote 2. The product had m.p. 132° (decomp.) and the following n.m.r. in d₆DMSO/CD₃CO₂D:- 0.3 (m, 1H); 0.9 (m, 1H); 3.4–4.0 (m, 8H); 4.2 and 4.4 (q, 2H); 5.2 (d, 1H); 5.5 (d, 1H); 6.9 (s, 1H); 7.38 (m, 10H).

EXAMPLE 18

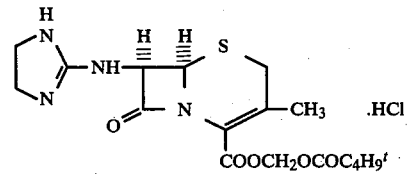

A solution of pivaloyloxymethyl 3-methyl-7-aminoceph-3-em-4-carboxylate toluene-p-sulphonate (3 g.) in water (100 ml.) was treated with an excess of NaHCO₃. The mixture was extracted 3 times with ethyl acetate and the combined extracts were washed with brine and concentrated. The residue (2 g.) was dissolved in acetonitrile (75 ml.) and 2-chloro-2-imidazoline hydrochloride (0.86 g.) was added. The mixture was stirred at 40° for 5 hours, filtered and the filtrate concentrated. The residue was recrystallised from isopropanol/ether to give pivaloyloxymethyl 3-methyl-7-(2-imidazolin-2-yl)aminoceph-3-em-4-carboxylate hydrochloride (0.99 g.) having the following n.m.r. in CD₃OD: 1.2 (s, 9H); 2.15 (s, 3H); 3.55 (dd, 2H); 3.8 (s, 4H); 5.15 (d, 1H); 5.4 (d, 1H); 5.85 (dd, 2H).

EXAMPLE 19

The process used in Example 1 or 7 was repeated using the appropriate diphenylmethyl or t-butyl ester as starting material, and the following compounds were obtained:

TABLE I

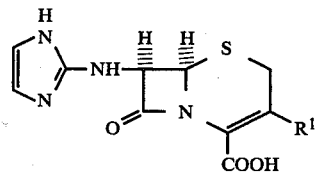

| $R^1$ | Footnotes |
|---|---|
| CH₂—S—[tetrazole]—CH₂CH₂N(CH₃)₂ | 1, 2, 3, 4, 5 |
| CH₂—S—[tetrazole]—CH₃ | 1, 6, 3, 7 |
| CH₃OCOCH₃ | 8, 9, 3, 10 |
| CH₂—S—[thiadiazole]—CH₃ | 8, 9, 3, 11 |
| CH₂—S—[tetrazole, H] | 1, 9, 3, 12 |
| CH₂—S—[phenyl-COOH] | 1, 13, 3, 14 |
| CH₂—S—[tetrazole]—CH₂COOH | 1, 13, 3, 15 |

Footnotes
1. Reaction conducted in TFA/anisole 1:1 v/v.
2. Reaction conducted at ambient termperature for 2 hours.
3. Product isolated by evaporation in vacuo and trituration of residue with ether.
4. Product purified by preparative HPLC.
5. Product had the following n.m.r. in D₂O:- 3.10 (s, 6H); 3.6–4.0 (m, 4H); 4.2 (m, 2H); 4.9 (m, 2H); 5.3–5.5 (2d, 2H); 6.9 (s, 2H).
6. Reaction conducted at ambient temperature for 5 minutes.
7. Product had m.p. 120–125° and the following n.m.r. in d₆DMSO:- 3.7 (m, 2H); 3.9 (s, 3H); 4.3 (m, 2H); 5.15 (d, 1H); 5.5 (dd, 1H); 7.0 (s, 2H); 9.4 (d, 1H).
8. Reaction conducted in TFA.
9. Reaction conducted at ambient temperature for 30 minutes.
10. Product had m.p. 150–160° and the following TABLE I-continued n.m.r. in d₆DMSO:- 2.1 (s, 3H); 3.3–3.9 (m, 2H); 4.8 (d, 1H). 5.15 (d, 1H); 5.3 (d, 1H); 5.7 (d, 1H); 7.1 (s, 2H); 9.4 (d, 1H).
11. Product had m.p. 140–145° and the following n.m.r. in d₆DMSO:- 2.6 (s, 3H); 3.4 (d, 1H); 3.8 (d, 1H); 4.2 (d, 1H); 4.5 (d, 1H); 5.1 (d, 1H); 5.5 (dd, 1H); 6.9 (s, 2H); 9.2 (s, 1H).
12. Product had m.p. 145–150° and the following n.m.r. in d₆DMSO:- 3.5 (d, 1H); 3.8 (d, 1H); 4.0 (m, 2H); 5.1 (d, 1H); 5.5 (dd, 1H); 7.05 (s, 2H); 7.2 (m, 1H); 7.9 (s, 1H); 9.3 (d, 1H).
13. Reaction conducted at ambient temperature for 15 minutes.
14. Product had m.p. 175–180° and the following n.m.r. in d₆DMSO + CD₃COOD:- 3.5 (d, 1H); 3.8 (d, 1H); 4.0 (d, 1H); 4.3 (d, 1H); 5.2 (d, 1H); 5.6 (d, 1H); 7.0 (s, 2H); 7.2–8.0 (m, 3H).
15. Product had the following n.m.r. in CD₃OD + D₂O:- 3.65 (d, 1H); 3.9 (d, 1H); 4.3 (d, 1H); 4.5 (d, 1H); 5.25 (d, 1H) 5.25 (s, 2H); 5.5 (dd, 1H); 7.0 (s, 2H).

The starting materials for use in the above process may be prepared as follows:

To a suspension of 16 g. of 7-amino-3-[(1-methyl-1H-tetrazol-5-yl)thiomethyl]ceph-3-em-4-carboxylic acid (see Example 5) (16.0 g.) in THF (250 ml.) was added dropwise a 70% w/v perchloric acid solution (3.77 ml.). After 45 minutes at ambient temperature a solution of diphenyl diazomethane (11.2 g.) in THF (50 ml.) was slowly added to the above solution. After stirring overnight, the mixture was poured into ether (2 l.) and the mixture filtered. The solid was treated with an excess of an aqueous solution of NaHCO₃ and extracted three times with CH₂Cl₂. The combined extracts were dried over MgSO₄, filtered, and evaporated to yield 19 g. of a solid material which was purified by chromatography over silica gel (800 g.), using CH₂Cl₂/ether 5:5 v/v as eluant. There was thus obtained diphenylmethyl 3-[(1-methyl-1H-tetrazol-5-yl)thiomethyl]ceph-3-em-4-carboxylate as a white crystalline solid (5.4 g.). To a solution of diphenylmethyl 3-[(1-methyl-1,2,3,4-tetrazol-5-yl)thiomethyl]ceph-3-em-4-carboxylate (2.47 g.) in acetonitrile (30 ml.) was added 2-fluoroimidazole HCl (0.615 g.). The mixture was stirred at reflux under nitrogen for 1.5 hours. The solvent was then evaporated, and the residue chromatographed on silica gel (150 g.) using CH₂Cl₂/ethanol/HOAc 90:10:5 v/v/v as eluant. The purified compound thus obtained was dissolved in the minimum of CH₂Cl₂ and precipitated with ether to give diphenylmethyl 7-(imidazol-2-yl)-3-[(1-methyl-1-H-tetrazol-5-yl)thiomethyl]ceph-3-em-4-carboxylate as a beige solid (1 g.) which had m.p. 125°–130° and the following n.m.r. in CD₃OD: 3.75 (m, 2H); 3.85 (s, 3H); 4.25 (m, 2H); 5.1–5.7 (m, 2H); 6.8 (s, 2H); 6.85 (s, 1H); 7.3 (m, 10H).

The following starting materials were similarly obtained:

TABLE II

[Structure: imidazole-NH-β-lactam-S-cephem with COOR² and R¹ substituent]

| R¹ | R² | Footnotes |
|---|---|---|
| CH₂—S—[tetrazole with CH₂CH₂N(CH₃)₂] | CHPh₂ | 1, 2, 3 |
| CH₂OCOCH₃ | t-C₄H₉ | 4, 5, 6 |
| CH₂—S—[thiadiazole-CH₃] | t-C₄H₉ | 4, 7, 8, 9 |
| CH₂—S—[1,2,3-triazole, H] | CHPh₂ | 10, 11, 12, 13 |
| CH₂—S—[phenyl-COOCHPh₂] | CHPh₂ | 14, 4, 15, 16 |
| CH₂—S—[tetrazole with CH₂COOCHPh₂] | CHPh₂ | 17, 18, 19 |

1. The starting material may be obtained as follows:-
A suspension of 7-amino-3-(1-[2-dimethylaminoethyl]-1H—tetrazol-5-yl)thiomethylceph-3-em-4-carboxylic acid (5.0 g.) in a mixture of methanol (170 ml.) and CHCl₃ (80 ml.) and heated under reflux. A CHCl₃ solution of diphenyldiazomethane was then added slowly until a permanent red colour was observed, then 1N HCl (50 ml.) was added. The mixture was evaporated, water (50 ml.) was added to the remaining aqueous phase, which was then extracted with ethyl acetate (50 ml.). The aqueous phase was separated, cooled to 0° and neutralized to pH 7 with a 20% w/v aqueous ammonia solution. The procipitate was collected, washed with water and MeOH to give diphenylmethyl 7-amino-3-(1-[2-dimethylaminoethyl]-1H—tetrazol-5-yl)thiomethylceph-3-em-4-carboxylate (2.9 g.) having the following n.m.r. in CDCl₃:- 2.3 (s, 6H); 2.7 (m, 2H); 3.7 (m, 2H); 4.2 (m, 4H); 4.7 (q, 2H).
2. Reaction of 1 equivalent of aminoester with 2.2 equivalents of 2-fluoroimidazole hydrochloride.
3. Reaction conducted in a MeOH/CHCl₃ 1:1 v/v at reflux for 15 hours. The product was used without purification in the next step.
4. Reaction conducted in CH₃CN at reflux for 2 hours.
5. Product isolated by chromatography over silica gel at −20° using CH₂Cl₂/ethanol/HOAc 95:5:2 v/v/v as eluant.
6. Product had the following n.m.r. in CDCl₃ + CD₃OD:- 1.6 (s, 9H); 2.15 (s, 3H); 3.3 (d, 1H); 3.7 (d, 1H); 4.8 and 5.15 (2d, 2H); 5.25 (d, 1H); 5.7 (d, 1H): 6.8 (s, 2H).
7. Product purified by chromatography on silica gel using CH₂Cl₂/ethanol/HOAc, 85:15:5 v/v/v as eluant and precipitated with pentane as a mixture of salts.
8. Product had the following n.m.r. in CDCl₃:-
1.5 (s, 9H); 2.95 (s, 3H); 3.9 (m, 2H); 4.45 (m, 2H); 5.4 (d, 1H); 6.0 (dd, 1H); 6.9 (s, 2H); 8.6 (d, 1H).
9. Condensation could also be performed in a mixture of CH₃CN/DMF 3:1 v/v.
10. The starting material may be obtained as follows:-
7-amino-3-(1,2,3-triazol-4-yl)thiomethylceph-3-em-4-carboxylic acid (13.7 g.) was suspended in a mixture of CH₃CN (150 ml.) and methanol (150 ml.). An excess of diphenyldiazomethane (18 g.) in CH₃CN (100 ml.) was added to the mixture, which was then heated at 40° for 8 hours and stirred overnight at room temperature. The reaction mixture was filtered, evaporated and the residue chromatographed over silica gel, 400 g., using CH₂Cl₂/ether/MeOH 20:79:1: v/v/v as eluant to give diphenylmethyl-7-amino-3-(1,2,3-triazol-4-yl)thiomethyl-ceph-3-em-4-carboxylate (8.3 g.).
11. Reaction conducted in a mixture of CH₃CN (30 ml.) and THF (5 ml.) under reflux for 2 hours.
12. The product was purified by chromatography over silica gel at −20° using CH₂Cl₂/ether/ethanol/HOAc 40:40:15:5 v/v/v/v as eluant. The product was precipitated from a solution in the minimal amount of CH₂Cl₂/methanol with ether.
13. The product had the following n.m.r. in CDCl₃/CD₃OD:- 3.5 (m, 2H); 3.9 (m, 2H); 5.1 (d, 1H); 5.5 (d, 1H); 6.6 (s, 2H); 6.8 (s, 1H); 7.4 (m, 10H); 7.6 (s, 1H).
14. The starting material may be obtained as follows:-
A mixture of 7-amino-3-(2-carboxy)phenylthiomethylceph-3-em-4-carboxylic acid (11 g.) and diphenyldiazomethane (15 g.) in CH₃CN (300 ml.) was stirred at ambient temperature for 60 hours under N₂. The remaining insoluble starting material was removed by filtration, the solution was evaporated and the residue was purified by chromatography over silica gel, using CH₂Cl₂/ether 8:2 v/v eluant to give diphenylmethyl 7-amino-3-(2-diphenyl-methoxycarbonylphenyl)thiomethylceph-3-em-4-carboxylate (8.6 g.).
15. Product purified by chromatography over silica gel using CH₂Cl₂/ethanol/HOAc 95:5:5 as eluant. The product was precipitated from a solution in the minimal amount of CH₂Cl₂/methanol with pentane.
16. Product had the following n.m.r. in CDCl₃:-
3.5 (m, 2H); 4.0 (m, 2H); 5.1 (d, 1H); 5.6 (d, 1H); 6.6 (s, 2H); 6.9 (s, 1H); 7.2–7.4 (m, 24H).
17. Condensation performed in CH₃CN/DMF 8:1 v/v under argon at reflux for 6 hours.
18. Product purified by chromatography over silica gel using CH₂Cl₂/ether/MeOH 50:50:2 v/v/v as eluant.
19. Product had the following n.m.r. in CDCl₃ + CD₃OD:- 3.5 (d, 1H); 3.85 (d, 1H); 4.1 (d, 1H); 4.3 (d, 1H); 5.15 (d, 1H); 5.2 (s, 2H); 5.4 (dd, 1H); 6.6 (s, 2H); 6.9 (s, 2H); 7.1–7.5 (m, 20H).

EXAMPLE 20

The process used in Example 1 or 7 was repeated using the appropriate diphenylmethyl or t-butyl ester as starting material, and the following compounds were thus obtained:

TABLE I

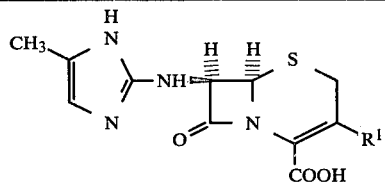

| R¹ | Footnotes |
|---|---|
| CH₃ | 1, 2, 3, 4 |
|  CH₂—S—(N—N, S, CH₃) | 1, 5, 3, 6 |
|  CH₂—S—(H, N—N, N) | 7, 5, 3, 8 |

Footnotes
1. Reaction conducted in TFA.
2. Reaction conducted at ambient temperature over 2 hours.
3. Product isolated by trituration with ether.
4. Product had the following n.m.r. in d₆DMSO:- 2.1 (s, 3H); 2.15 (s, 3H); 3.3 (d, 1H); 3.6 (d, 1H); 5.1 (d, 1H); 5.5 (m, 1H); 6.7 (s, 1H); 9.1 (m, 1H);
5. Reaction conducted at ambient temperature for 30 minutes.
6. Product had the following n.m.r. in d₆DMSO:- 2.1 (s, 3H); 2.7 (s, 3H); 3.6 (d, 1H); 3.8 (d, 1H); 4.2 (d, 1H); 4.5 (d, 1H); 5.2 (d, 1H); 5.5 (dd, 1H); 6.7 (s, 1H); 9.2 (d, 1H).
7. Reaction conducted in TFA/anisole 1:1 v/v.
8. Product had the following n.m.r. in d₆DMSO + CD₃CO₂D:- 2.0 (s, 3H); 3.4–3.7 (m, 2H); 3.7–4.1 (m, 2H); 5.2 (d, 1H); 5.6 (d, 1H); 6.7 (s, 1H); 7.9 (s, 1H).

The starting material used in the above process may be obtained by the process described in the second part of Example 19 using 2-fluoro-4-methylimidazole hydrochloride and the appropriate 7-aminocephalosporin ester. The following compounds were thus obtained:

TABLE II

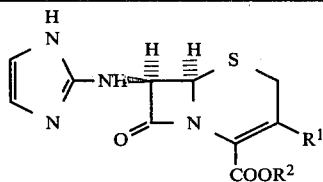

| R¹ | R² | Footnotes |
|---|---|---|
| CH₃ | t-C₄H₉ | 1, 2, 3 |
|  CH₂—S—(N—N, S, CH₃) | t-C₄H₉ | 4, 5, 6 |
| 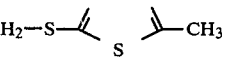 CH₂—S—(H, N—N, N) | CHPh₂ | 7, 8, 9 |

Footnotes
1. Reaction conducted in CH₃CN at reflux for 2.5 hours
2. The compound was purified by chromatography over silica gel, using CH₂Cl₂/ethanol/HOAc 90:5:5 v/v/v followed by 85:10:5 v/v/v as eluants. The product was precipitated from CH₂Cl₂ solution with ether.
3. Product had following n.m.r. in CDCl₃:- 1.4 (s, 9H); 2.05 (s, 3H); 2.1 (s, 3H); 3.0–3.6 (m, 2H); 5.0 (d, 1H); 5.5 (d, 1H); 6.25 (d, 1H).
4. Reaction conducted in a mixture of CH₃CN/DMF 2:1 v/v at 80–90° for 1.5 hours.
5. Product purified by chromatography on silica gel using CH₂Cl₂/ethanol/HOAc 85:10:5 v/v/v as eluant, followed by solution in the minimum amount of CH₂Cl₂ and precipitation with pentane. The free base was obtained

TABLE II-continued

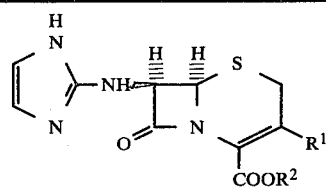

| R¹ | R² | Footnotes |
|---|---|---| by treatment with aqueous bicarbonate, extraction with EtOAc and concentration of the organic extracts.
6. The free base had the following n.m.r. in d₆DMSO:- 1.5 (s, 9H); 2.0 (s, 3H); 2.7 (s, 3H); 3.2–3.8 (m, 2H); 4.0–4.6 (m, 2H); 5.15 (d, 1H); 5.6 (d, 1H); 6.2 (s, 1H).
7. Reaction conducted in CH₃CN/DMF 4:1 v/v at 80–90°.
8. The product was purified by chromatography on silica gel using CH₂Cl₂/ethanol/HOAc 85:10:5 v/v/v as eluant. The product was dissolved in CH₂Cl₂/MeOH 97:3 v/v, the solution filtered and the filtrate evaporated. The residue was treated with aqueous bicarbonate, extracted with EtOAc/ethanol 97:3 v/v and the extract evaporated to dryness to give the free base having the following n.m.r. in d₆DMSO + CD₃CO₂D:- 2.0 (s, 3H); 3.4–4.0 (m, 4H); 5.2 (d, 1H); 5.4 (d, 1H); 6.4 (s, 1H); 6.8 (s, 1H); 7.3 (m, 10H); 7.8 (s, 1H).

EXAMPLE 21

The process used in Example 1 or 7 was repeated using the appropriate diphenylmethyl ester as starting material, and the following compounds were thus obtained:

TABLE I

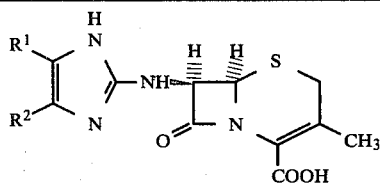

| R¹ | R² | Footnotes |
|---|---|---|
| CH₃ | CH₃ | 1, 2, 3, 4 |
| Ph | CH₃ | 5, 6, 7 |
| CH₃ | H | 1, 8, 3, 9 |

Footnotes
1. Reaction conducted in anisole/TFA 5:2 v/v.
2. Reaction conducted at ambient temperature for 30 minutes.
3. The product was purified by solution in the minimum CH₂Cl₂/MeOH and precipitated with ether-hexane.
4. Product, the trifluoroacetate salt, had the following n.m.r. in d₆DMSO:- 2.05 and 2.1 (2s, 9H); 3.40–3.60 (2d, 2H); 5.1 (d, 1H); 5.4 (d, 1H).
5. Reaction conducted at ambient temperature for 1 hour in anisole/TFA 5:1 v/v.
6. The product was purified by solution in CH₂Cl₂ and precipitation with diisopropyl ether.
7. Product, the trifluoroacetate salt, had the following n.m.r. in d₆DMSO:- 2.06 (s, 3H); 2.28 (s, 3H); 3.35–3.60 (2d, 2H); 5.18 (d, 1H); 5.65 (d, 1H); 7.2–7.6 (m, 5H); 8.2 (m, 1H);.
8. Reaction conducted between 0° and ambient temperature for 30 minutes.
9. Product, the mixed hydrobromide/trifluoroacetate salt, had the following n.m.r. in d₆DMSO:- 2.08 (s, 3H); 2.10 (s, 3H); 3.30–3.60 (2d, 2H); 5.10 (d, 1H); 5.48 (d, 1H); 6.55 (s, 1H).

The starting materials for use in the above process may be obtained as follows:

The second part of Example 9 was repeated using the appropriate starting materials and the following compounds were thus obtained:

TABLE II

R²—(OH on N)—N=C(NH—)—... structure with COOCHPh₂

| R¹ | R² | Footnotes |
|---|---|---|
| CH₃ | CH₃ | 1, 2, 3 |
| PH | CH₃ | 4, 5, 6 |
| CH₃ | H | 7, 8 |

Footnotes
1. To a solution of anti 2-amino-3-oximinobutane (3.1 g.) in THF (60 ml.) were added trimethylchlorosilane (7.75 ml.) and triethylamine (8.5 ml.) and the mixture was stirred at ambient temperature overnight. The precipitated trimethylamine HCl was removed by filtration under nitrogen, and the resulting solution was added to a cooled (−40°) solution of 7-dibromomethyleneamino cephalosporin derivative (5.6 g.) in THF (20 ml.). After one hour at −40° TFA (7 ml.) was added to the cold solution which was then concentrated under vacuum.
2. Product purified by chromatography over silica gel at low temperature, using $CH_2Cl_2$/MeOH 99:2 v/v as eluant.
3. Product had the following n.m.r. in $CDCl_3$:-
2.0 and 2.1 (2s, 9H); 3.1 (s, 2H); 5.0 (d, 1H); 5.7 (d, 1H); 6.9 (s, 1H); 7.1–7.5 (m, 10H).
4. 3 equivalents of anti 1-phenyl-1-oximino-2-aminopropane were added to a cold (0°) solution of 7-dibromomethyleneamino cephalosporin derivative in THF. Afer a few minutes at 0°, 3 equivalents of TFA were added to the reaction mixture, and the solvent evaporated under vacuum.
5. Product purified by chromatography over silica gel at −10° using $CH_2Cl_2$/MeOH/HOAc 98.5:1:0.5 v/v/v as eluant.
6. Product had the following n.m.r. in $d_6DMSO$:-
2.12 (s, 2H); 2.2 (s, 3H); CH₂S signals obscured by solvent peak, 5.22 and 5.7 (2d, 2H); 6.85 (s, 1H); 7.2–7.7 (m, 15H).
7. Synthesis described in Example 9.
8. Product had the following n.m.r. in $d_6DMSO$:-
2.04 (s, 6H); 3.5 (s, 2H); 5.14–5.58 (2d, 2H); 6.26 (s, 1H); 6.86 (s, 1H); 7.32 (m, 10H).

The second last part of Example 9 (reduction of the 1-hydroxy-imidazole derivative with titanium trichloride) was then repeated using the compounds listed in Table II as starting materials and the following compounds were thus obtained:

TABLE III

| R¹ | R² | Footnotes |
|---|---|---|
| CH₃ | CH₃ | 1, 2, 3 |
| Ph | CH₃ | 4, 5, 6 |
| CH₃ | H | 7, 8, 9 |

Footnotes
1. Reaction conducted in methanol with 2.5 equivalents of $TiCl_3$ at 40–50° for 30 minutes.
2. Product purified by low temperature chromatography on silica gel using $CH_2Cl_2$/MeOH/HOAc 90:5:5 v/v/v as eluant.
3. Product, the trifluoroacetate salt, had the

TABLE III-continued following n.m.r. in $d_6DMSO$:- 1.8 and 2.0 (2s, 9H); 3.55 (s, 2H); 5.25 (d, 1H); 5.60 (d, 1H); 6.90 (s, 1H); 7.30 (s, 10H).
4. Reaction conducted in MeOH/THF 1:1 v/v with 2 equivalents of $TiCl_3$ at 50° for few minutes.
5. Product purified by chromatography on silica gel at low temperature using $CH_2Cl_2$/MeOH/HOAc 98.5:1:0.5 v/v/v as eluant followed by precipitation of the product from $CH_2Cl_2$ solution with hexane.
6. Product, the trifluoroacetate salt, had the following n.m.r. in $d_6DMSO$:- 2.05 (s, 3H); 2.30 (s, 3H); 3.55 (s, 2H); 5.3 (d, 1H); 5.9 (d, 1H); 6.85 (s, 1H); 7.2–7.7 (m, 15H).
7. Reaction conducted in MeOH with 2 equivalents of $TiCl_3$ at 40–45° for 30 minutes.
8. Product purified by low temperature chromatography on silica gel using $CH_2Cl_2$/MeOH/HOAc 90:5:5 v/v/v as eluant. Product, the mixed hydrobromide/trifluoroacetate salt had the following n.m.r. in $d_6DMSO$:- 2.08 (s, 3H); 2.1 (s, 3H); 3.35–3.65 (2d, 2H); 5.15 (d, 1H); 5.65 (d, 1H); 6.45 (s, 1H); 6.88 (s, 1H); 7.15–7.6 (m, 10H).

EXAMPLE 22

The process described in Example 1 was repeated using the appropriate starting materials, the following compounds were thus prepared:

TABLE I

| R¹ | R² | R³ | R⁴ | Footnotes |
|---|---|---|---|---|
| CH₂OCOCH₃ | H | CH₂OH | H | 1, 2, 3 |
| CH₂OCOCH₃ | H | Me | H | 4, 5, 6 |
| CH₂OCOCH₃ | H | (CH₂)₄ | | 4, 7, 8, 9 |
| CH₂OCOCH₃ | OH | H | Ph | 1, 10, 11, 12 |
| CH₂—S—(N—N/S thiadiazole)—CH₃ | H | CH₃ | CH₃ | 13, 2, 14 |
| CH₂OCOCH₃ | H | Ph | H | 4, 5, 2, 15 |

Footnotes
1. Reaction conducted in anisole/TFA 1:1 v/v at 0°.
2. Product isolated by precipitation from minimum $CH_2Cl_2$/MeOH solution with ether.
3. Product, the hemitrifluoroacetate, had the following n.m.r. in $d_6DMSO$:- 2.0 (s, 3H); 3.4 and 3.65 (2d, 2H); 4.3 (s, 2H); 4.75 and 5.05 (2d, 2H); 5.15 (d, 1H); 5.7 (m, 1H); 6.8 (s, 1H).
4. Reaction conducted in anisole/TFA 1:1 v/v at ambient temperature.
5. Reaction conducted for 15–30 minutes.
6. Product, the trifluoroacetate salt, had the following n.m.r. in $d_6DMSO$:- 2.1 (s, 3H); 2.2 (s, 3H); 3.7 (s, 2H); 4.9 (d, 1H); 5.2 (d, 1H); 5.3 (d, 1H); 5.7 (m, 1H); 6.8 (s, 1H).

TABLE I-continued

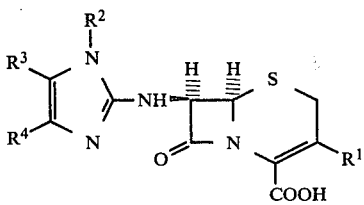

| R¹ | R² | R³ | R⁴ | Footnotes |
|---|---|---|---|---|

7. Reaction conducted for 15 minutes.

8. Product purified by precipitation from solution in the minimum of $CH_2Cl_2$/MeOH with hexane.

9. Product, the trifluoroacetate salt, had the following n.m.r. in $d_6$DMSO:- 1.7 (m, 4H); 2.0 (s, 3H); 2.4 (m, 4H); 3.4–3.5 (m, 2H); 4.7 (d, 1H); 5.05 (d, 1H); 5.1 (d, 1H); 5.5 (d, 1H).

10. Reaction conducted for 30 minutes at 0° and then 1 hour at ambient temperature.

11. Product purified by precipitation from solution in the minimum $CH_2Cl_2$/MeOH with ether-hexane.

12. Product, the trifluoroacetate salt, had the following n.m.r. in $d_6$DMSO + $CD_3COOD$:- 2.0 (s, 3H); 3.5–3.6 (m, 2H); 4.7 (d, 1H); 5.0 (d, 1H); 5.2 (d, 1H); 5.7 (d, 1H); 7.0 (s, 1H); 7.1–7.7 (m, 5H).

13. Reaction conducted in TFA/anisole 2:1 v/v for two minutes at ambient temperature.

14. Product, the trifluoroacetate salt, had the following n.m.r. in $d_6$DMSO:- 2.04 (s, 6H); 2.67 (s, 3H); 3.68 (2d, 2H); 4.26–4.56 (2d, 2H); 5.16–5.48 (2d, 2H).

15. Product, the trifluoroacetate salt, had the following n.m.r. in $d_6$DMSO:- 2.0 (s, 3H); 3.5–3.6 (q, 2H); 4.7 (d, 1H); 5.0 (d, 1H); 5.2 (d, 1H); 5.8 (d, 1H); 7.3 (s, 1H); 7.2–7.8 (m, 5H); 8.4–8.7 (m, 1H).

The starting materials for use in the above process may be obtained as follows:
The second part of Example 9 was repeated using the appropriate starting materials and the following compounds were thus obtained:

TABLE II

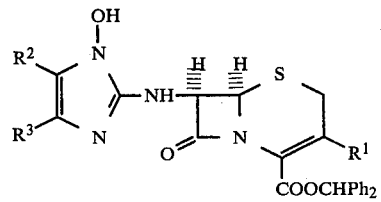

| R¹ | R² | R³ | Footnotes |
|---|---|---|---|
| $CH_2OCOCH_3$ | $CH_2OH$ | H | 1, 2, 3, 4, 5 |
| $CH_2OCOCH_3$ | $CH_3$ | H | 6, 3, 7, 8 |
| $CH_2OCOCH_3$ | $(CH_2)_4$ | | 9, 3, 10, 11 |
| 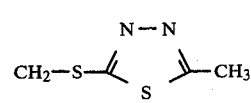 | $CH_3$ | $CH_3$ | 12, 10, 13 |

TABLE II-continued

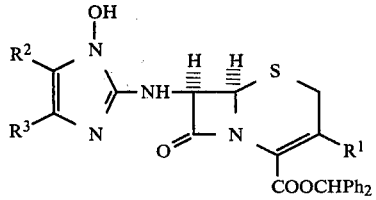

| R¹ | R² | R³ | Footnotes |
|---|---|---|---|
| $CH_2OCOCH_3$ | Ph | H | 14, 3, 10, 16, 15 |

Footnotes

1. The 1-amino-3-hydroxy-2-oximinopropane used as a starting material was obtained from Br—$CH_2$—CO—$CH_2$OH by displacement of the Br atom with 1.1 equivalents of potassium pthalimide in DMF at ambient temperature. The pthalimido derivative was purified by silica gel chromatography and then treated with $NH_2OH.HCl$ in a pyridine-ethanol mixture at 50° and finally, after purification of the oxime by crystallisation, hydrazinolysis with one equivalent of hydrazine at 50° in ethanol overnight, addition of 1 equivalent of 1N HCl and crystallisation of the hydrochloride from ethanol. The free base was obtained by treatment of a solution of the hydrochloride with 1 equivalent of KOH at 0°, the solution was then used for condensation (see footnote 2).

2. Condensation performed in THF/MeOH 10:1 v/v between −35° and −5° for 2 hours.

3. Reaction mixture worked up by addition of 2 equivalents of TFA and evaporation of the mixture.

4. Product purified by chromatography on silica gel at −15° using $CH_2Cl_2$/MeOH/HOAc 92:4:4 v/v/v as eluant.

5. Product had the following n.m.r. in $d_6$DMSO: - 1,8 (s, 3H); 3.2 (m, 2H); 4.25 (s, 2H); 4.56 (s, 2H); β lactam protons hidden by solvent: 6.23 (s, 1H) 6.85 (s, 1H); 7.3 (m, 10H).

6. Condensation performed in THF/MeOH 10:1 v/v at −40°.

7. Product purified by chromatography on silica gel, using $CH_2Cl_2$/MeOH/HOAc 98.5:1:0.5 as eluant.

8. Product had: IR (KBr) $vcm^{-1}$: 1785, 1740–1730 1665.

9. Condensation performed with 1-trimethylsilyl-amino-2-trimethylsiloxyimino-cyclohexane (prepared from 1-amino-2-oximinocyclohexane) in anhydrous THF at ambient temperature for 2.5 hours.

10. Product purified by chromatography on silica gel at low temperature using $CH_2Cl_2$/MeOH 98:2 v/v as eluant.

11. Product had the following n.m.r. in $CDCl_3$: - 1.6–2.6 (m, 8H); 2.0 (s, 3H); 3.3–3.4 (m, 2H); 4.8 (d, 1H); 5.1 (d, 1H); 5.2 (d, 1H); 5.6 (d, 1H); 6.9 (s, 1H); 7.3 (s, 10H).

12. Condensation performed using 2-trimethyl-silylamino-3-trimethylsilyloxyiminobutane in THF at −70° followed by addition of 1.5 equivalents of TFA.

13. Product had: IR$vcm^{-1}$, film, 1780, 1720, 1670.

14. Condensation performed in THF at −40° for 30 minutes.

15. Product had the following n.m.r. in $d_6$DMSO + $CD_3COOD$: - 2.0 (s, 3H); 3.6 (s, 2H); 4.6 (d, 1H); 4.9 (d, 1H); 5.3 (d, 1H); 5.7 (d, 1H); 6.8 (s, 1H); 7.0 (s, 1H); 7.1–7.7 (m, 15H).

16. A second purification by chromatography on silica gel was performed using $CH_2Cl_2$/MeOH/HOAc 70:30:1 v/v/v as eluant.

The second last part of Example 9 was then repeated using the compounds listed in Table II as starting materials and the following compounds were thus obtained:

TABLE III

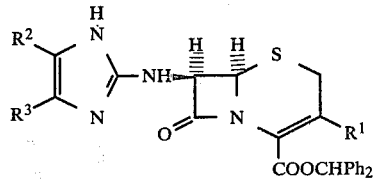

| R¹ | R² | R³ | Footnotes |
|---|---|---|---|
| $CH_2OCOCH_3$ | $CH_2OH$ | H | 1, 2, 3, 4 |
| $CH_2OCOCH_3$ | $CH_3$ | H | 1, 5, 6, 7 |
| $CH_2OCOCH_3$ | $(CH_2)_4$ | | 1, 8, 9, 10 |
| 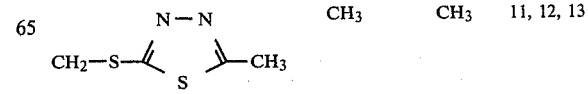 | $CH_3$ | $CH_3$ | 11, 12, 13 |

TABLE III-continued

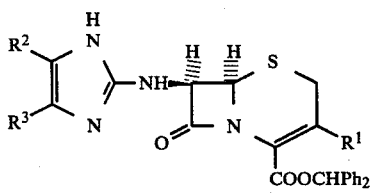

| R¹ | R² | R³ | Footnotes |
|---|---|---|---|
| CH₂OCOCH₃ | Ph | H | 1, 8, 12, 14 |

Footnotes

1. Reaction conducted in MeOH using 2-2.5 equivalents of TiCL₃.
2. Reaction conducted at ambient temperature.
3. Product purified by silica gel chromatography at −20° using CH₂Cl₂/MeOH/HOAc 98:1:1 v/v/v and then CH₂Cl₂/MeOH/HOAc 92:4:4 v/v/v as eluants.
4. Product had the following n.m.r. in d₆DMSO: - 1.95 (s, 3H); 3.6 (m, 2H); 4.65 and 4.86 (2d, 2H); 5.2 (d, 1H); 5.75 (m, 1H); 6.5 (s, 1H); 6.9 (s, 1H); 7.3 (m, 10H).
5. Reaction conducted at 40–45° for 30 minutes.
6. Product purified by silica gel chromatography at low temperature using CH₂Cl₂MeOH/HOAc 96.55:1.15:2.3 v/v/v as eluant.
7. Product had the following n.m.r. in d₆DMSO: - 2.1 (s, 3H); 2.2 (s, 3H); 3.7 (s, 2H); 4.75–5.0 (2d, 2H); 5.3 (d, 1H); 5.7 (d, 1H); 7.0 (s, 1H); 7.4 (m, 10H).
8. Reaction conducted at 40–45° for 10 minutes. A 10% w/v aqueous NaHCO₃ solution was then added to the mixture to pH 7, and the yellow precipitate was collected, washed with water and dried.
9. Product purified by silica gel chromatography at low temperature, using CH₂Cl₂/MeOH/HOAc 98:1:1 v/v/v as eluant.
10. Product had the following n.m.r. in d₆DMSO + CD₃COOD: - 1.7 (m, 4H); 1.9 (s, 3H); 2.4 (m, 4H); 3.5 (m, 2H); 4.6 (s, 2H); 5.2 (d, 1H); 5.4 (d, 1H); 6.9 (s, 1H); 7.3 (s, 10H).
11. Reaction conducted in MeOH/THF 1:1 v/v for 6 hours at 45°.
12. Product purified by chromatography over silica gel at −20° using CH₂Cl₂/MeOH/HOAc 96:2:2 v/v/v as eluant.
13. Product had: IR(KBr) νcm⁻¹: 1780, 1725, 1660.
14. Product had the following n.m.r. in d₆DMSO: - 1.9 (s, 3H); 3.6 (s, 2H); 4.6 (d, 1H); 4.9 (d, 1H); 5.3 (d, 1H); 5.7 (d, 1H); 6.9 (s, 1H); 7.0 (s, 1H); 7.1–7.6 (m 15H).

EXAMPLE 23

The process used in Example 1 or 7 was repeated using the appropriate diphenylmethyl or t-butyl ester as starting material and the following compounds were thus obtained:

TABLE I

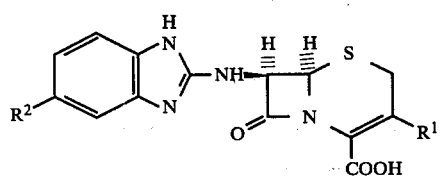

| R¹ | R² | Footnotes |
|---|---|---|
| | OH | 1, 2, 3, 4 |
| CH₂OCOCH₃ | CO₂H | 5, 6, 7, 8 |
| CH₂OCOCH₃ | F | 9, 2, 7, 10 |
| CH₂OCOCH₃ | CF₃ | 11, 2, 12, 13 |

TABLE I-continued

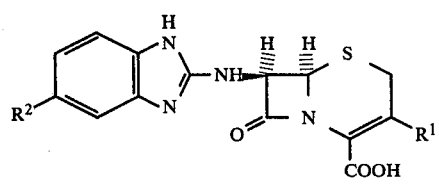

| R¹ | R² | Footnotes |
|---|---|---|
| CH₂OCOCH₃ | CH₂OH | 11, 2, 7, 14 |

Footnotes

1. Reaction carried out in TFA/anisole 3:2 v/v.
2. Reaction conducted at ambient temperature for 10 to 35 minutes.
3. Reaction mixture was evaporated and the residue was dissolved in the minimum amount of MeOH—CH₂Cl₂ and precipitated with petroleum ether.
4. Product, the trifluoroacetate salt, had the following n.m.r. in d₆DMSO: - 3.7 (m, 2H); 3.9 (s, 3H); 4.3 (s, 2H); 5.2 (d, 1H); 5.75 (d, 1H); 6.5–7.3 (m, 3H); 7.85 (d, 1H).
5. Reaction carried out in TFA/toluene 4:3 v/v.
6. Reaction conducted at ambient temperature for 1 hour.
7. As in footnote 3, but using ether instead of petroleum ether.
8. Product, the trifluoroacetate salt, had the following n.m.r. in d₆DMSO + CD₃CO₂D: - 2.05 (s, 3H); 3.3–3.8 (q, 2H); 4.6–5.05 (q, 2H); 5.24 (d, 1H); 5.84 (d, 1H); 7.3 (d, 1H); 7.8 (m, 2H).
9. Reaction carried out in TFA/anisole 2:1 v/v.
10. Product, the trifluoroacetate salt, had the following n.m.r. in d₆DMSO: - 2.04 (s, 3H); 3.6 (m, 2H); 4.72–5.1 (q, 2H); 5.28–5.82 (q, 2H); 6.7–7.5 (m, 3H); 9.05 (m, 1H).
11. Reaction carried out in TFA/anisole 5:1 v/v.
12. Product purified by precipitation from a CH₂Cl₂ with hexane.
13. Product, the trifluoroacetate salt, had the following n.m.r. in d₆DMSO: - 2.1 (s, 3H); 3.7 (q, 2H); 4.80–5.12 (q, 2H); 5.34–5.90 (q, 2H); 7.4–7.8 (m, 3H).
14. Product, the hydrobromide salt, had the following n.m.r. in d₆DMSO: - 2.04 (s, 3H); 3.38 (q, 2H); 4.52 (s, 2H); 4.71–5.03 (q, 2H); 5.25–5.80 (q, 2H); 6.9–7.25 (m, 3H).

The starting material used in the above process may be prepared by repeating the last part of Examples 1, 5 or 10 (reaction of the appropriate substituted ortho-phenylenediamine with the appropriate diphenylmethyl or t-butyl 7-dibromomethyleneamino-3-substituted ceph-3-em-4-carboxylate). The following compounds were thus obtained:

TABLE II

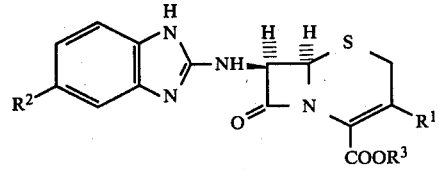

| R¹ | R² | R³ | Footnotes |
|---|---|---|---|
| | OH | CHPh₂ | 1, 2, 3, 4, 5 |
| CH₂OCOCH₃ | CO₂C₄H₉ᵗ | t-C₄H₉ | 1, 6, 3, 7, 8 |
| CH₂OCOCH₃ | F | CHPh₂ | 1, 6, 3, 7, 9 |
| CH₂OCOCH₃ | CF₃ | CHPh₂ | 1, 6, 3, 10, 11 |

TABLE II-continued

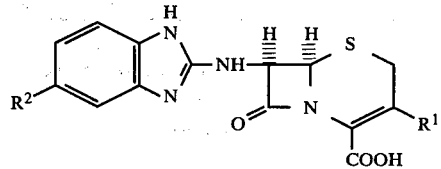

| R[1] | R[2] | R[3] | Footnotes |
|---|---|---|---|
| CH₂OCOCH₃ | CH₂OH | CHPh₂ | 1, 2, 3, 12, 13 |

Footnotes
1. Reaction carried out in anhydrous THF.
2. Reaction conducted for 1 hour at room temperature.
3. Product purified by low temperature chromatography on silica gel.
4. Chromatography eluant CH₂Cl₂/MeOH 98:2 v/v.
5. Product had the following n.m.r. in d₆DMSO: - 3.7 (q, 2H); 3.96 (s, 3H); 4.22 (m, 2H); 5.24 (d, 1H); 5.9 (d, 1H); 6.4–6.7 (m, 3H); 6.95 (s, 1H); 7.2–7.6 (m, 10H); 8.7 (m, 1H).
6. Reaction conducted for 20 hours at room temperature.
7. Chromatography eluant CH₂Cl₂MeOH/HOAc 98:1:1 v/v/v.
8. Product had the following n.m.r. in CD₃OD: - 1.5 (2s, 18H); 2.1 (s, 3H); 3.35–3.84 (q, 2H); 4.65–5.15 (q, 2H); 5.12 (d, 1H); 5.70 (d, 1H); 7.35 (d, 1H); 7.85 (m, 2H).
9. Product had the following n.m.r. in d₆DMSO: - 1.95 (s, 3H); 3.58–3.78 (q, 2H); 4.68–4.86 (q, 2H); 5.34–5.92 (2, 2H); 6.96 (s, 1H); 7.0–7.6 (m, 13H); 8.48 (m, 1H).
10. Chromatography elution with CH₂Cl₂/EtOAc from 8:2 to 7:3 v/v.
11. Product had the following n.m.r. in d₆DMSO: - 1.95 (s, 3H); 3.48–3.73 (q, 2H); H); 4.92 (q, 2H); 5.3–6.0 (q, 2H); 6.9 (s, 1H), 7.3 (m, 13H).
12. Chromatography eluant: CH₂Cl₂/MeOH/HOAc from 96:2:2 to 91:6:3 v/v/v.
13. Product had the following n.m.r. in d₆DMSO: - 1.97 (s, 3H); 3.50–3.74 (q, 2H); 4.5 (s, 2H); 4.65–4.9 (q, 2H); 5.1–5.93 (q, 2H); 6.92 (s, 1H); 7.38 (m, 14H).

The t-butyl 3,4-diaminobenzene-1-carboxylate used above was prepared as follows:

To a suspension of 3,4-diaminobenzoic acid (3.4 g.) in dioxane (100 ml.) and concentrated H₂SO₄ (10 ml.) at 0° was added isobutylene (50 ml.). The mixture was shaken for 20 hours in a pressure bottle at room temperature, then poured into 200 ml. of water. The pH of the resulting mixture was adjusted to 10, and extracted three times with CHCl₃. The combined extracts were dried and concentrated to give 2.5 g. of the t-butyl 3,4-diaminobenzene-1-carboxylate which was used without further purification.

EXAMPLE 24

To a stirred suspension of pivaloyloxymethyl 7-amino-3-methylceph-3-em-4-carboxylate toluene-p-sulphonate in ethyl acetate was added sodium bicarbonate (0.336 g.) in water. The organic layer was separated, dried over MgSO₄ and 1 equivalent of HCl in ether added. The mixture was evaporated to dryness and to the residue was added dry DMF (3 ml.) and 2-chlorobenzimidazole (1.218 g.). The mixture was stirred at 70° for 24 hours and then evaporated to dryness. The residue was dissolved in CH₂Cl₂, washed with water, the organic layer dried and concentrated and the product purified by chromatography on silica gel using CH₂Cl₂/MeOH/HOAc 98.5:1:0.5 v/v/v as eluant. The resulting oil was further purified by precipitation from CH₂Cl₂ solution with di-isopropyl ether to give pivaloyloxymethyl 7-(benzimidazol-2-yl)amino-3-methylceph-3-em-4-carboxylate hydrochloride (14%) having the following n.m.r. in d₆DMSO: 1.1 (s, 9H); 2.05 (s, 3H); 3.65 (q, 2H); 4.25–4.8 (q, 2H); 4.75 (q, 2H); 6.9–7.4 (m, 2H).

The above process was repeated using an equivalent amount of 2-chloro-5-nitrobenzimidazole in place of 2-chlorobenzimidazole and a reaction temperature of 50°. The product was purified by low temperature chromatography on silica gel using CH₂Cl₂/EtOAc 70:30 v/v as eluant, solution in CH₂Cl₂ and filtration and finally further low temperature chromatography using CH₂Cl₂/ether/MeOH 69:30:1 v/v/v as eluant to give pivaloyloxymethyl 7-(5-nitrobenzimidazol-2-yl)-3-methylceph-3-em-4-carboxylate (25%) having the following n.m.r. in d₆DMSO: 1.15 (s, 9H); 2.05 (s, 3H); 3.5 (q, 2H); 5.25–5.8 (q, 2H); 5.8 (m, 2H); 7.35–8.0 (m, 3H); 8.5 (m, 1H).

EXAMPLE 25

The process used in Example 1 or 7 was repeated using the appropriate t-butyl ester as starting material and the following compounds were thus obtained:

TABLE I

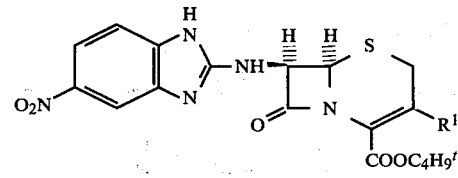

| R[2] | R[1] | Footnotes |
|---|---|---|
| NH₂ | CH₃ | 1, 2, 3, 4 |
| NH₂ | CH₂OCOCH₃ | 1, 2, 3, 5 |
| NHCOCH₃ | CH₂OCOCH₃ | 1, 2, 6, 7 |

Footnotes
1. Reaction conducted in TFA/anisole.
2. Reaction conducted at ambient temperature for 1.15 to 2.5 hours.
3. Reaction mixture was evaporated to dryness, dissolved in the minimum amount of MeOH/CH₂Cl₂ and precipitated with ether.
4. Product, the ditrifluoroacetate salt, had the following n.m.r. in d₆DMSO: - 2.06 (s, 3H); 5.15–5.60 (q, 2H); 6.6–7.2 (m, 2H); (2 proton resonances hidden by solvent).
5. Product, the ditrifluoroacetate salt; had the following n.m.r. in d₆DMSO: - 2.02 (s, 3H); 3.6 (q, 2H); 4.75–5.05 (q, 2H); 5.25–5.78 (q, 2H); 6.5–7.3 (m, 3H).
6. Two products were formed, only one was isolated after following the purification procedure described in Footnote 3.
7. Product, the trifluoroacetate salt, had the following n.m.r. in d₆DMSO: - 2.1 (s, 6H); 3.4 (m, 2H); 4.76–5.08 (q, 2H); 5.27–5.90 (q, 2H); 7.16 (s, 2H); 7.74 (s, 1H); 9.84 (s, 1H).

The starting materials used in the above process may be prepared as follows:

By a process similar to that described in Example 24, using the appropriate t-butyl 3-substituted-7-aminoceph-3-em-4-carboxylate toluene-p-sulphonate and 2-chloro-5-nitrobenzimidazole, the compounds listed in the following Table were prepared:

TABLE II

| R[1] | Footnotes |
|---|---|
| CH₃ | 1 |
| CH₂OCOCH₃ | 2 |

Footnotes
1. The product was purified by low temperature chromatography, eluting with CH₂Cl₂/EtOAc/MeOH 30:70:0.2 v/v/v the remaining 2-chloro-5-nitrobenzimidazole being eliminated by addition of CH₂Cl₂ and filtration. The compound had the following n.m.r. in CDCl₃ + CD₃OD: - 1.55 (s, 9H); 2.12 (s, 3H); 3.4 (q, 2H); 5.22 (d, 1H); 5.83 (d, 1H); 7.2–8.5 (m, 3H).
2. The product was purified by low temperature chromatography, eluant CH₂Cl₂/EtOAc 70:30 v/v followed by elimination of the excess 2-chloro-5-nitrobenzimidazole by addition of CH₂Cl₂ filtration and concentration of the organic phase. The compound had the following IR (KBr) νcm⁻¹: - 1770, 1720, 1585.

The nitro radical was then transformed into an amino or acetylamino radical to give the compounds listed in the following Table:

TABLE III

R²—[benzimidazol-NH—cephem core]—R¹, with COOC₄H₉ᵗ

| R² | R¹ | Footnotes |
|---|---|---|
| NH₂ | CH₃ | 1 |
| NH₂ | CH₂OCOCH₃ | 2 |
| NHCOCH₃ | CH₂OCOCH₃ | 3 |

Footnotes
1. Product obtained as follows. To a solution of t-butyl 3-methyl-7-(5-nitrobenzimidazol-2-yl)amino-ceph-3-em-4-carboxylate (0.21 g.) in THF (3 ml.) and MeOH (3 ml.) at 0° was added 6 equivalents of a 15% w/v aqueous solution of TiCl₃. To the mixture was added NaHCO₃ (0.756 g.) and the pH was adjusted to 7 with 10% w/v aqueous sodium bicarbonate. The precipitate was collected and purified by low temperature chromatography on silica gel using CH₂Cl₂/MeOH/AcOH 97:1.5:1.5 v/v/v as eluant. The compound had following n.m.r. in d₆DMSO: - 1.5 (s, 9H); 2.0(s, 3H); 5.15–5.75 (q, 2H); 6.2–6.9 (m, 3H); (2H resonances hidden by solvent.)
2. Product obtained by a process similar to that described in Footnote 1 but using t-butyl 3-acetoxymethyl-7-(5-nitrobenzimidazol-2-yl)aminoceph-3-em-4-carboxylate. The product was purified by low temperature chromatography on silica gel using CH₂Cl₂/MeOH/HOAc 97:2:1 to 78:14:8 v/v/v as eluant. Product had the following n.m.r. in d₆DMSO: - 1.5 (s, 9H); 2.05 (s, 3H); 3.55(q, 2H); 4.6 (q, 2H); 5.2 (d, 1H); 5.8 (d, 1H); 6.1–6.9 (m, 3H):.
3. Product obtained as follows. To a solution of t-butyl 3-acetoxymethyl-7-(5-aminobenzimidazol-2-yl)-aminoceph-3-em-4-carboxylic acid (0.521 g.) in CH₂Cl₂ (100 ml.) and CH₃COOH (2 ml.) was added 1 equivalent of acetic anhydride. The mixture was stirred briefly at 0° then concentrated and the residue chromatographed on silica gel at −20° using CH₂Cl₂/MeOH/HOAc 96:2:2 v/v/v as eluant. The product had the following n.m.r. in d₆DMSO: - 1.55 (s, 9H); 2.05 (s, 3H); 2.1 (s, 3H); 3.5 (m, 2H); 4.9 (m, 2H); 5.2–5.6 (q, 2H); 7.0 (s, 2H): 7.65 (m, 1H); 9.6 (m, 1H).

EXAMPLE 26

The process used in Example 1 or 7 was repeated using the appropriate diphenylmethyl or t-butyl ester as starting material and the following compounds were thus obtained:

TABLE I

RCH₂—[benzimidazol-NH—cephem core]—CH₂OCOCH₃, with COOH

| R | Footnotes |
|---|---|
| NH₂ | 1, 2, 3, 4 |
| N₃ | 5, 6, 7 |
| NHCOCH₃ | 5, 6, 8 |

| R¹ | Footnotes |
|---|---|
| NHCO—CH(NH₂)—Ph | 1, 2, 3, 9 |
| NH—COCH₂NH₂ | 10, 2, 6, 11 |

Footnotes
1. Reaction carried out in TFA/anisole.
2. Reaction conducted at ambient temperature for 20–40 minutes.
3. Product purified by evaporation of reaction mixture and precipitation of product from a solution in the minimum amount of MeOH with ether.
4. Product, the hydrated ditrifluoroacetate salt, had the following n.m.r. in d₆DMSO: - 2.01 (s, 3H); 3.55 (m, 3H); 4.04 (m, 2H); 4.68 and 5.01 (q, 2H); 5.22 and 5.85 (q, 2H); 7.4–7.7 (m, 3H).
5. The solution of the diphenylmethyl ester in anisole was cooled to 0° and TFA was added, the mixture was allowed to return at ambient temperature and left at this temperature for 0.5 hour.
6. Product purified by evaporation of reaction mixture and precipitation of residue from a solution in the minimum CH₂Cl₂/MeOH with ether.
7. Product, the trifluoroacetate salt, had the following n.m.r. in d₆DMSO: - 2.1 (s, 3H); 3.66 (m, 2H); 4.55 (s, 2H); 4.8 and 5.11 (q, 2H); 5.33 and 5.87 (q, 2H); 7.0–7.5 (m, 3H).
8. Product, the trifluoroacetate salt, had the following n.m.r. in d₆DMSO + CD₃CO₂D: - 1.88 (s, 3H); 2.0 (s, 3H); 3.48 and 3.6 (q, 2H); 4.3 (s, 2H); 4.7 and 5.05 (q, 2H); 5.23 (d, 1H); 5.76 (d, 1H); 6.90–7.4 (m, 3H).
9. Compound had the following spectra: IR (KBr) ν cm⁻¹ 1775, 1670 cm⁻¹ and n.m.r. in d₆DMSO: - 2.02 (s, 3H); 3.54 (m, 2H); 4.17–4.4 (m, 2H); 4.7 and 5.05 (q, 2H); 4.90 (s, 1H); 5.18 (d, 1H); 5.82 (d, 1H); 6.7–7.6 (m, 8H); 8.65 (m, 1H).
10. Reaction conducted in TFA.
11. Product, the ditrifluoroacetate salt, had the following n.m.r. in d₆DMSO + CD₃CO₂D: - 2.05 (s, 3H); 3.0–4.0 (m, 4H); 3.6 (m, 4H); 4.37 (m, 2H); 4.7 and 5.0 (q, 2H); 5.2 (d, 1H); 5.78 (d, 1H); 6.8–7.3 (m, 3H).

The starting materials used in the above process may be obtained as follows. First the substituted ortho-phenylenediamines listed in the following Table II were prepared.

TABLE II

RCH₂—[phenyl with NH₂, NH₂]

| R | Footnotes |
|---|---|
| NH—C(=O)—OC₄H₉ᵗ | 1 |
| N₃ | 2, 3 |
| NH—C(=O)—CH(NH—C(=O)—OC₄H₉ᵗ)—C₆H₅ | 2, 4, 5, 6 |
| —NH—C(=O)—CH₂N(H)—C(=O)—OC₄H₉ᵗ | 2, 4, 7, 8 |

Footnotes
1. To a stirred solution of 1-amino-2-nitro-4-cyanobenzene (0.5 g.) in THF (20 ml.) cooled at 10° was added 6 equivalents of a solution of B₂H₆ in THF. The mixture was allowed to return at ambient temperature, stirring was continued two hours and the mixture was

TABLE II-continued

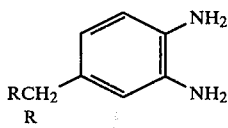

| R | Footnotes |
|---|---| then treated with MeOH and a solution of HCl in MeOH.
The mixture was concentrated, treated with aqueous 10%
w/v NaOH and extracted (×3) with ether. After drying and
concentration 0.35 g. of 1-amino-2-nitro-4-aminomethyl-
benzene were obtained.
To a stirred solution of this compound in dry
dioxane (10 ml.) was added 0.258 g. of 2-(t-butoxy-
carbonyloxyamino)-2-phenylacetonitrile. After 20 hours
at ambient temperature, the mixture was concentrated and
the residue purified by silica gel chromatography,
eluant $CH_2Cl_2$/ether 90:10 v/v, to give 1-amino-2-nitro-
4-t-butoxycarbonylaminomethylbenzene.
0.2 g. Of this compound was hydrogenated in
THF/ethanol at atmospheric pressure over 10% w/w Pd/C. to
give 0.18 g. of 1,2-diamino-4-t-butoxycarbonylaminomethyl-
benzene.
2. To a solution of 3,4-dinitrobenzylalcohol
(20 g.) and triethylamine (15.4 ml.) in $CH_2Cl_2$ at 0° was
added methanesulphonyl chloride (8.5 ml.). After 1
hour at 0° the reaction mixture was washed with cold water,
then with cold aqueous 2N HCl and neutralised with aqueous
5% w/v $NaHCO_3$. The solution was dried over $MgSO_4$ and
concentrated to give 25.5 g. of an oily product IR (film)
$v$ cm$^{-1}$: 1550, 1370, 1360, 1180.
3. The compound obtained in Footnote 2 (3 g.) was
mixed with dioxane (15 ml.), water (5 ml.) and sodium
azide (0.85 g.) and the mixture was heated to 35-40°
for 1.5 hour. To the reaction mixture cooled at 0° was
added 12 equivalents of $TiCl_3$ in solution in water. The
mixture was allowed to return to ambient temperature,
was concentrated in vacuum, then neutralised at 0° with
concentrated $NH_4OH$. $TiO_2$ was filtered off, the filtrate
extracted with EtOAc, dried over $MgSO_4$ and concentrated
to give a crude sample of 1,2-diamino-4-azidomethyl-
benzene, IR (film) $v$ cm$^{-1}$: 3300-3450, 2100.
4. In a pressure bottle flask was suspended the
compound obtained in Footnote 2 (10 g.) in 400 ml. of
MeOH saturated with $NH_3$ (400 ml.) and the mixture
shaken at 0° for 20 hours. After filtration and partial
concentration the filtrate was treated at 0° with a
solution of HCl in ether (12% w/v). After filtration and
washing with ether 5.2 g. of 1,2 dinitro-4-aminomethyl-
benzene hydrochloride (5.2 g.) was obtained. 8. free
base was obtained by basification of an aqueous solution
of the hydrochloride to pH10, extraction with EtOAc,
drying of the organic phase over $K_2CO_3$ and concentration.
5. The free base obtained in Footnote 4 (1.2 g.)
was added to a stirred mixture of 1.5 g. of N—(t-butyl-
oxycarbonyl)-DL-phenylglycine (1.5 g.), dry $CH_2Cl_2$(10 ml.)
dry THF (15 ml.) and 1-ethoxycarbonyl-2-ethoxy-1,2-
dihydroquinoline (1.5 g.). After 1.5 hour the mixture
was concentrated, the residue dissolved in $CH_2Cl_2$ and
the solution washed with aqueous 2N HCl, aqueous 5%
w/v $NaHCO_3$, dried over $MgSO_4$ and concentrated. The
residue was purified by chromatography on silica gel
using EtOAc/cyclohexane 1:1 v/v as eluant to give the
product (2.1 g.).
6. A solution of the compound obtained in Footnote
5 (1.8 g.) in ethanol (30 ml.) was hydrogenated for 1.5
hour at atmospheric pressure with 0.1 g. of $PtO_2$ catalyst.
The mixture was filtered and the filtrate evaporated to
give the orthophenylenediamine derivative (1.4 g.) which
was used without further purification.
7. Process described in Footnote 5 using N—(t-
butyloxycarbonyl) glycine instead of N—(t-butyloxycarbonyl)-
DL-phenylglycine.
8. The product obtained in FOOTNOTE 7 (2. g.) in
THF (15 ml.) and ethanol (30 ml.) was submitted to
catalytic hydrogenation (10% Pd/C) at atmospheric
pressure for 3 hours. After filtration and concentration,
1.5 g. of a visquous oil was obtained. This compound
was used without further purification. The last part
of Example 1, 5 or 10 was then repeated using the
appropriate substituted orthophenylenediamine and the
appropriate diphenylmethyl or t-butyl 7-dibromomethylene-
amino-3-acetoxymethylceph-3-em-4-carboxylate. One of

TABLE II-continued

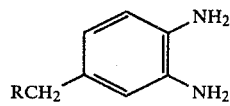

| R | Footnotes |
|---|---| the products from this reaction was also subjected to
further chemical transformations. The following compounds
were thus obtained:-

TABLE III

| $R^1$ | $R^2$ | Footnotes |
|---|---|---|
| $\begin{array}{c} H \\ | \\ -N-C-OC_4H_9{}^t \\ \| \\ O \end{array}$ | $CHPh_2$ | 1, 2, 3, 4 |
| $N_3$ | $CHPh_2$ | 5, 2, 6, 7 |
| $NHCOCH_3$ | $CHPh_2$ | 8, 9 |
| $\begin{array}{c} NH-C-CH-C_6H_5 \\ \|\| \quad \| \\ O \quad NH \\ \| \\ O=C-OC_4H_9{}^t \end{array}$ | $CHPh_2$ | 1, 2, 3, 10 |
| $\begin{array}{c} -NH-C-CH_2NHC-OC_4H_9{}^t \\ \|\| \quad \quad \|\| \\ O \quad \quad O \end{array}$ | $t-C_4H_9$ | 1, 11, 12, 13, 14 |

Footnotes
1. Reaction carried out in dry THF.
2. Reaction conducted 20 hours at ambient temperature.
3. Product purified at low temperature by low
pressure chromatography, eluting with $CH_2Cl_2$/MeOH/HOAc
98:1.3:0.7 v/v/v.
4. Product had the following n.m.r. in d$_6$DMSO: -
1.4 (s, 9H); 1.98 (s, 3H); 3.64 (m, 2H); 4.13 (m, 2H);
4.66 and 4.92 (q, 2H); 5.3 (d, 1H); 5.95 (d, 1H); 6.93
(s, 1H); 7.12 (s, 1H); 7.2-7.6 (m 13H).
5. Reaction carried out in MeOH/THF 1:10 v/v.
6. As in Footnote 3 with solvents ratio of 995:4:1 v/v/v.
7. Product had the following n.m.r. in d$_6$DMSO: -
2.0 (s, 3H); 3.7 (M, 2H); 4.51 (s, 2H); 4.71-4.97
(q, 2H); 5.37-6.0 (q, 2H) 6.98 (s, 1H); 7.1-7.6 (m, 13H).
8. To a solution of the compound from Footnote 7
(0.47 g.) in ethanol (20 ml.) dioxane (10 ml.) was
added platinium oxide (0.2 g.) and the mixture was hydrogenated
at ambient temperature and atmospheric
pressure for 3 hours. The catalyst was removed and the
mixture was concentrated to give 0.42 g. of an intermediate
compound having $R^1 = NH_2$, $R^2 = CHPh_2$.
This intermediate was dissolved in dry $CH_2Cl_2$ and
1 equivalent of acetic anhydride was added. The mixture was
allowed to react at room temperature under nitrogen atmosphere.
The reaction mixture was treated as in Footnote 6.
The final product was further purified by precipitation from
$CH_2Cl_2$/MeOH with ether.
9. Product was a mixture of $\Delta^3$ and $\Delta^2$ isomers;
n.m.r. of $\Delta^3$ isomer in d$_6$DMSO: - 1.87 (s, 3H); 2.0
(s, 3H); 3.67 (m, 2H); 4.3 (q, 2H); 4.7 and 4.93 (q, 2H); 5.35 and
5.90 (q, 2H); 6.95 (s, 1H); 7.4 (s, 13H); 8.35 (m, 1H).
10. Product had the following n.m.r. in d$_6$DMSO: - 1.36 (s, 9H);
1.90-1.98 (2s, 3H); 3.62 (m, 2H); 4.3 (d, 2H); 4.68 and
4.93 (q, 2H); 5.15 (d, 1H); 5.30 and 5.88 (q, 2H); 6.91 (m, 1H);
7.1-7.5 (m, 18H); 8.45 (m, 1H).
11. Reaction conducted 7 hours at ambient temperature.
12. As in Footnote 3 in a solvent ratio of 990:5:5 v/v/v.
13. Compound was further purified by precipitation from minimum
$CH_2Cl_2$/MeOH solution with ether.
14. Product had the following n.m.r. in d$_6$DMSO: - 1.35 (s, 3H);

TABLE III-continued

[structure with R¹CH₂-benzimidazole-NH-β-lactam-CH₂OCOCH₃, COOR²]

| R¹ | R² | Footnotes |
|---|---|---|

1.5 (s, 3H); 2.0 (s, 3H); 3.6 (m, 4H); 4.3 (dd, 2H); 4.63 and 4.94 (q, 2H); 5.2 and 5.85 (q, 2H); 6.7–7.1 (m, 4H); 8.05 (m, 1H).

EXAMPLE 27

The process used in Example 1 or 7 was repeated using the appropriate t-butyl ester as starting material and the following compounds were thus obtained:

TABLE I

[structure with RCH₂-benzimidazole-NH-β-lactam-CH₂OCOCH₃, COOH]

| R | Footnotes |
|---|---|
| CN | 1, 2, 3 |
| CONH₂ | 4, 2, 5 |

Footnotes
1. Reaction carried out for 2.25 hours in a mixture of TFA/anisole 1:1 v/v at room temperature.
2. The reaction mixture was evaporated, and the residue precipitated from CH₂Cl₂/MeOH solution with ether.
3. Product, the trifluoroacetate salt, had the following n.m.r. in d₆DMSO: - 2.03 (s, 3H); 3.42 and 3.67 (q, 2H); 4.01 (s, 2H); 4.71 and 5.01 (q, 2H); 5.22 (d, 1H); 5.80 (d, 1H) 6.90–7.45 (m, 3H).
4. Reaction carried out for 1.5 hours at ambient temperature in TFA.
5. Product, the trifluoroacetate salt, had the following n.m.r. in d₆DMSO: - 2.07 (s, 3H); 3.39 (s, 2H); 3.0–4.0 (m, 2H); 4.7 (d, 1H); 5.15 (d, 1H); 5.24 (d, 1H); 5.86 (m, 1H); 6.65–7.45 (m, 7H).

The starting materials for use in the above process may be prepared as follows:

A solution of 1-amino-2-nitro-4-cyanomethylbenzene (6 g.) in ethanol (100 ml.) was hydrogenated for 1.5 hour at atmospheric pressure in presence of 3.6 g. of 10% w/w Pd/C. The catalyst was removed and the solvent was evaporated to give 1,2-diamino-4-cyanomethylbenzene which was used without further purification.

To 1.03 g. of 1,2-diamino-4-cyanomethylbenzene (1.03 g.) was slowly added concentrated sulphuric acid (7 ml.). The mixture was heated at 90° for 90 minutes, then poured onto 50 ml. of water and ice and adjusted to pH 8 with NaOH. The precipitate which formed on cooling was discarded and the aqueous phase was concentrated to drynes. The residue was extracted with acetone, the extracts were concentrated and chromatographed on silica gel using CH₂Cl₂/MeOH 9:1 to 8:2 v/v to give 1,2-diamino-4-carbamoylmethylbenzene (0.65 g.) which was used without further purification.

The last part of Example 1 was repeated using the appropriate orthophenylenediamines and t-butyl 7-dibromomethyleneamino-3-acetoxymethylceph-3-em-4-carboxylate as starting materials. The following compounds were thus obtained:

TABLE II

[structure with RCH₂-benzimidazole-NH-β-lactam-CH₂OCOCH₃, COOC₄H₉ᵗ]

| R | Footnotes |
|---|---|
| CN | 1, 2, 3, 4 |
| CONH₂ | 1, 5, 6, 7, 8 |

Footnotes
1. Reaction conducted in dry THF.
2. Reaction conducted for 5 hours at ambient temperature.
3. Product was purified by low temperature chromatography on silica gel using CH₂Cl₂/MeOH/HOAc 95:4:1 then 97:2.5:0.5 v/v/v as eluant.
4. Product had m.p. 116° (decomp.) and the following n.m.r. in CD₃OD: - 1.53 (s, 9H); 2.05 (s, 3H); 3.38 and 3.67 (q, 2H); 3.88 (s, 2H); 4.72 and 5.06 (q, 2H); 5.16 (d, 1H); 5.71 (d, 1H); 6.8–7.4 (m, 3H).
5. Reaction conducted for 20 hours at ambient temperature.
6. As in Footnote 3 with a solvent ratio of 93:5:7 v/v/v.
7. Compound further purified by precipitation from MeOH solution with ether.
8. Product had the following IR (KBr) νcm⁻¹: 1780, 1720, 1660 and 1575.

EXAMPLE 28

The process described in Example 1 was repeated using diphenylmethyl 7-(imidazol-2-yl)amino-3-acetoxymethylceph-3-em-4-carboxylate as starting material and the following compound was obtained:

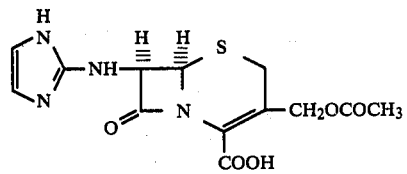

Footnotes
1. The reaction was conducted for 1 hour at ambient temperature in anisole/TFA 3:1 v/v. The product was dissolved in the minimum amount of CH₂Cl₂/MeOH and precipitated with a mixture of ether and hexane. The product had the following n.m.r. in d₆DMSO + CF₃COOD:- 2.0 (s, 3H); 3.7 (m, 2H); 4.8 (d, 1H); 5.2 (d, 1H); 5.3 (d, 1H); 5.7 (d, 1H); 7.2 (s, 2H).

The starting material used in the above process may be obtained as follows:

To a stirred solution of diphenylmethyl 7-(1-hydroxy-2-imidazolin-2-yl)amino-3-acetoxymethylceph-3-em-4-carboxylate (prepared by a process similar to that described in Example 13) (0.174 g.) in CH₂Cl₂ (1.5 ml.) at −40° was added 2-fluoro-1-methylpyridinium toluene-p-sulphonate (98 mg.) followed by freshly distilled triethylamine (147 μl.) in dry CH₂Cl₂(1 ml.). After 1 hour at −40° TFA (90 μl.) was added, the mixture was diluted with CH₂Cl₂, washed twice with water and the organic phase dried over MgSO₄. The solution was concentrated and the residue chromatographed at low temperature over silica gel, elution with CH₂Cl₂/MeOH/HOAc 100:0:0 to 92:4:4 v/v/v as eluant. There was obtained diphenylmethyl 7-(imidazolyl-2-yl)amino-3-acetoxymethylceph-3-em-4-carboxylate (0.105 g.) having the following n.m.r. in d₆DMSO+CD₃COOD: 2.0 (s, 3H); 3.7 (s, 2H); 4.7 (d, 1H); 4.9 (d, 1H); 5.4 (d, 1H); 5.7 (d, 1H); 6.9 (s, 1H); 7.0 (s, 2H); 7.3 (s, 10H).

EXAMPLE 29

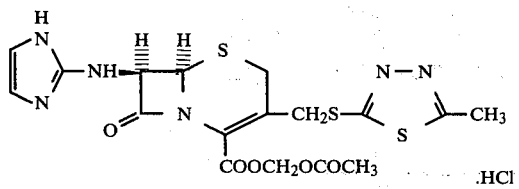

A solution of acetoxymethyl 7-amino-3-(2-methyl-1,3,4-thiadiazol-5-yl)thiomethylceph-3-em-4-carboxylate (0.28 g.) and 2-fluoroimidazole hydrochloride (0.1 g.) in dry DMF (1 ml.) was heated at 60° for 2 hours. The reaction mixture was concentrated in vacuum and the residue chromatographed over silica gel, eluting with $CH_2Cl_2$/MeOH 95:5 v/v. The purified compound was then treated with one equivalent of HCl in MeOH the hydrochloride being precipitated by addition of the resulting solution to dry ether. The product acetoxymethyl 7-(imidazol-2-yl)amino-3-(2-methyl-1,3,4-thiadiazol-5-yl)thiomethylceph-3-em-4-carboxylate hydrochloride, had the following IR spectrum (KBr) $\nu$ cm$^{-1}$: 1780 (broad), 1740 (shoulder), 1655 (sharp) and the following n.m.r. in $d_6$DMSO+CF$_3$COOD: 2.15 (s, 3H); 2.7 (s, 3H); 3.8 (brs 2H); 5.3 and 5.8 (q, 2H); 7.1 (s, 2H); other resonances hidden by solvent or poorly resolved.

The starting ester used in the above process may be made as follows:

To a solution of NaI (3 g.) in acetone (6 ml.) was added chloromethyl acetate (2.17 g.). The mixture was stirred one hour at room temperature and was then added to a solution of sodium 3-(2-methyl-1,3,4-thiadiazol-5-yl)thiomethyl-7-(1H-tetrazol-1-yl)acetylaminoceph-3-em-4-carboxylate (4.7 g.) in DMSO (6 ml.). The mixture was heated at 50° for five hours, the acetone was removed by evaporation and the residue poured in 200 ml. of water. After trituration a powder was obtained which was filtered and washed with ether. The crude product was purified by chromatography on silica gel eluting with $CH_2Cl_2$/MeOH 95:5 v/v. The resulting acetoxymethyl ester had the following n.m.r. in $d_6$DMSO+CD$_3$OD: 2.1 (s, 3H); 2.7 (s, 3H); 3.8 (m, 2H); 4.2 and 4.7 (q, 2H); 5.2 (d, 1H); 5.45 (s, 2H); 5.80 (d, 1H); 5.9 (m, 2H); 9.3 (s, 1H).

To a solution of PCl$_5$ (2.08 g.) in dry $CH_2Cl_2$ (12 ml.) was added quinoline (1.93 g.). The resulting suspension was cooled to $-15°$ and the above acetoxymethyl ester (2.63 g.) was added portionwise. The black mixture was allowed to return to ambient temperature and after one hour of stirring the resulting solution was added under nitrogen to a solution of 1,3-butanediol (3 g.) in $CH_2Cl_2$ (5 ml.) cooled at $-15°$. The mixture was stirred for two hours at ambient temperature and $CH_2Cl_2$ (100 ml.) was then added. The resulting precipitate was filtered to give acetoxymethyl 7-amino-3-(2-methyl-1,3,4-thiadiazole-5-yl)thiomethylceph-3-em-4-carboxylate hydrochloride (1.8 g.) having the following partial n.m.r. in $d_6$DMSO+CD$_3$COOD: 2.1 (s, 3H); 2.7 (s, 3H); 5.2 (brs, 1H); 5.7 (brs, 1H). The free base was obtained by addition of triethylamine to a suspension of the hydrochloride in water/$CH_2Cl_2$ until the pH was 8. The organic phase was then separated and evaporated.

EXAMPLE 30

To a solution of toluene-p-sulphonic acid hydrate (54 mg.) in dry DMF (1 ml.) was added 2-fluoro-1-triphenylmethylimidazole (110 mg.) and the solution heated in a preheated bath at 80°. After 5 minutes, to allow complete formation in situ of 2-fluoroimidazole, 7-amino-3-(1,3,4-thiadiazol-2-yl)thiomethylceph-3-em-4-carboxylic acid (110 mg.) was added and heating continued for 2.5 hours. A further portion of the fluoroimidazole (50 mg.) was then added, heating was continued for a further 30 minutes, and the mixture was cooled and evaporated at room temperature. To the residue was added water (10 ml.) and ethyl acetate (25 ml.) and the mixture filtered and the phases separated. The aqueous layer was concentrated to 4 ml., filtered and subjected to preparative HPLC on Whatman "Partisil 10" using water/MeOH/HOAc 80:20:1 v/v/v as eluant. The product crystallised on addition of acetone. It was washed with acetone and ether to give 7-(imidazol-2-yl)amino-3-(1,3,4-thiadiazol-2-yl)thiomethylceph-3-em-4-carboxylic acid (15 mg.) having the following n.m.r. in $d_6$DMSO+CD$_3$COOD: 3.52 (d, 1H); 3.79 (d, 1H); 4.33 (d, 1H); 4.6 (d, 1H); 5.12 (d, 1H); 5.58 (d, 1H); 6.83 (s, 2H); 9.49 (s, 1H).

The above process was repeated using 4-carboxy-2-fluoro-1triphenylmethylimidazole, 4-ethoxycarbonyl-2-fluoro-1-triphenylmethylimidazole and 3-acetoxymethyl-7-aminoceph-3-em-4-carboxylic acid as starting materials and the following compounds were thus obtained:

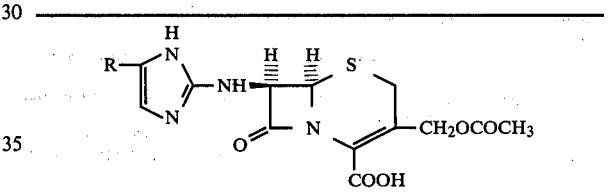

| R | Footnotes |
|---|---|
| COOC$_2$H$_5$ | 1, 2 |
| COOH | 3, 4 |

Footnotes
1. Product purified by HPLC using water/MeOH/HOAc 74:25:1 v/v/v.
2. Product had the following n.m.r. in $d_6$DMSO:- 1.22 (t, 3H); 2.03 (s, 3H); 3.32–3.61 (q, 2H); 4.17 (q, 2H); 4.56–4.93 (q, 2H); 5.14 (d, 1H); 5.67 (q, 1H); 7.01 (d, 1H); 7.28 (s, 1H).
3. Product purified by HPLC using water/MeOH/HOAc 76.5:12.5:1 v/v/v.
4. Product had the following n.m.r. in $d_6$DMSO + CD$_3$CO$_2$D:- 2.03 (s, 3H); 3.43–3.6 (q, 2H); 4.72–5.0 (q, 2H); 5.16 (d, 1H); 5.71 (d, 1H); 7.24 (s, 1H).

The imidazole starting materials may be prepared as follows:

To a solution of 2-fluoroimidazole (4.45 g.) in $CH_2Cl_2$ (100 ml.) and trimethylamine (7.93 ml.) was added triphenylmethyl chloride (14.4 g.) and the mixture was stirred for 2.5 hours. The solution was washed with water and brine, dried (MgSO$_4$), treated with decolourising charcoal, filtered and evaporated. The solid residue was triturated with ether followed by methanol to give 2-fluoro-1-triphenylmethylimidazole (13.6 g.), m.p. 182°–185°.

A solution of 2-fluoro-1-triphenylmethylimidazole (3.28 g.) in dry THF (33 ml.) was treated, under argon, at $-75°$ with two equivalents of t-butyl lithium (10 ml. of a 1.93M solution in pentane). After stirring 3 hours at $-75°$, DMF (1.5 ml.) was added. The reaction mixture was kept a further hour at $-75°$ then allowed to warm up slowly to room temperature. The reaction was worked up by diluting with ether, washing with 2N HCl followed by brine. The ether layer was concentrated under a steam of argon to give 4-formyl-2-fluoro-1-triphenylmethylimidazole, (2.2 g.) m.p. 177°–179°.

A solution of 4-formyl-2-fluoro-1-triphenylmethylimidazole (356 mg.) in ethanol (5 ml.) and CH$_2$Cl$_2$ (3 ml.) was treated with silver nitrate (0.37 g.) in water (0.5 ml.) followed by the dropwise addition of 5 ml. of potassium hydroxide solution (5 ml. of a solution of 2.1 g. KOH in 35 ml. water). The mixture was stirred at room temperature for two hours, filtered and the filtrate extracted with ether. The aqueous layer was acidified with concentrated HCl and extracted with CHCl$_3$. The organic layer was dried over MgSO$_4$, filtered and the solvent evaporated to give 4-carboxy-2-fluoro-1-triphenylmethylimidazole (261 mg.) as a white solid having the following n.m.r. in d$_6$DMSO: 7.0–7.68 (m, 16H); 11.5–12.5 (br, 1H).

A solution of 4-carboxy-2-fluoro-1-triphenylmethylimidazole (280 mg.) in THF (0.75 ml.) was treated, under argon with 1,5-diazabicyclo-5,4,0-undec-5-ene (0.112 ml.) followed by ethyl iodide (0.069 ml.). The mixture was stirred for two hours at room temperature, water was added and the mixture extracted, with ether. The ether extract was dried (MgSO$_4$) and evaporated to give 4-ethoxycarbonyl-2-fluoro-1-triphenylmethylimidazole (185 mg.) as a yellow foam having the following n.m.r. in CDCl$_3$: 1.38 (t, 3H); 4.36 (q, 2H); 7.0–7.5 (m, 16H).

EXAMPLE 31

A suspension of anhydrous toluene-p-sulphonic acid (0.74 g.) and 3-acetoxymethyl-7-aminoceph-3-em-4-carboxylic acid (1.17 g.) in dry DMF (17.5 ml.) was stirred for 15 minutes at room temperature to effect partial solution. One portion of 2-fluoroimidazole (0.74 g.) was then added and the mixture stirred at 90° for 2 hours. The solvent was evaporated at ambient temperature, 2% v/v aqueous HOAc (20 ml.) was added to the residue and the mixture was extracted with EtOAc (20 ml.). The aqueous layer was concentrated to 15 ml., filtered and the filtrate purified by preparative HPLC on Whatman "Partisil 10" using water/MeOH/HOAc 80:20:1 v/v/v as solvent. The product was further purified by trituration with acetone and washing with acetone and ether to give 3-acetoxymethyl-7-(imidazol-2-yl)aminoceph-3-em-4-carboxylic acid (0.42 g.) as a hydrated mixed acetate/toluene-p-sulphonate salt having m.p. >160° (decomp.) and the following n.m.r. in D$_2$O: 2.28 (s, 3H); 3.58 (d, 1H); 3.89 (d, 1H); 4.92 (d, 1H); 5.13 (d, 1H); 5.42 (d, 1H); 5.70 (d, 1H); 7.08 (s, 2H).

The above process was repeated using the appropriate 7-aminocephalosporin derivative and the following compounds were thus obtained:

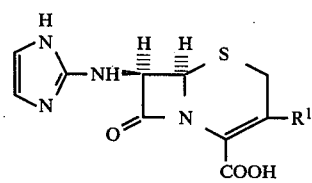

| R$^1$ | Footnotes |
|---|---|
| 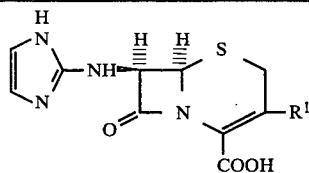 | 1, 2, 3 |
| 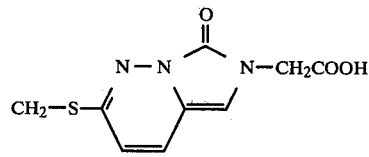 | 4, 5 |
| 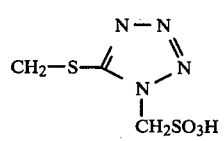 | 1, 6, 7 |

Footnotes

1. Reaction conducted at 85° for 3 hours.

2. Product purified by taking up residue from reaction mixture in distilled water, filtering and extracting with ethyl acetate. The aqueous layer was clarified with charcoal, the pH adjusted to 6 with aqueous NaOH solution and the volume reduced to 2 ml. The product then crystallised.

3. Product had m.p. 203–220° (decomp.).

4. Product was purified by preparative HPLC on Whatman "Partisil 10" using water/MeOH/HOAc 70:30:1 v/v/v as eluant.

5. Product, the dihydrate, had the following n.m.r. in D$_2$O + TFA:- 3.3 (d, 1H); 3.64 (d, 1H); 3.92 (d, 1H); 4.26 (d, 1H); 4.59 (s, 2H); 4.93 (d, 1H); 5.20 (d, 1H); 6.56 (s, 2H); 6.75 (d, 1H); 7.25 (d, 1H).

6. Product purified by preparative HPLC on Whatman "Partisil 10" using water/MeOH/HOAc 90:10:1 v/v/v as eluant. The product crystallised on treatment with acetone.

7. The product, the toluene-p-sulphonate salt, had the following n.m.r. in d$_6$DMSO + CD$_3$CO$_2$D:- 2.32 (s, 3H); 3.64 (d, 1H); 3.9 (d, 1H); 4.19 (d, 1H); 4.46 (d, 1H); 5.05 (s, 2H); 5.17 (d, 1H); 5.57 (d, 1H); 7.06 (s, 2H); 7.14 (d, 2H); 7.54 (d, 2H).

EXAMPLE 32

To a suspension of 3-acetoxymethyl-7-(imidazol-2-yl)aminoceph-3-em-4-carboxylic acid (39.8 mg.) in dry acetonitrile (200 μl.) was added 1-methyl-1H-tetrazole-5-thiol (12 mg.) followed immediately by boron trifluoride etherate in ether (48% w/w, 31 μl.). The clear yellow solution which was formed was stirred at ambient temperature for 0.5 hours then at 50° for 2.5 hours. The solvent was removed under reduced pressure, the residue dissolved in a mixture of water (900 μl.) and eluant (400 μl), the mixture filtered and purified by preparative HPLC on Whatman "Partisil 10" using water/MeOH/HOAc 80:20:1 v/v/v as eluant. There was thus obtained 7-(imidazol-2-yl)amino-3-(1-methyl-1H-tetrazol-5-yl)thiomethylceph-3-em-4-carboxylic acid as a crystalline solid (55%) identical to the product obtained in Example 31.

The above process was repeated using the appropriate thiols as starting materials and the following compounds were thus obtained:

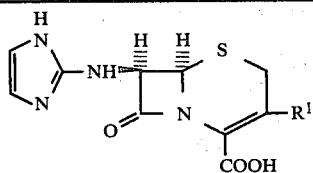

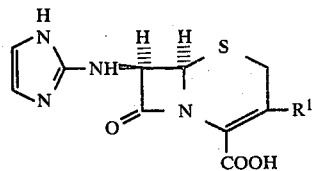

| $R^1$ | Footnotes |
|---|---|
| N—N with NH, CF3 | 1, 2, 3 |
| N—N with CH(CH3)2 | 4, 5, 6 |
| N—N with CH2CF3 | 7, 8, 9, 10 |
| N—N with CH2CH2SCH3 | 11, 12, 13 |

Footnotes
1. Reaction carrried out at 50° for 5 hours.
2. Product purified by preparative HPLC on Whatman "Partisil 10" using water/MeOH/HOAc 60:40:1 v/v/v as eluant.
3. The product, partially hydrated, (37 mg.), had m.p. 244° and the following n.m.r. in $D_2O$ + TFA:- 3.03 (d, 1H); 3.32 (d, 1H); 3.58 (d, 1H); 3.78 (d, 1H); 4.95 (d, 1H); 6.32 (s, 2H); (one β-lactam proton obscured by $H_2O$ resonance at 4.6–4.8).
4. Reaction carried out at 50° for 3 hours.
5. Product purified by HPLC on Whatman "Partisil 10" using water/MeOH/HOAc 75:25:1 v/v/v then 60:40:1 v/v/v as eluants.
6. Product, the hydrate (51 mg.), had m.p. 219–220 (decomp.) and the following n.m.r. in $D_2O$ + TFA:- 1.50 (d, 6H); 3.6 (d, 1H); 3.83 (d, 1H); 4.2 (s, 2H); 4.6–5.1 (m, 1H); 5.48 (d, 1H); 6.82 (s, 2H); (one β-lactam proton obscured by $H_2O$ resonance).
7. The 1-(2,2,2-trifluoroethyl)-1H—tetrazole-5-thiol used as starting material was prepared as follows:- A mixture of 2,2,2-trifluoroethylisothiocyanate (1.8 g.) and sodium azide (1.25 g.) in water (9 ml.) was heated on a steam bath for 18 hours. After cooling the mixture was extracted with ether (20 ml.) and the pH adjusted to 2 with concentrated HCl in the presence of EtOAc (20 ml.). The EtOAc extract was dried ($MgSO_4$) and evaporated to give a crystalline solid which on trituration with petroleum ether (b.p. 60–80°) gave 1-(2,2,2-trifluoroethyl)-1H—tetrazole-5-thiol (1.7 g.), m.p. 115–118°.
8. Reaction carried out at 50° for 1 hour.
9. Product purified by HPLC on Whatman "Partisil 10" using water/MeOH/HOAc 60:40:1 v/v/v as eluant.
10. The product (68% yield), obtained partially solvated with acetone, had the following n.m.r. in $D_2O$ + TFA:- 3.35 (d, 1H); 3.60 (d, 1H); 4.14 (s, 2H); 4.98 (d, 1H); 5.0 (q, 2H); 5.26 (d, 1H); 6.64 (s, 2H).
11. Reaction conducted for 2 hours at 40° then 2 hours at 60°.
12. Product purified by HPLC on Whatman "Partisil 10" using MeOH/water/HOAc 40:60:1 v/v/v as eluant.
13. The product (40%) crystallised on removal of the solvent. It had the following n.m.r. in $d_6DMSO$ +

$CD_3CO_2D$:- 2.05 (s, 3H); 2.97 (t, 2H); 3.52 (d, 1H); 3.78 (d, 1H); 4.36 (bs, 2H); 4.51 (t, 2H); 5.09 (d, 1H); 5.52 (d, 1H); 6.82 (s, 2H).

EXAMPLE 33

A solution of 0.18 g. of pivaloyloxymethyl 3-methyl-7-aminoceph-3-em-4-carboxylate (0.18 g.) and 2-fluoroimidazole hydrochloride (0.14 g.) in DMF (1 ml.) and acetonitrile (1 ml.) was heated at 50° for 7 hours. After evaporation the residue was chromatographed on silica gel using $CH_2Cl_2$/MeOH 95:5 v/v as eluant. The oily product was treated with one equivalent of HCl in MeOH. The solution was evaporated and the residue was triturated with ether and filtered to give pivaloyloxymethyl 7-(imidazol-2-yl)amino-3-methylceph-3-em-4-carboxylate hydrochloride having the following n.m.r. in $d_6DMSO$+$CD_3COOD$: 1.2 (s, 9H); 2.1 (s, 3H); 3.6 (m, 2H); 5.25 (d, 1H); 5.7 (d, 1H); 5.85 (m, 2H); 7.05 (s, 2H).

EXAMPLE 34

The process described in Example 7 was repeated using the appropriate t-butyl esters as starting material and the following compounds were thus obtained:

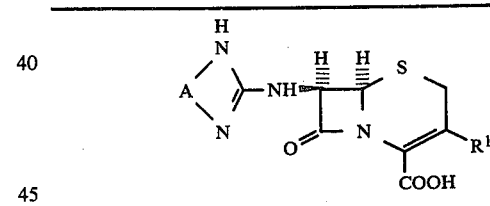

| $R^1$ | A | Footnotes |
|---|---|---|
| $CH_3$ | | 1, 2, 3 |
| $CH_2OCOCH_3$ | ![](N-CH=N-CH2-xylyl with cycle) | 4, 2, 5 |

Footnotes
1. Reaction carried out in TFA/anisole 3:1 v/v for 45 minutes.
2. The product was precipitated from $CH_2Cl_2$/MeOH solution with ether.
3. Product, the trifluoroacetate salt, had the following n.m.r. in $d_6DMSO$ + $CD_3COOD$:- 2.05 (s, 3H); 3.2–3.8 (m, 3H); 4.0 (t, 1H); 4.9–5.1 (m, 3H); 5.45 (br, 1H); 6.8 (d, 2H); 7.2 (d, 2H).
4. Reaction carried out in TFA/toluene 2:1 v/v for 30 minutes.
5. Product, the hydrobromide trifluoroacetate salt, had the following n.m.r. in $d_6DMSO$:- 1.72 (s, 8H); 2.09 (s, 3H); 3.18–4.0 (br, 6H); 4.7–5.1 (br, 4H); 5.2 (d, 1H); 5.9 (d, 1H); 6.9–7.5 (br, 3H); 8.5 (br, 1H).

The first starting material for use in the above process may be obtained as follows:

To a stirred suspension of p-benzyloxybenzaldehyde (21.2 g) in methanol (400 ml.) at 5° was dropwise added nitromethane (6.1 g.). After stirring 45 minutes at 5°–10° the reaction mixture was added to 5NHCl (25 ml.) with stirring. The resulting precipitate was washed with water and recrystallised from ethanol (400 ml.) to give 1-nitro-2-(p-benzyloxy)phenylethylene (18.7 g.) having the following n.m.r. in d6DMSO: 5.2 (s, 2H); 7.15 (d, 2H); 7.45 (s, 5H); 7.85 (d, 2H); 8.15 (s, 2H).

A suspension of the above nitroethylene (1.275 g.) in methanol (30 ml.) was added to three equivalents of hydroxylamine (prepared form the hydrochloride) in methanol (10 ml.). The mixture was stirred for 2 hours, evaporated to dryness and the residue taken up in CHCl3/ethanol 9:1 v/v. The solution was dried (MgSO4) and evaporated to give 1-hydroxyamino-1-(p-benzyloxy)phenyl-2-nitroethane having the following n.m.r. in d6DMSO: 4.8 (m, 3H); 5.15 (s, 2H); 7.05 (d, 2H); 7.4 (d, 2H); 7.5 (s, 5H).

A suspension of the above nitroethane derivative (0.56 g.) in ethanol (30 ml.) was hydrogenated at 3 atmospheres over Raney nickel and 10% w/w Pd/C for 18 hours at ambient temperature. The mixture was filtered, the filtrate evaporated and the residue dissolved in CH2Cl2/ether containing the minimum MeOH to effect solution. To this solution was added dry methanolic HCl and 1,2-diamino-1-(4-hydroxy)phenylethane hydrochloride was precipitated. It had the following n.m.r. in d6DMSO+CD3COOD: 2.9 (m, 2H); 4.1 (m, 1H); 6.55 (d, 1H); 7.0 (d, 2H).

The above diamine, in the form of the free base, was reacted with t-butyl 3-methyl-7-dibromomethyleneaminoceph-3-em-4-carboxylate using the general process described in the second part of Example 14. The product was purified by chromatography on silica gel using CH2Cl2/MeOH 3:97, 5:95 then 10:90 v/v as eluants to give t-butyl 3-methyl-7-[4-(4-hydroxy)phenyl-2-imidazolin-2-yl]aminoceph-3-em-4-carboxylate having the following n.m.r. in d6DMSO: 1.45 (s, 3H); 2.0 (s, 3H); 3.2–3.75 (m, 3H); 4.0 (t, 1H); 4.9–5.15 (m, 3H); 5.55 (d, 1H); 6.75 (d, 2H); 7.2 (d, 2H).

The second starting material for use in the above process may be obtained as follows:

To a solution of t-butyl 3-acetoxymethyl-7-(5-aminomethylbenzimidazol-2-yl)aminoceph-3-em-4-carboxylate (93 mg.) in dioxane (2 ml.) and methanol (3 ml.) at 20° was added dimethoxyhexahydro-1H-azepin-1-ylmethane (30 mg.) and then triethylamine. The mixture was cooled to 0° and stirred for 30 minutes. Two equivalents of HBr in methanol were added and the solvent evaporated. The residue was dissolved in the minimum CH2Cl2 and triethylamine hydrobromide precipitated by addition of ether. The product was purified by chromatography on magnesium silicate using CH2Cl2/MeOH 98:2 v/v as eluant to give t-butyl 3-acetoxymethyl-7-(5-hexahydro-1H-azepin-1-ylmethyleneaminomethylbenzimidazol-2-yl)aminoceph-3-em-4-carboxylate having the following n.m.r. in d6DMSO: 1.63 (s, 9H); 1.7 (s, 8H); 2.17 (s, 3H); 3.3–4.0 (br, 6H); 4.67 (s, 2H); 4.75 (d, 1H); 5.1 (d, 1H); 5.38 (d, 1H); 6.0 (d, 1H); 6.8–7.5 (m, 3H); 8.43 (s, 1H).

EXAMPLE 35

The process described in Example 30 was repeated using the appropriate starting materials and the following compounds were obtained:

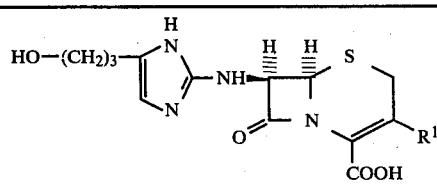

| R¹ | Footnotes |
|---|---|
| CH2OCOCH3 | 1 |
| CH2—S—(N—N triazole with N-CH3) | 2, 3 |
| CH2—S—(N—N—NH thiadiazole/triazole) | 2, 4 |

Footnotes
1. Product, the mixed toluene-p-sulphonate/acetate salt, had the following n.m.r. in d6DMSO:- 1.6–1.9 (m, 2H); 2.05 (s, 3H); 2.5 (t, 2H); 3.3–3.7 (m, 4H); 4.9 (q, 2H); 5.17 (d, 1H); 5.63 (q, 1H); 6.61 (s, 1H); 7.28 (q, 2H); 8.8 (s, 1H).
2. HPLC solvent was water/MeOH/HOAc 70:30:1 v/v/v.
3. Product, the mixed toluene-p-sulphonate/acetate salt, had the following n.m.r. in d6DMSO:- 1.6–1.9 (m, 2H); 2.5 (t, 2H); 3.3–3.7 (m, 4H); 3.95 (s, 3H); 4.34 (s, 2H); 5.08 (d, 1H); 5.70 (q, 1H); 6.58 (s, 1H); 8.65 (s, 1H).
4. Product, the mixed toluene-p-sulphonate/acetate salt, had the following n.m.r. in d6DMSO:- 1.6–1.9 (m, 2H); 2.44 (t, 2H); 3.42 (t, 2H); 3.59 (d, 2H); 4.04 (s, 2H); 5.08 (d, 1H); 5.50 (d, 1H); 6.57 (s, 1H); 7.84 (s, 1H).

The 2-fluoro-1-triphenylmethyl-4-(3-hydroxy)propylimidazole used as starting material may be prepared as follows:

To a solution of 2-fluoro-1-triphenylmethylimidazole (1.31 g.) in THF (22 ml.) at −70° under argon was added t-butyl lithium (4 ml. of a 2M solution in pentane). The red solution was stirred at −70° for 2 hours and then cuprous iodide (0.78 g.) added. The resulting dark red solution was stirred at −70° for 1 hour and then allyl bromide (1.8 ml.) added. The mixture was allowed to warm to ambient temperature over 18 hours and then poured into ether (150 ml.). The mixture was washed with saturated aqueous ammonium chloride (6×50 ml.), then brine (50 ml.), treated with charcoal and dried (MgSO4). The solution was evaporated to give 4-allyl-2-fluoro-1-triphenylmethylimidazole as a pale yellow solid, m.p. 136°–138°.

To a stirred solution of this allyl derivative (3.68 g.) in THF under argon at 5° was added diborane (40 ml. of a 1M solution in THF). The mixture was stirred at 5° for 15 minutes, then at ambient temperature for 16 hours. To the solution was added water (20 ml.) followed 15 minutes later by 2N NaOH (20 ml. of an aqueous solution) and H2O2 (6 ml. of a 30% w/w aqueous solution). The mixture was heated at 50° with vigorous stirring for 2 hours, cooled, saturated with NaCl and the layers separated. The aqueous layer was extracted with ether (3×75 ml.) and the combined extracts washed with brine and dried (MgSO4). The solvent was evaporated and the residue purified by chromatography on silica gel using CH2Cl2/MeOH 40:1 v/v as eluant to give 2-fluoro-1-triphenylmethyl-4-(3-hydroxy)propylimidazole as a crystalline solid having the following n.m.r. in CD3OD: 1.5–1.9 (m, 2H); 2.47 (t, 2H); 3.54 (t, 2H); 6.37 (s, 1H); 7.0–7.5 (m, 15H).

EXAMPLE 36

The process described in Example 7 was repeated using t-butyl 7-(4-aminomethyl-2-imidazolin-2-yl)amino-3-methylceph-3-em-4-carboxylate as starting material. The product was purified by precipitation from $CH_2Cl_2$ with ether and there was thus obtained 7-(4-aminomethyl-2-imidazolin-2-yl)amino-3-methylceph-3-em-4-carboxylic acid ditrifluoroacetate (50%) having the following n.m.r. in $D_2O$: 2.0 (s, 3H); 3.2–4.4 (m, 6H); 4.4–4.7 (m, 1H); 5.15 (d, 1H); 5.4 (d, 1H).

The t-butyl 7-(4-aminomethyl-2-imidazolin-2-yl)amino-3-methylceph-3-em-4-carboxylate used as starting material may be obtained as follows:

To a solution of 1,2-di(t-butoxycarbonylamino)-3-hydroxypropane (3 g.) and triethylamine (2 ml.) in $CH_2Cl_2$ (30 ml.) at 0° was added methanesulphonyl chloride (1.0 ml.) with stirring. Stirring at this temperature was continued for 1 hour and the mixture was then washed with water. The organic layer was separated, dried and the solvent evaporated to give 1,2-di(t-butoxycarbonylamino)-3-methanesulphonyloxypropane (2.9 g.), m.p. 94°–96°.

To a solution of sodium azide (0.825 g.) in water (2.5 ml.) was added a solution of the above methanesulphonate (2.34 g.) in dimethylacetamide (60 ml.). The mixture was stirred under argon at 60° for 7.5 hours and then the solvent was evaporated. The residue was dissolved in ethyl acetate, washed with water and dried and the solvent evaporated. The residue was purified by chromatograhy on silica gel using $CH_2Cl_2$/ether 50:50 v/v as eluant to give 1,2-di(t-butoxycarbonylamino)-3-azidopropane having the following n.m.r. in $CDCl_3$:1.45 (s, 18H), 3.25 (m, 2H); 3.45 (d, 2H); 3.65–4.1 (m, 1H); 4.75–5.3 (br, 2H).

To a solution of the above azide (1.15 g.) in anisole (10 ml.) at 0° was dropwise added TFA (5 ml.). The mixture was stirred for 15 minutes at 0°, then for 1 hour at ambient temperature. The solvent was evaporated and the residue triturated with ether/petroleum ether then with petroleum ether to give the ditrifluoroacetate of the free diamine (1.1 g.).

To a solution of the above diamine salt (1.029 g.) in methanol (3 ml.) was added sodium methoxide (0.324 g.). After stirring THF (37 ml.) was added, and then t-butyl 7-dibromomethyleneamino-3-methylceph-3-em-4-carboxylate (1.32 g.). The mixture was stirred for 2 hours, the solvent evaporated and the residue dissolved in a minimum of $CH_2Cl_2$ and the product precipitated with ether/petroleum ether. The product was purified by chromatography on silica gel using first $CH_2Cl_2$/ether 1:1 v/v and then this solvent containing 1% increasing to 6% v/v methanol. There was thus obtained t-butyl 7-(4-azidomethyl-2-imidazolin-2-yl)amino-3-methylceph-3-em-4-carboxylate as the hydrated hydrobromide having the following n.m.r. in $CDCl_3+CH_3OD$:1.45 (s, 9H); 2.15 (s, 3H); 3.4–4.1 (m, 7H); 5.1 (d, 1H); 5.35 (d, 1H).

A solution of the above azidomethyl derivative (42 mg.) in ethanol (2 ml.) and chloroform (1 ml.) was hydrogenated at 3 atmospheres for 20 hours at ambient temperature in the presence of $PtO_2$. The catalyst was removed by decantation, centrifugation and filtration through a fine pore filter and the solvent was then evaporated. There was thus obtained t-butyl 7-(4-aminomethyl-2-imidazolin-2-yl)amino-3-methylceph-3-em-4-carboxylate as the hydrochloride hydrobromide (70%) having the following n.m.r. in $CDCl_3+CD_3OD$:1.45 (s, 9H); 2.05 (s, 3H); 3.0–3.8 (m, 7H); 5.1 (d, 1H); 5.35 (d, 1H).

EXAMPLE 37

The process described in Example 30 was repeated using 7-amino-3-(1,2,3-thiadiazol-5-yl)thiomethylceph-3-em-4-carboxylic acid as starting material. The product was purified by HPLC using water/MeOH/HOAc 70:30:1 v/v/v as eluant to give 7-(imidazol-2-yl)amino-3-(1,2,3-thiadiazol-5-yl)thiomethylceph-3-em-4-carboxylic acid having the following n.m.r. in $d_6DMSO+CD_3CO_2D$:3.47 (d, 1H); 3.71 (d, 1H); 4.36 (s, 2H); 5.13 (d, 1H); 5.58 (d, 1H); 6.81 (s, 2H); 8.88 (s, 1H).

EXAMPLE 38

The process described in Example 7, but using only TFA at 0°, was repeated using t-butyl 7-(1-methoxybenzimidazol-2-yl)amino-3-methylceph-3-em-4-carboxylate as starting material to give 7-(1-methoxybenzimidazol-2-yl)amino-3-methylceph-3-em-4-carboxylic acid as the hydrated trifluoroacetate salt (69%) having the following n.m.r. in $d_6DMSO$:2.10 (s, 3H); 3.40 (d, 1H); 3.60 (d, 1H); 3.72 (s, 3H); 5.23 (d, 1H); 5.67 (d, 1H); 7.18–7.58 (m, 4H).

The t-butyl 7-(1-methoxybenzimidazol-2-yl)amino-3-methylceph-3-em-4-carboxylate used as starting material may be prepared as follows:

A mixture of 1-methoxybenzimidazole (1.48 g.) and α-bromoisobutyrophenone (2.27 g.) in toluene (6 ml.) was heated under reflux overnight. The mixture was cooled and the precipitate (1.0 g.) collected. A mixture of this precipitate (0.75 g.) and t-butyl 7-amino-3-methylceph-3-em-4-carboxylate (0.54 g.) in methanol (4 ml.) was stirred at ambient temperature for 6 days. $CH_2Cl_2$ (25 ml.) was added, the solution washed with aqueous $NaHCO_3$, water and brine and dried ($MgSO_4$). The solvent was evaporated and the residue purified by chromarography on silica gel using ether/$CH_2Cl_2$ 1:1 v/v as eluant to give t-butyl 7-(1-methoxybenzimidazol-2-yl)amino-3-methylceph-3-em-4-carboxylate which was used without further purification.

What we claim is:
1. A cephalosporin derivative of the formula:

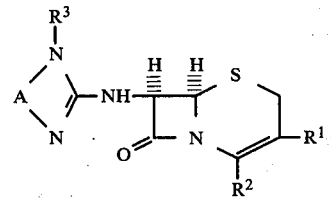

in which $R^1$ is a hydrogen or chlorine atom, or a methoxy, acetoxymethyl, carbamoyloxymethyl, pyridiniummethyl, (4-carbamoyl)pyridiniummethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 4-methyl-5-carboxymethylthiazol-2-ylthiomethyl, 1H-1,2,3-triazol-4-ylthiomethyl, 5-trifluoromethyl-1H-

1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-hydroxy-2-methyl-5-oxo-2H-1,2,4-triazin-3-yl)thiomethyl, (6-hydroxy-4-methyl-5-oxo-2H-1,2,4-triazin-3-yl)thiomethyl, (6-carboxymethyl-7-hydroxypyrrolo[1,2,b]pyridazin-2-yl)thiomethyl or 1,2,3-thiadiazol-5-ylthiomethyl radical;

$R^2$ is a carboxyl radical;
$R^3$ is a hydrogen atom; and
A is of the formula II;

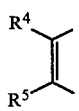

II in which $R^4$ is a hydrogen atom, an alkyl radical of 1 to 6 carbon atoms, a hydroxyalkyl radical of 1 to 6 carbon atoms or an aminoalkyl radical of 1 to 6 carbon atoms and $R^5$ is a hydrogen atom or $R^4$ and $R^5$ are both alkyl radicals of 1 to 6 carbon atoms.

2. A cephalosporin derivative selected from
3-[1-(2-dimethylamino)ethyl-1H-tetrazol-5-yl]thiomethyl-7-imidazol-2-ylaminoceph-3-em-4-carboxylic acid;
3-(1-methyl-1H-tetrazol-5-yl)thiomethyl-7-imidazol-2-yl-aminoceph-3-em-4-carboxylic acid;
3-(5-methyl-1,3,4-thiadiazol-2-yl)thiomethyl-7-(imidazol-2-yl)aminoceph-3-em-4-carboxylic acid;
3-(1H-1,2,3-triazol-4-yl)thiomethyl-7-(imidazol-2-yl)aminoceph-3-em-4-carboxylic acid;
3-(1-carboxymethyl-1H-tetrazol-5-yl)thiomethyl-7-(imidazol-2-yl)aminoceph-3-em-4-carboxylic acid;
7-(imidazol-2-yl)amino-3-(1,3,4-thiadiazol-2-yl)thiomethylceph-3-em-4-carboxylic acid;
7-(imidazol-2-yl)amino-3-(1-methyl-1H-tetrazol-5-yl)thiomethylceph-3-em-4-carboxylic acid;
7-(imidazol-2-yl)amino-3-(1-sulphomethyl-1H-tetrazol-5-yl)thiomethylceph-3-em-4-carboxylic acid;
7-(imidazol-2-yl)amino-3-(1-isopropyl-1H-tetrazol-5-yl)thiomethylceph-3-em-4-carboxylic acid;
7-(imidazol-2-yl)amino-3-[1-(2,2,2-trifluoro)ethyl-1H-tetrazol-5-yl]thiomethylceph-3-em-4-carboxylic acid;
7-(imidazol-2-yl)amino-3-[1-(2-methylthio)ethyl-1H-tetrazol-5-yl]thiomethylceph-3-em-4-carboxylic acid;
7-(imidazol-2-yl)amino-3-(5-trifluoromethyl-1H-1,2,4-triazol-3-yl)thiomethylceph-3-em-4-carboxylic acid;
7-(4-methylimidazol-2-yl)amino-3-(5-methyl-1,3,4-thiadiazol-2-yl)thiomethylceph-3-em-4-carboxylic acid;
7-(4-methylimidazol-2-yl)amino-3-(1H-1,2,3-triazol-4-yl)thiomethylceph-3-em-4-carboxylic acid;
7-(4,5-dimethylimidazol-2-yl)amino-3-(5-methyl-1,3,4-thiadiazol-2-yl)thiomethylceph-3-em-4-carboxylic acid;
3-acetoxymethyl-7-(4-hydroxymethylimidazol-2-yl)aminoceph-3-em-4-carboxylic acid;
and the pharmaceutically-acceptable acid-addition and base-addition salts thereof.

3. A cephalosporin derivative selected from 3-(1H-1,2,3-triazol-4-yl)thiomethyl-7-(imidazol-2-yl)aminoceph-3-em-4-carboxylic acid and the pharmaceutically-acceptable acid-addition and base-addition salts thereof.

4. A cephalosporin derivative of the formula

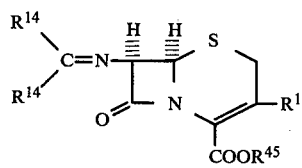

XXXVII in which $R^1$ is a hydrogen or chlorine atom, or a methoxy, acetoxymethyl, carbamoyloxymethyl, pyridiniummethyl, (4-carbamoyl)pyridiniummethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoro)ethyl-1H-tetrazol-5-ylthiomethyl, 1-phenyl-1H-tetrazol-5-ylthiomethyl, 1-(2-methylthio)ethyl-1H-tetrazol-5-ylthiomethyl, 1,3,4-thiadiazol-2-ylthiomethyl, 5-methyl-1,3,4-thiadiazol-2-ylthiomethyl, 4-methyl-5-carboxymethylthiazol-2-ylthiomethyl, 1H-1,2,3-triazol-4-ylthiomethyl, 5-trifluoromethyl-1H-1,2,4-triazol-3-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-hydroxy-2-methyl-5-oxo-2H-1,2,4-triazin-3-yl)thiomethyl, (6-hydroxy-4-methyl-5-oxo-2H-1,2,4-triazin-3-yl)thiomethyl, (6-carboxymethyl-7-hydroxypyrrolo[1,2,b]pyridazin-2-yl]thiomethyl or 1,2,3-thiadiazol-5-ylthiomethyl radical, $R^{14}$ is chlorine or bromine and $R^{45}$ is hydrogen, diphenylmethyl, t-butyl, trimethylsilyl, benzyl, substituted benzyl or 2,2,2-trichloroethyl.

* * * * *